(12) United States Patent
Desmet et al.

(10) Patent No.: US 9,315,805 B2
(45) Date of Patent: Apr. 19, 2016

(54) ALPHABODY LIBRARIES AND METHODS FOR PRODUCING THE SAME

(75) Inventors: Johan Desmet, Kortrijk (BE); Ignace Lasters, Antwerpen (BE); Maria Henderikx, Hasselt (BE); Anita Wehnert, Boorsem-Maasmechelen (BE)

(73) Assignee: Complix SA, Luxembourg (LU)

( * ) Notice: Subject to any disclaimer, the term of this patent is extended or adjusted under 35 U.S.C. 154(b) by 369 days.

(21) Appl. No.: 13/994,003

(22) PCT Filed: Jan. 6, 2011

(86) PCT No.: PCT/EP2011/050135
§ 371 (c)(1),
(2), (4) Date: Jun. 13, 2013

(87) PCT Pub. No.: WO2012/092970
PCT Pub. Date: Jul. 12, 2012

(65) Prior Publication Data
US 2014/0066601 A1    Mar. 6, 2014

(51) Int. Cl.
| | |
|---|---|
| *C40B 50/06* | (2006.01) |
| *C12N 15/10* | (2006.01) |
| *C07K 14/00* | (2006.01) |
| *C07K 16/24* | (2006.01) |
| *C07K 16/00* | (2006.01) |
| *C40B 50/12* | (2006.01) |

(52) U.S. Cl.
CPC .......... *C12N 15/1055* (2013.01); *C07K 14/001* (2013.01); *C07K 16/00* (2013.01); *C07K 16/244* (2013.01); *C12N 15/1037* (2013.01); *C07K 2317/33* (2013.01); *C07K 2318/20* (2013.01); *C40B 50/12* (2013.01)

(58) Field of Classification Search
None
See application file for complete search history.

(56) References Cited

FOREIGN PATENT DOCUMENTS

| | | |
|---|---|---|
| CN | 1458166 A | 11/2003 |
| EP | 2161278 A1 | 3/2010 |
| WO | WO2009/030780 A2 | 3/2009 |
| WO | WO2010/066740 A1 | 6/2010 |

OTHER PUBLICATIONS

International Preliminary Report on Patentability, PCT/EP2011/050135, dated Jul. 6, 2013, 7 pages.
Efimov, et al: Fibritin Encoded by Bacteriophage T4 Gene wac has a Parallel Triple-stranded alpha-Helical Coiled-coil Structure; J Mol Biol; 1994, vol. 242, pp. 470-486 XP002523719.
Herman, et al: The Trp Cage Motif as a Scaffold for the Display of a Randomized Peptide Library on Bacteriophage T7; J. Biol Chem, 2007, vol. 282, No. 13, pp. 9813-9824.

*Primary Examiner* — Christian Boesen
(74) *Attorney, Agent, or Firm* — Lathrop & Gage LLP; James H. Velema; Andrew T. Wilkins

(57) ABSTRACT

The invention provides single-chain Alphabody library comprising at least 100 different-sequence single-chain Alphabody polypeptides, wherein said Alphabody polypeptides differ from each other in at least one of a defined set of 5 to 20 variegated amino acid residue positions, and wherein at least 70% but not all of said variegated amino acid residue positions are located either in the loop, helix surface or linker region of the Alphabody. The invention further provides methods for use of the Alphabody libraries and Alphabodies obtainable by the methods of the invention.

5 Claims, 18 Drawing Sheets

| scAB013_L16 | N | a | d | a | d | a | d | a | d | C | SEQ ID NO |
|---|---|---|---|---|---|---|---|---|---|---|---|
| HRS1 | | IEEIQKQIAAIQKQIYRM | | | | | | | | | 1 |
| L1 | | | | | | | | | TGGSGGGSGGGSGGGSGMS | | 1 |
| HRS2 | | IEEIQKQIAAIQKQIYRM | | | | | | | | | 1 |
| L2 | | | | | | | | | TGGSGGGSGGGSGGGSGMS | | 1 |
| HRS3 | | IEEIQKQIAAIQKQIYRM | | | | | | | | | 1 |
| Full | MSIEEIQKQIAAIQKQIYRMTGGSGGGSGGGSGGGSGMSIEEIQKQIAAIQKQIYRMTGGSGGGSGGGSGGGSGMSIEEIQKQIAAIQKQIYRMTP (SEQ ID NO:1) | | | | | | | | | | 1 |

Fig. 2

```
sclib_AC11
       a   d   a   d   a   d
   N                             MKYLLPTAAAGLILLLAAQ
                                 PAMS
   HRS1 IEEIQKxIAxIQExIAxIQKxIYxM TGGSGGGSGGGSGGGSGM
   L1                            S
   HRS2 IEEIQKQIAAIQKQIAAIQKQIYAM TGGSGGGSGGGSGGGSGM
   L2                            S
   HRS3 IEEIQKQIxAIxEQIxAIxKQIxAM TPGGSGGAAAHHHHHHGR
   C                             AE
   PIII                          (PIII protein)
   Full MKYLLPTAAAGLILLLAAQPAMSIEEIQKxIAxIQExIAxIQKxIY
        xMTGGSGGGSGGGSGGGSGMSIEEIQKQIAAIQKQIAAIQKQIYA
        MTGGSGGGSGGGSGGGSGMSIEEIQKQIxAIxEQIxAIxKQIxAM
        TPGGSGGAAAHHHHHHGRAE-(PIII)(SEQ ID NO: 2)
```

Fig. 3A

| scLib AC7 | | |
|---|---|---|
| N | | MKYLLPTAAAGLLLLAAQPAMD |
| | a d a d | |
| HRS1 | IQQIQKxIAxIQExIYxM | |
| L1 | | TGGSGGGSGGGGSGGGSGMD |
| HRS2 | IQQIQKQIAAIQKQIYAM | |
| L2 | | TGGSGGGSGGGGSGGGSGMD |
| HRS3 | IQQIQKQIxAIxEQIxAM | |
| C | | TPGGSGGAAHHHHHHGRAE |
| PIII | | (PIII protein) |
| Full | MKYLLPTAAAGLLLLAAQPAMDIQQIQKxIAxIQExIYxMTG GSGGGSGGGGSGGGSGMDIQQIQKQIAAIQKQIYAMTGGSGGG SGGGSGGGSGMDIQQIQKQIxAIxEQIxAMTPGGSGGAAAHH HHHHGRAE-(PIII) (SEQ ID NO: 3) | |

Fig. 3B

```
scLib_C9
       a    d    a    d    a    d
N                                         MKYLLPTAAAGLLLLAAQ
                                          PAMS
HRS1  IEEIQKQIAAIQKQIAAIQKQIYAM            TGGSGGGSGGGSGGGSGM
L1                                        S
HRS2  IEEIQKQIAAIQKQIAAIQKQIYAM            TGGSGGGSGGGSGGGSGM
L2                                        S
HRS3  IEEIQxQIxxIQxQIxxIQxQIxxM            TPGGSGGAAAHHHHHHGR
C                                         AE
PIII                                      (PIII protein)
Full  MKYLLPTAAAGLLLLAAQPAMSIEEIQKQIAAIQKQIAAIQKQI
      YAMTGGSGGGSGGGSGGGSGMSIEEIQKQIAAIQKQIAAIQKQI
      YAMTGGSGGGSGGGSGGGSGMSIEEIQxQIxxIQxQIxxIQxQI
      xxMTPGGSGGAAAHHHHHHGRAE-(PIII)  (SEQ ID NO:5)
```

Fig. 3C

| scLib AClib | |
|---|---|
| N | MKYLLPTAAAGLLL LAAQPAGGS |
| HRS1  a  d  a  d  a  d<br>IEQIQKxIAxIQExIAxIQKxIYxM | |
| L1 | TGGSGGGSGGGGSGG SGGGS |
| HRS2  a  d  a  d  a  d<br>IEQIQKQIAAIQKQIAAIQKQIYAM | |
| L2 | TGSGGGGSGGSGGG GSGGS |
| HRS3  a  d  a  d  a  d<br>IEQIQKQIxAIxEQIxAIxKQIxAM | |
| C | TPGGSGGAAAHHHH HHGRAE<br>(PIII protein) |
| Full | MKYLLPTAAAGLLLLLAAQPAGGSIEQIQKxIAxIQExIAxI QKxIYxMTGGSGGGSGGGGSGGSGGGSIEQIQKQIAAIQKQI AAIQKQIYAMTGSGGGGSGGSGGGGSGGSIEQIQKQIxAIx EQIxAIxKQIxAMTPGGSGGAAAHHHHHHGRAE-<br>(PIII) (SEQ ID NO: 4) |

Fig. 4A

```
scLib_AC12
       a   d   a   d   a   d
N                                    MKYLLPTAAAGLILLLAAQ
                                     PAGGS
HRS1  IEQIQKxIAxIQExIAxIQKxIYAM
   L1                                TGGSGGGSGGGS
HRS2  IEQIQKQIAAIQKQIAAIQKQIYAM
   L2                                TGSGGGGSGGGS
HRS3  IEQIQKQIxAIxxQIxAIxxQIxAM
   C                                 TPGGSGGAAAHHHHHHGR
                                     AE
PIII                                 (PIII protein)
Full  MKYLLPTAAAGLILLLAAQPAGGSIEQIQKxIAxIQExIAxIQKxI
      YAMTGGSGGGSGGGSIEQIQKQIAAIQKQIAAIQKQIYAMTGSGGG
      GSGGSIEQIQKQIxAIxxQIxAIxxQIxAMTPGGSGGAAAHHHHHH
      HGRAE-(PIII) (SEQ ID NO: 6)
```

Fig. 4B

```
scLib B10
       a   d   a   d   a   d   a   d
  N                                              MKYLLPTAAAGLLLLAAQP
                                                 AMS
HRS1  IEEIQKQIAAIQEQIAAIQKQIYAM
  L1                                             TGGSGGSGGGGSGGGGSGGMS
HRS2  IEEIQKQIAxIQxxIxxIQxxIxxM
  L2                                             TGSGGGSGGGGSGGGGSGGMS
HRS3  IEEIQKxIAAIQEQIAAIQKQIYAM
  C                                              TPGGSGGAAAHHHHHHGRA
                                                 E
PIII                                             (PIII protein)
Full  MKYLLPTAAAGLLLLAAQPAMSIEEIQKQIAAIQEQIAAIQKQIYAM
      TGGSGGSGGGGSGGGGSGGMSIEEIQKQIAxIQxxIQxxIxxMTGS
      GGGSGGGGSGGGGSGGMSIEEIQKxIAAIQEQIAAIQKQIYAMTPGGSG
      GAAAHHHHHHGRAE-(PIII) (SEQ ID NO:7)
```

Fig. 4C

Table 3

| | |
|---|---|
| Con (SEQ_ID85) | GSIEQIQKxIAxIQExIAxIQKxIYAMTGSGGGSGGGSIEQIQKIAAI QKQIAAIQKQIYAMTGSGGGSGGGSIEQIQKQIxAIxxQIxAMTP |
| SEQ_ID8 & 87 | GSIEQIQKW+A*IQEWIAR+QKSIYAMTGSGGGSGGGSIEQIQKIAAI QKQIAAIQKQIYAMTGSGGGSGGGSIEQIQKQIRAISEQIVAIMLQIMAMTP |
| SEQ_ID9 | GSIEQIQKGIARIQEVIAKIQKGIYAMTGSGGGSGGGSIEQIQKIAAI QKQIAAIQKQIYAMTGSGGGSGGGSIEQIQKQIVAITHQITAIWQIWAMTP |
| SEQ_ID10 | GSIEQIQKRIAFIQETIAWIQKNIYAMTGSGGGSGGGSIEQIQKIAAI QKQIAAIQKQIYAMTGSGGGSGGGSIEQIQKQISAIARQIRAILGQIFAMTP |
| SEQ_ID11 | GSIEQIQKTIAMIQEYIAWIQKKIYAMTGSGGGSGGGSIEQIQKIAAI QKQIAAIQKQIYAMTGSGGGSGGGSIEQIQKQIRAIVGQIMATLRQITAMTP |
| SEQ_ID12 | GSIEQIQKFIANIQELIACIQKNIYAMTGSGGGSGGGSIEQIQKIAAI QKQIAAIQKQIYAMTGSGGGSGGGSIEQIQKQITAIASQIYAIVAQITAMTP |
| SEQ_ID13 | GSIEQIQKGIALIQEWIAMIQKSIYAMTGSGGGSGGGSIEQIQKIAAI QKQIAAIQKQIYAMTGSGGGSGGGSIEQIQKQILAISLQIMAILEQIMAMTP |
| SEQ_ID14 & 88 | GSIEQIQKIIAGIQEGIASIQK*IYAMTGSGGGSGGGSIEQIQKIAAI QKQIAAIQKQIYAMTGSGGGSGGGSIEQIQKQISAIVQQIMAIFAQITAMTP |
| SEQ_ID15 | GSIEQIQKYIAPIQEIIAKIQKLIYAMTGSGGGSGGGSIEQIQKIAAI QKQIAAIQKQIYAMTGSGGGSGGGSIEQIQKQIGAIISQIGAILGQIYAMTP |
| SEQ_ID16 | GSIEQIQKKIATIQEYIAYIQKFIYAMTGSGGGSGGGSIEQIQKIAAI QKQIAAIQKQIYAMTGSGGGSGGGSIEQIQKQIKAILGQIGAIIGQIWAMTP |
| SEQ_ID17 | GSIEQIQKKIAVIQBVIAGIQKGIYAMTGSGGGSGGGSIEQIQKIAAI QKQIAAIQKQIYAMTGSGGGSGGGSIEQIQKQISAIIIQITAIVKQIMAMTP |

Fig. 8A

Table 3 (cont.)

| SEQ_ID | Sequence |
|---|---|
| SEQ_ID18 & 89 | GSIEQIQKYIAMIQE*IALIQKSIYAMTGGSGGGSGGGSIEQIQKQIAAI QKQIAAIQKQIYAMTGSGGGSGGGSIEQIQKQIAAIARQIFAIINQITAMTP |
| SEQ_ID19 | GSIEQIQK+IA+IQE+IANIQKRIYAMTGSGGGSGGGSIEQIQKQIRAI+EQIAAIF+QIFAMTP |
| SEQ_ID20 | QKQIAAIQKQIYAMTGSGGGSGGGSIEQIQKRIAPIQECIAFIQKLIYAMTGSGGGSGGGSIEQIQKQIAAI |
| SEQ_ID21 & 90 | QKQIAAIQKQIYAMTGSGGGSGGGSIEQIQKRIARIQEPIA*IQKGIYAMTGSGGGSGGGSIEQIQKQITAIGRQIMAIFIQIWAMTP |
| SEQ_ID22 | GSIEQIQK+IA+IQEWIAIQIQK+IYAMTGSGGGSGGGSIEQIQKQIWAISQQITAIVIQIFAMTP |
| SEQ_ID23 & 91 | QKQIAAIQKQIYAMTGSGGGSGGGSIEQIQKQIWAIVSQI+AILVQI+AMTP GSIEQIQKVIAYIQEKIAVIQKSIYAMTGSGGGSGGGSIEQIQKQI*AIGSQITAIVRQILAMTP |
| SEQ_ID24 | QKQIAAIQKQIYAMTGSGGGSGGGSIEQIQKRIAGIQERIA+IQK+IYAMTGSGGGSGGGSIEQIQKQIEAIS+QIVAIIGQILAMTP |
| SEQ_ID25 | GSIEQIQKTIASIQEVIAAIQKYIYAMTGSGGGSGGGSIEQIQKQIAAIGSQIIAIVRQIRAMTP |
| SEQ_ID26 | QKQIAAIQKQIYAMTGSGGGSGGGSIEQIQKTIAAIQECIARIQKAIYAMTGSGGGSGGGSIEQIQKQIAAI GSIEQIQKVIARIQEVIASIQKYIYAMTGSGGGSGGGSIEQIQKQIRAIVSQISAILIQIGAMTP |
| SEQ_ID27 | QKQIAAIQKQIYAMTGSGGGSGGGSIEQIQKQIGAIVTQILAIISQITAMTP GSIEQIQKSIARIQEGIAPIQKMIYAMTGSGGGSGGGSIEQIQKQIMAIAGQIGAIL*QIRAMTP |
| SEQ_ID28 & 92 | QKQIAAIQKQIYAMTGSGGGSGGGSIEQIQKQIMAIAGQIGAIL*QIRAMTP |

Fig. 8B

Table 3 (cont.)

| | |
|---|---|
| SEQ_ID29 | GSIEQIQKMIAPIQELIARIQKDIYAMTGSGGSGGSGGSIEQIQKQIAAI QKQIAAIQKQIYAMTGSGGGSGGSSGGSIEQIQKQIGAITRQILAILVQIGAMTP |
| SEQ_ID30 | GSIEQIQKPIASIQECIARIQKTIYAMTGSGGGSGGSGGGSIEQIQKQIAAI QKQIAAIQKQIYAMTGSGGGSGGSSGGSIEQIQKQIKAIRTQIFAIFRQIYAMTP |
| SEQ_ID31 & 93 | GSIEQIQKPIALIQESIA*IQKYIYAMTGSGGGSGGSGGGSIEQIQKQIAAI QKQIAAIQKQIYAMTGSGGGSGGSSGGSIEQIQKQIFAI*RQIMAILRQINAMTP |
| SEQ_ID32 | GSIEQIQKYIARIQEKIAYIQKMIYAMTGSGGGSGGSGGGSIEQIQKQIAAI QKQIAAIQKQIYAMTGSGGGSGGSSGGSIEQIQKQIIAIGSQILAILDQIYAMTP |
| SEQ_ID33 | GSIEQIQKLIAVIQEYIALIQKKIYAMTGSGGGSGGSGGGSIEQIQKQIAAI QKQIAAIQKQIYAMTGSGGGSGGSSGGSIEQIQKQIKAIATQISAIIRQIFAMTP |
| SEQ_ID34 | GSIEQIQKWIAQIQENIADIQKLIYAMTGSGGGSGGSGGGSIEQIQKQIAAI QKQIAAIQKQIYAMTGSGGGSGGSSGGSIEQIQKQIPAIAYQILAIIRQISAMTP |
| SEQ_ID35 & 94 | GSIEQIQKWIAGIQEAIA*IQKLIYAMTGSGGGSGGSGGGSIEQIQKQIAAI QKQIAAIQKQIYAMTGSGGGSGGSSGGSIEQIQKQIRAIRSQIRAILSQIIAMTP |
| SEQ_ID36 | GSIEQIQKLIARIQESIAMIQKKIYAMTGSGGGSGGSGGGSIEQIQKQIAAI QKQIAAIQKQIYAMTGSGGGSGGSSGGSIEQIQKQIIAIAKQILAIVSQIKAMTP |
| SEQ_ID37 & 95 | GSIEQIQKLIAFIQEGIASIQK*IYAMTGSGGGSGGSGGGSIEQIQKQIAAI QKQIAAIQKQIYAMTGSGGGSGGSSGGSIEQIQKQIAAIGNQIMAILQQIKAMTP |
| SEQ_ID38 | GSIEQIQKTIARIQEGIAVIQKLIYAMTGSGGGSGGSGGGSIEQIQKQIAAI QKQIAAIQKQIYAMTGSGGGSGGSSGGSIEQIQKQIRAIVRQITAIMTQIFAMTP |
| SEQ_ID39 & 96 | GSIEQIQKAIARIQE*IAIIQKKIYAMTGSGGGSGGSGGGSIEQIQKQIAAI QKQIAAIQKQIYAMTGSGGGSGGSSGGSIEQIQKQIVAIIAQIAIIPQIIAMTP |
| SEQ_ID40 | GSIEQIQKGIAPIQEMIASIQKVIYAMTGSGGGSGGSGGGSIEQIQKQIAAI QKQIAAIQKQIYAMTGSGGGSGGSSGGSIEQIQKQIMAIAFQIFAIMRQILAMTP |

Fig. 8C

Table 3 (cont.)

| | |
|---|---|
| SEQ_ID41 & 97 | GSIEQIQKPIA*IQERIAWIQKRIYAMTGSGGGSGGGSGGGSIEQIQKQIAAI QKQIAAIQKQIYAMTGGSGGGSGGGSIEQIQKQIBAITGQIVAIVFQIYAMTP |
| SEQ_ID42 & 98 | GSIEQIQK*IAKIQEFIARIQKVIYAMTGSGGGSGGGSIEQIQKQIAAI QKQIAAIQKQIYAMTGGSGGGSGGGSIEQIQKQICAIAVQIDAILGQILAMTP |
| SEQ_ID43 | GSIEQIQKFIAPIQEYIAAIQKIIYAMTGGSGGGSGGGSIEQIQKQIAAI QKQIAAIQKQIYAMTGGSGGGSGGGSIEQIQKQIAAIASQIKAIVTQIVAMTP |
| SEQ_ID44 & 99 | GSIEQIQKIIAGIQE*IALIQKAIYAMTGSGGGSGGGSIEQIQKQIAAI QKQIAAIQKQIYAMTGSGGGSGGGSIEQIQKQIYAIGLQILAIMNQIWAMTP |
| SEQ_ID45 | GSIEQIQKFIASIQESIARIQKSIYAMTGSGGGSGGGSIEQIQKQIAAI QKQIAAIQKQIYAMTGSGGGSGGGSIEQIQKQITAIARQIVAIIVQITAMTP |
| SEQ_ID46 & 100 | GSIEQIQKFIAAIQEYIATIQK*IYAMTGSGGGSGGGSIEQIQKQIAAI +KQIAAIQKQIYAMTGSGGGSGGGSIEQIQKQICAIAYQIIAIVNQIKAMTP |
| SEQ_ID47 | GSIEQIQKGIALIQETIAYIQKSIYAMTGSGGGSGGGSIEQIQKQIAAI QKQIAAIQKQIYAMTGSGGGSGGGSIEQIQKQITAIARQITAIIAQIFAMTP |
| SEQ_ID48 & 101 | GSIEQIQKTTA*IQEPIAIIQKRIYAMTGSGGGSGGGSIEQIQKQIAAI QKQIAAIQKQIYAMTGSGGGSGGGSIEQIQKQIKAITSQISAIMSQIWAMTP |
| SEQ_ID49 | GSIEQIQKVIAPIQEYIAIIQKYIYAMTGSGGGSGGGSIEQIQKQIAAI QKQIAAIQKQIYAMTGSGGGSGGGSIEQIQKQISAIMRQIYAIISQIQAMTP |
| SEQ_ID50 | GSIEQIQKLIASIQEYIATIQKLIYAMTGSGGGSGGGSIEQIQKQIAAI QKQIAAIQKQIYAMTGSGGGSGGGSIEQIQKQISAIMIQINAILGQIFAMTP |
| SEQ_ID51 & 102 | GSIEQIQKGIAVIQETIA*IQKIIYAMTGSGGGSGGGSIEQIQKQIAAI QKQIAAIQKQIYAMTGSGGGSGGGSIEQIQKQILAIAQQIHAIVSQIVAMTP |
| SEQ_ID52 & 103 | GSIEQIQK+IA+IQEAIA+IQKVIYAMTGSGGGSGGGSIEQIQKQIAAI QKQIAAIQKQIYAMTGSGGGSGGGSIEQIQKQI*AIWEQIAAILKQIVAMTP |

Fig. 8D

Table 3 (cont.)

| | |
|---|---|
| SEQ_ID53 | GSIEQIQKRIAYIQEAIARIQKWIYAMTGSGGGSGGGSIEQIQKIAAI<br>QKIAAIQKIYAMTGSGGGSGGGSIEQIQKIGAI+MQILAIF+QI+AMTP |
| SEQ_ID54 | GSIEQIQKKIAGIQEVIALIQKFIYAMTGSGGGSGGGSIEQIQKIAAI<br>QKQIAAIQKQIYAMTGSGGGSGGGSIEQIQKQIRAISSQIQAIVLQILAMTP |
| SEQ_ID55 & 104 | GSIEQIQKFIAAIQEYIATIQK*IYAMTGSGGGSGGGSIEQIQKIAAI<br>QKQIAAIQKQIYAMTGSGGGSGGGSIBQIQKQIGAIAYQIIAIVNQIKAMTP |
| SEQ_ID56&105&118 | GSIEQIQKGIAPIQEPIA*IQKLIYAMTGSGGGSGGGSIEQIQKIAAI<br>QKQIAAIQKQIYAMTGSGGGSGGGSIEQIQKQI*AIANQIRAIINQIMAMTP |
| SEQ_ID57 | GSIEQIQKAIAKIQETIAFIQKSIYAMTGSGGGSGGGSIEQIQKQITAIAGQIYAILQQIFAMTP<br>G+IE+I+K*IAGIQEWIAPI+KRIYAMTGSGGGSGGGG+IEQIQKQIAAI |
| SEQ_ID58 & 106 | QKQIAAIQK+IYAMTGSGGGSGGGSIEQI+KQISAIIDQI+AIFAQIIAMTP<br>GSIEQIQK*IAGIQEWIAPIQKRIYAMTGSGGGSGGGSIEQIQKIAAI |
| SEQ_ID59 & 107 | QKQIAAIQKQIYAMTGSGGGSGGGSIEQIQKQISAIIDQIRAIFAQIIAMTP<br>GSIEQIQK+IAWIQEYIA+IQK+IYAMTGSGGGSGGGSIEQIQKIAAI |
| SEQ_ID60 | QKQIAAIQKQIYAMTGSGGGSGGGSIEQIQKQI+AIATQILAIV+QIVAMTP<br>GSIEQIQKFIAMIQEVIA*IQKNIYAMTGSGGGSGGGSIEQIQKIAAI |
| SEQ_ID61 & 108 | QKQIAAIQKQIYAMTGSGGGSGGGSIEQIQKQIRAIREQIKAILHQITAMTP<br>GSIEQIQKRIA*IQEPIANIQKRIYAMTGSGGGSGGGSIEQIQKIAAI |
| SEQ_ID62 & 109 | QKQIAAIQKQIYAMTGSGGGSGGGSIEQIQKQIEAITNQIWAIITQIWAMTP<br>GSIEQIQKVIA+IQEYIAGIQK+IYAMTGSGGGSGGGG+IE+IQKQIAAI |
| SEQ_ID63 | +KQIAAIQKQIYAMTG+GGGGS+GS+EQI+KQIRAITSQIWAII+QIIAMTP<br>GSIEQIQKYIA+IQETIA+IQKLIYAMTGSGGGSGGGSIEQIQK+IA+I |
| SEQ_ID64 | QKQIAAIQKQIYAMTGSG+GGGSGGGSIEQIQKQISAII+QI+AIL+QIPAMTP |

Fig. 8E

Table 3 (cont.)

| | |
|---|---|
| SEQ_ID65 & 110 | GSIEQIQKVIAQIQE*IAMIQKAIYAMTGGSGGSIEQIQKOIRAIMOISAIFNOIFAMTP |
| | QKQIAAIQKQIYAMTGGGSGGSIEQIQKQIRAIMQISAIFNQIFAMTP |
| SEQ_ID66 | GSIEQIQKWIALIQEKIARIQKDIYAMTGGGSGGSIEQIQKQINAIAGQILAIATQIMAMTP |
| SEQ_ID67 | QKQIAAIQKQIYAMTGGGSGGSIEQIQKQIGAIMLQIMAIIRQIPAMTP |
| | GSIEQIQKRIAGIQEYIAKIQKSIYAMTGGSGGGSIEQIQKQIAAI |
| SEQ_ID68 | QKQIAAIQKQIYAMTGGGSGGSIEQIQKQISAISRQIVATVSQILAMTP |
| | GSIEQIQKNIAPIQEVIARIQKCIYAMTGGGSGGSIEQIQKQIAAI |
| SEQ_ID69 & 111 | QKQIAAIQKQIYAMTGGGSGGSIEQIQKQI*AISSQIRAILTQILAMTP |
| | GSIEQIQKTIAWIQESIANIQKGIYAMTGGGSGGSIEQIQKQIAAI |
| SEQ_ID70 & 112 | QKQIAAIQKQIYAMTGGGSGGSIEQIQKQIRAIG*QIIAIVEQIWAMTP |
| | GSIEQIQKVIARIQEPIAVIQKMIYAMTGGGSGGSIEQIQKQIAAI |
| SEQ_ID71 | QKQIAAIQKTIAKIQERIAWIQKVIYAMTGGGSGGSIEQIQKQISAIRSQILAIIRQIFAMTP |
| SEQ_ID72 | QKQIAAIQKQIYAMTGGGSGGSIEQIQKQIKAISYQIIAIMRQILAMTP |
| | GSIEQIQKHIA*IQEKIAWIQKLIYAMTGGSGGGSIEQIQKQIAAI |
| SEQ_ID73 & 113 | QKQIAAIQKQIYAMTGGGSGGSIEQIQKQISAIIGQIYAIASQIMAMTP |
| | GSIEQIQKVIAWIQEBSIASIQKRIYAMTGGGSGGSIEQIQKQIAAI |
| SEQ_ID74 | QKQIAAIQKQIYAMTGGGSGGSIEQIQKQIQAIANQITAIVRQILAMTP |
| | GSIEQIQKVIA*IQEYIAWIQKSIYAMTGGGSGGSIEQIQKQIAAI |
| SEQ_ID75 & 114 | QKQIAAIQKQIYAMTGGGSGGSIEQIQKQIRAIAMQIEAITTQIRAMTP |
| | GSIEQIQKGIAAIQ++IAMI+KSIYAMTGGSGGGSIEQI++QIA+I |
| SEQ_ID76 | QKQIAAIQKQIYAMTG++GGGSGGSIE+I+KQITAI+TQI+AI+SQIL+MT+ |

Fig. 8F

Table 3 (cont.)

| | |
|---|---|
| SEQ_ID77 | GSIEQIQKCIAFIQERIAGIQKRIYAMTGSGGGSGGGSIEQIQKQIAAI QKQIAAIQKQIYAMTGSGGGSGGGSIEQIQKQIFAICKQIFAIVKQILLAMTP |
| SEQ_ID78 | GSIEQIQKPIAAIQEKIARIQKRIYAMTGSGGGSGGGSIEQIQKQIAAI QKQIAAIQKQIYAMTGSGGGSGGGSIEQIQKQIMAINRQILAILRQILAMTP |
| SEQ_ID79 & 115 | GSIEQIQKYIA*IQBKIAWIQKMIYAMTGSGGGSGGGSIEQIQKQIAAI QKQIAAIQKQIYAMTGSGGGSGGGSIEQIQKQITVAISFQIWAIVRQITAMTP |
| SEQ_ID80 | GSIEQIQKFIASIQECIASIQKVIYAMTGSGGGSGGGSIEQIQKQIAAI QKQIAAIQKQIYAMTGSCGGGSGGGSIEQIQKQIGAIAAQIIAIVEQIVAMTP |
| SEQ_ID81 | GSIEQIQKKIAVIQEMIALIQKGIYAMTGSGGGSGGGSIEQIQKQIAAI QKQIAAIQKQIYAMTGSGGGSGGGSIEQIQKQISAIAAQISAIIKQIMAMTP |
| SEQ_ID82 & 116 | GSIEQIQKNIAWIQERIAMIQKLIYAMTGSGGGSGGGSIEQIQKQIAAI QKQIAAIQKQIYAMTGSGGGSGGGSIEQIQKQI*AIIYQIVAIIRQIPAMTP |
| SEQ_ID83 & 117 | GSIEQIQKLIARIQE*IALIQKRIYAMTGSGGGSGGGSIEQIQKQIAAI QKQIAAIQKQIYAMTGSGGGSGGGSIEQIQKQIVAIMYQIYAIIKQIWAMTP |
| SEQ_ID84 | GSIEQIQKGIAAIQEWIATIQKRIYAMTGSGGGSGGGSIEQIQKQIAAI QKQIAAIQKQIYAMTGSGGGSGGGSIEQIQKQIRAITIQIIAIIQQIWAMTP |

Fig. 8G

ALPHABODY LIBRARIES AND METHODS FOR PRODUCING THE SAME

RELATED APPLICATIONS

This application is a 35 U.S.C. §371 filing of International Application No. PCT/EP2011/050135, filed Jan. 6, 2011. The entire contents of which incorporated herein by reference.

SEQUENCE LISTING

The instant application contains a Sequence Listing which has been submitted electronically in ASCII format and is hereby incorporated by reference in its entirety. Said ASCII copy, created on Oct. 31, 2013, is named 547521CX9-001US_SL.txt and is 105,260 bytes in size.

FIELD OF THE INVENTION

The present invention relates to the field of polypeptide libraries and methods for the production thereof as well as to uses of such polypeptide libraries for the development of Alphabodies for prophylactic, therapeutic or diagnostic purposes.

BACKGROUND

Antibody (-based) libraries have been extensively used in the past for the selection and identification of proteins specifically binding to one or more target compounds of interest.

The applicability of the various types of antibody libraries varies. For instance, immune libraries are characterized by a high percentage of high affinity antibodies directed to a limited amount of target antigens (immunogens), as in such libraries in vivo antibody affinity maturation has taken place in immunized animals or human patients. Therefore, immune libraries with a relatively small complexity are capable of generating high affinity binders for specific antigens. However, usually, for each antigen or patient group studied, a separate immune library has to be constructed. In addition, for obvious ethical reasons, active immunization of humans is not possible, and accordingly the generation of human antibodies to most targets is not feasible via this approach.

On the other hand, in naïve and synthetic antibody (-based) libraries, the antibody repertoire present did not evolve through antigen driven antibody maturation. Consequently, the complexity of these libraries has to be very high to ensure a sufficient statistical chance that some of the antibodies in the libraries are capable of binding to any given target with reasonable or high affinity.

Antibodies are fairly large proteins and sensitive to treatments like heating, freeze-thawing proteolytic cleavage and ammonium sulphate precipitation. Also the size of antibodies limits their modes of administration.

Accordingly, in view of the disadvantages of the antibody scaffolds, there remains a need for alternative and improved protein libraries (and methods for the production thereof), which reliably yield good-quality proteins having a high affinity and activity towards a variety of target proteins of interest.

WO2010/066740 and EP 2 161 278 describe Alphabody structures as single-chain triple-stranded alpha-helical coiled coil scaffolds. However, up to now it has not been disclosed or suggested how the Alphabody scaffolds can be manipulated to obtain Alphabody libraries which yield a high number of binding partners capable of specifically binding to target molecules of interest with sufficient affinity.

SUMMARY OF THE INVENTION

The present inventors have developed new methods which allow the generation of Alphabody libraries (referred to herein as '(single-chain) Alphabody libraries of the (present) invention'). In addition, the inventors have found that the Alphabody libraries of the invention can be used for the screening for and/or selection of one or more Alphabodies that specifically bind to a target molecule of interest. Accordingly, the present inventors have developed novel and improved libraries comprising different-sequence Alphabody polypeptides, from which binders can be isolated which bind to a target molecule of interest with high affinity and specificity and which overcome one or more of the disadvantages of the prior art binders. Moreover, it has been found that the isolated Alphabody binders have several advantages over the traditional (immunoglobulin and non-immunoglobulin) binding agents known in the art. Such advantages include, without limitation, the fact that they are compact and small in size (between 10 and 14 kDa, which is 10 times smaller than an antibody), they are extremely (thermo)stable (having a melting temperature of more than 100° C.), and are relatively insensitive to changes in pH and to proteolytic degradation. In addition, the Alphabody binders isolated from the libraries and by the methods of the present invention are highly soluble and have a structure which is based on natural motifs but is designed via protein engineering techniques.

An important aspect of the invention is the Alphabody regions that are selected for introducing amino acid sequence variation (i.e., the variegated Alphabody regions) in the Alphabody libraries of the invention. As will be detailed herein, there are different regions defined for a folded Alphabody scaffold structure, i.e. the "helix surface", "groove" and "loop" regions and each has its own intrinsic three-dimensional (3-D) shape in. For example, an Alphabody groove will intrinsically have an (elongated) concave shape, a helix surface will intrinsically have an (elongated) convex shape, and a linker fragment will intrinsically have a flexible (variable) shape. Alphabodies are unique in this respect, since they are the only scaffold molecules which unite a groove, helix surface and flexible linker fragment (or loop) in one and the same scaffold structure.

The present inventors have however considered the construction of Alphabody libraries wherein the introduced sequence variation is not exclusively confined to one particular area.

Accordingly, in one aspect the present invention provides single-chain Alphabody libraries comprising at least 100 different-sequence single-chain Alphabody polypeptides, wherein the said Alphabody polypeptides differ from each other in at least one of a defined set of 5 to 20 variegated amino acid residue positions, and wherein at least 70% but not all of the variegated amino acid residue positions are located either:
  (i) at heptad e-positions in a first alpha-helix of the Alphabody polypeptides and at heptad g-positions in a second alpha-helix, parallel to the first alpha-helix, and optionally at heptad b-positions in the first alpha-helix of the Alphabody polypeptides and/or at heptad c-positions in the second alpha-helix of the Alphabody polypeptides, or
  (ii) at heptad b-, c- and f-positions in one alpha-helix of the Alphabody polypeptides, or
  (iii) at positions in a linker fragment connecting two consecutive alpha-helices of the Alphabody polypeptides.

Thus, according to the present invention at least 70% but not all of the variegated amino acid residue positions are located in one of the regions selected from the "loop", "helix surface" or "linker" regions as described herein.

In certain particular embodiments, a single-chain Alphabody library of the invention may be a mixture of Alphabody libraries comprising at least two different constituting libraries.

In a further aspect, the present invention also provides nucleic acid and vector libraries, which encode the single-chain Alphabody (polypeptide) libraries of the invention or a mixture of single-chain Alphabody libraries of the invention.

In yet a further aspect, the present invention provides libraries of host cells, wherein each host cell comprises maximally one member of a nucleic acid or vector library, encoding a single-chain Alphabody (polypeptide) library of the invention or a mixture of single-chain Alphabody libraries of the invention.

In yet another aspect, the present invention provides uses of the single-chain Alphabody libraries of the invention or uses of mixtures of single-chain Alphabody libraries of the invention for in vitro protein evolution, such as a phage display, yeast display, bacterial display or mRNA display.

In yet a further aspect, the present invention provides methods for the production of single-chain Alphabody libraries of the invention, these methods comprising at least the steps of:
a) producing a nucleic acid or a vector library encoding a single-chain Alphabody library of the invention or encoding a mixture of single-chain Alphabody libraries of the invention, and
b) expressing the nucleic acid or vector library under conditions suitable for the production of the single-chain Alphabody library.

In certain embodiments of these production methods, the step b) of expressing the nucleic acid or vector library, comprises introducing the individual members of the nucleic acid or vector library into host cells and culturing the host cells in a medium under conditions suitable for the production of the single-chain Alphabody library.

In further particular embodiments, the methods for the production of single-chain Alphabody libraries of the invention, further comprise the step of isolating the single-chain Alphabody library produced in step b) from the host cells and/or from the medium.

In yet a further aspect, the present invention provides for the use of the single-chain Alphabody libraries of the present invention in the production of single-chain Alphabody polypeptides having detectable binding affinity for a target molecule of interest. More particularly, the present invention provides methods for the production of one or more single-chain Alphabody polypeptides having detectable binding affinity for a target molecule of interest, or detectable in vitro activity on target proteins or cells of interest, the methods at least comprising the steps of:
a) producing a single-chain Alphabody library according to the invention or a mixture of single-chain Alphabody libraries according to the invention,
b) selecting one or more single-chain Alphabody polypeptides having detectable binding affinity for a target molecule of interest, or detectable in vitro activity on target proteins or cells of interest, and, optionally,
c) isolating the one or more single-chain Alphabody polypeptides.

In certain particular embodiments, the step of selecting one or more single-chain Alphabody polypeptides having detectable binding affinity for a target molecule of interest, comprises:

b1) contacting the target molecule of interest with a single-chain Alphabody library according to the invention or with a mixture of single-chain Alphabody libraries according to the invention,
b2) identifying from the single-chain Alphabody library or mixture of single-chain Alphabody libraries being contacted with the target molecule of interest, the one or more single-chain Alphabody polypeptides having detectable binding affinity for the target molecule of interest; and, optionally,
b3) determining the amino acid or nucleotide sequence of the one or more single-chain Alphabody polypeptides having detectable binding affinity for the target molecule of interest.

In certain particular embodiments of the methods for the production of one or more single-chain Alphabody polypeptides having detectable binding affinity for a target molecule of interest, the Alphabody library or the mixture of Alphabody libraries is further enriched for single-chain Alphabody polypeptides having detectable binding affinity for the target molecule of interest by iterative execution of contacting step b1) and identifying step b2) of the selection.

In a further aspect, the present invention also provides single-chain Alphabody polypeptides having detectable binding affinity for a target molecule of interest, or detectable in vitro activity on target proteins or cells of interest, wherein these single-chain Alphabody polypeptides are obtainable by the methods of the invention.

In yet a further aspect, the present invention provides nucleic acids encoding the single-chain Alphabody polypeptides produced by the methods of the invention.

In further aspects, the present invention provides vectors comprising the nucleic acids encoding the single-chain Alphabody polypeptides produced by the methods of the invention and host cells comprising the nucleic acids or vectors encoding the single-chain Alphabody polypeptides produced by the methods of the invention.

DETAILED DESCRIPTION OF THE INVENTION

As used herein, the singular forms 'a', 'an', and the include both singular and plural referents unless the context clearly dictates otherwise.

The terms 'comprising', 'comprises' and 'comprised of' as used herein are synonymous with 'including', 'includes' or 'containing', 'contains', and are inclusive or open-ended and do not exclude additional, non-recited members, elements or method steps.

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier 'about' refers is itself also specifically, and preferably, disclosed.

As used herein, an 'Alphabody (of the invention)' or 'Alphabodies (of the invention)' can generally be defined as self-folded, single-chain, triple-stranded, predominantly alpha-helical, coiled coil amino acid sequence.

The term 'single-chain' in 'single-chain Alphabody' is therefore redundant, but usually included to emphasize the composition of an Alphabody as a single polypeptide chain, as opposed to the many known occurrences of oligomeric (e.g., trimeric) peptidic coiled coils. More particularly, Alphabodies as used in the context of the present invention can be defined as amino acid sequences, polypeptides or proteins having the general formula HRS1-L1-HRS2-L2-HRS3, wherein each of HRS1, HRS2 and HRS3 is independently a heptad repeat sequence (HRS) consisting of 2 to 7 consecutive heptad repeat units, at least 50% of all heptad a- and d-positions are occupied by isoleucine residues, each HRS starts and ends with an aliphatic or aromatic amino acid residue located at either a heptad a- or d-position, and HRS1, HRS2 and HRS3 together form a triple-stranded, alpha-helical, coiled coil structure; and each of L1 and L2 are independently a linker fragment, covalently connecting HRS1 to HRS2 and HRS2 to HRS3, respectively, and consisting of at least 4 amino acid residues, preferably at least 50% of which are selected from the group proline, glycine, serine.

As used herein, a 'parallel Alphabody' shall have the meaning of an Alphabody (of the invention) wherein the alpha-helices of the triple-stranded, alpha-helical, coiled coil structure together form a parallel coiled coil structure, i.e., a coiled coil wherein all three alpha-helices are parallel.

As used herein, an 'antiparallel Alphabody' shall have the meaning of an Alphabody (of the invention) wherein the alpha-helices of the triple-stranded, alpha-helical, coiled coil structure together form an antiparallel coiled coil structure, i.e., a coiled coil wherein two alpha-helices are parallel and the third alpha-helix is antiparallel with respect to these two helices.

As will become clear from the further description herein the invention also envisages polypeptides comprising a sequence with the general formula HRS1-L1-HRS2-L2-HRS3, but which in certain particular embodiments comprise further groups, moieties and/or residues, which are covalently linked, more particularly N- and/or C-terminal covalently linked, to a basic Alphabody structure having the formula HRS1-L1-HRS2-L2-HRS3. These are referred to herein as the 'Alphabody polypeptides of the invention'.

The terms 'heptad', 'heptad unit' or 'heptad repeat unit' are used interchangeably herein and shall herein have the meaning of a 7-residue (poly)peptide fragment that is repeated two or more times within each heptad repeat sequence of an Alphabody and is represented as 'abcdefg' or 'defgabc', wherein the symbols 'a' to 'g' denote conventional heptad positions. Conventional heptad positions are assigned to specific amino acid residues within a heptad, a heptad unit, or a heptad repeat unit, present in an Alphabody, polypeptide or composition of the invention, for example, by using specialized software such as the COILS method of Lupas et al. (Science 1991, 252:1162-1164; http://www.russell.embl-heidelberg.de/cgi-bin/coils-svr.pl). However, it is noted that the heptads or heptad units as present in an Alphabody are not strictly limited to the above-cited representations (i.e. 'abcdefg' or 'defgabc') as will become clear from the further description herein and in their broadest sense constitute a 7-residue (poly)peptide fragment per se, comprising at least assignable heptad positions a and d.

The terms 'heptad a-positions', 'heptad b-positions', 'heptad c-positions', 'heptad d-positions', 'heptad e-positions', 'heptad f-positions' and 'heptad g-positions' refer respectively to the conventional 'a', 'b', 'c', 'd', 'e', 'f' and 'g' amino acid positions in a heptad, heptad repeat or heptad repeat unit of an Alphabody.

A 'heptad motif' as used herein shall have the meaning of a 7-residue (poly)peptide pattern. A 'heptad motif' of the type 'abcdefg' can usually be represented as 'HPPHPPP', whereas a 'heptad motif' of the type 'defgabc' can usually represented as 'HPPPHPP', wherein the symbol 'H' denotes an apolar or hydrophobic amino acid residue and the symbol 'P' denotes a polar or hydrophilic amino acid residue. However, it is noted that the heptad motifs as present in an Alphabody are not strictly limited to the above-cited representations (i.e. 'abcdefg', 'HPPHPPP', 'defgabc' and 'HPPPHPP') as will become clear from the further description herein.

A 'heptad repeat sequence' ('HRS') as used herein shall have the meaning of an amino acid sequence or sequence fragment consisting of n consecutive heptads, where n is a number equal to or greater than 2.

In the context of the single-chain structure of the Alphabodies (as defined herein) the terms 'linker', 'linker fragment' or 'linker sequence' are used interchangeably herein and refer to an amino acid sequence fragment that is part of the contiguous amino acid sequence of a single-chain (monomeric) Alphabody, and covalently interconnects the HRS sequences of that Alphabody.

In the context of the present invention, a 'coiled coil' or 'coiled coil structure' shall be used interchangeably herein and will be clear to the person skilled in the art based on the common general knowledge and the description and further references cited herein. Particular reference in this regard is made to review papers concerning coiled coil structures, such as for example, Cohen and Parry *Proteins* 1990, 7:1-15; Kohn and Hodges *Trends Biotechnol* 1998, 16:379-389; Schneider et al *Fold Des* 1998, 3:R29-R40; Harbury et al. *Science* 1998, 282:1462-1467; Mason and Arndt *Chem Bio Chem* 2004, 5:170-176; Lupas and Gruber *Adv Protein Chem* 2005, 70:37-78; Woolfson *Adv Protein Chem* 2005, 70:79-112; Parry et al. *J Struct Biol* 2008, 163:258-269; McFarlane et al. *Eur J Pharmacol* 2009, 625:101-107.

An 'alpha-helical part of an Alphabody' shall herein have the meaning of that part of an Alphabody which has an alpha-helical secondary structure. Furthermore, any part of the full part of an Alphabody having an alpha-helical secondary structure is also considered an alpha-helical part of an Alphabody. More particularly, in the context of a binding site, where one or more amino acids located in an alpha-helical part of the Alphabody contribute to the binding site, the binding site is considered to be formed by an alpha-helical part of the Alphabody.

A 'solvent-oriented' or 'solvent-exposed' region of an alpha-helix of an Alphabody shall herein have the meaning of that part on an Alphabody which is directly exposed or which comes directly into contact with the solvent, environment, surroundings or milieu in which it is present. Furthermore, any part of the full part of an Alphabody which is directly exposed or which comes directly into contact with the solvent is also considered a solvent-oriented or solvent-exposed region of an Alphabody. More particularly, in the context of a binding site, where one or more amino acids located in a solvent-oriented part of the Alphabody contribute to the binding site, the binding site is considered to be formed by a solvent-oriented part of the Alphabody.

The term 'groove of an Alphabody' shall herein have the meaning of that part on an Alphabody which corresponds to the concave, groove-like local shape, which is formed by any pair of spatially adjacent alpha-helices within an Alphabody.

As used herein, amino acid residues will be indicated either by their full name or according to the standard three-letter or one-letter amino acid code.

As used herein, the term 'homology' denotes at least primary structure similarity between two macromolecules, particularly between two polypeptides or polynucleotides, from same or different taxons, wherein said similarity is due to shared ancestry. Preferably, homologous polypeptides will also display similarity in secondary or tertiary structure. Hence, the term 'homologues' denotes so-related macromolecules having said primary and optionally, for proteinaceous macromolecules, secondary or tertiary structure similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two Alphabodies, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Two or more Alphabodies, or two or more nucleic acid sequences are said to be 'exactly the same' if they have 100% sequence identity over their entire length.

An Alphabody, polypeptide or composition of the invention is said to 'specifically bind to' a particular target when that Alphabody, polypeptide or composition of the invention has affinity for, specificity for and/or is specifically directed against that target (or for at least one part or fragment thereof).

The 'specificity' of an Alphabody, polypeptide or composition of the invention as used herein can be determined based on affinity and/or avidity. The 'affinity' of an Alphabody, polypeptide or composition of the invention is represented by the equilibrium constant for the dissociation of the Alphabody, polypeptide or composition and the target protein of interest to which it binds. The lower the KD value, the stronger the binding strength between the Alphabody, polypeptide or composition and the target protein of interest to which it binds. Alternatively, the affinity can also be expressed in terms of the affinity constant (KA), which corresponds to 1/KD. The binding affinity of an Alphabody, polypeptide or composition of the invention can be determined in a manner known to the skilled person, depending on the specific target protein of interest.

It is generally known in the art that the KD can be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or M$^{-1}$ s$^{-1}$). A KD value greater than about 1 millimolar is generally considered to indicate non-binding or non-specific binding.

The 'avidity' of an Alphabody, polypeptide or composition of the invention is the measure of the strength of binding between an Alphabody, polypeptide or composition of the invention and the pertinent target protein of interest. Avidity is related to both the affinity between a binding site on the target protein of interest and a binding site on the Alphabody, polypeptide or composition of the invention and the number of pertinent binding sites present on the Alphabody, polypeptide or composition of the invention. Binding affinities, kOff and kOn rates may be determined by means of methods known to the person skilled in the art. These methods include, but are not limited to RIA (radioimmunoassays), ELISA (enzyme-linked immuno-sorbent assays), 'sandwich' immunoassays, immunoradiometric assays, gel diffusion precipitation reactions, immunodiffusion assays, Western blots, precipitation reactions, agglutination assays (e.g. gel agglutination assays, hemagglutination assays, etc.), complement fixation assays, immunofluorescence assays, immunoelectrophoresis assays, isothermal titration calorimetry, surface plasmon resonance, fluorescence-activated cell sorting analysis, etc.

An Alphabody, polypeptide or composition of the invention is said to be 'specific for a first target protein of interest as opposed to a second target protein of interest' when it binds to the first target protein of interest with an affinity that is at least 5 times, such as at least 10 times, such as at least 100 times, and preferably at least 1000 times higher than the affinity with which that Alphabody, polypeptide or composition of the invention binds to the second target protein of interest. Accordingly, in certain embodiments, when an Alphabody, polypeptide or composition is said to be 'specific for' a first target protein of interest as opposed to a second target protein of interest, it may specifically bind to (as defined herein) the first target protein of interest, but not to the second target protein of interest.

An Alphabody, polypeptide or composition of the invention is said to 'have detectable binding affinity for' a protein of interest, when it binds to that protein of interest with an affinity higher than the detection limit of any of the methods including but not limited to RIA (radioimmunoassays), ELISA (enzyme-linked immuno-sorbent assays), 'sandwich' immunoassays, immunoradiometric assays, gel diffusion precipitation reactions, immunodiffusion assays, Western blots, precipitation reactions, agglutination assays (e.g. gel agglutination assays, hemagglutination assays, etc.), complement fixation assays, immunofluorescence assays, immunoelectrophoresis assays, isothermal titration calorimetry, surface plasmon resonance, fluorescence-activated cell sorting analysis, etc.

The 'half-life' of an Alphabody, polypeptide or compound of the invention can generally be defined as the time that is needed for the in vivo serum or plasma concentration of the Alphabody, polypeptide or compound to be reduced by 50%. The in vivo half-life of an Alphabody, compound or polypeptide of the invention can be determined in any manner known to the person skilled in the art, such as by pharmacokinetic analysis. As will be clear to the skilled person, the half-life can be expressed using parameters such as the t½-alpha, t½-beta and the area under the curve (AUC). An increased half-life in vivo is generally characterized by an increase in one or more and preferably in all three of the parameters t½-alpha, t½-beta and the area under the curve (AUC).

As used herein, the terms 'inhibiting', 'reducing' and/or 'preventing' may refer to (the use of) an Alphabody, polypeptide or composition according to the invention that specifically binds to a target protein of interest and inhibits, reduces and/or prevents the interaction between that target protein of interest, and its natural binding partner. The terms 'inhibiting', 'reducing' and/or 'preventing' may also refer to (the use of) an Alphabody, polypeptide or composition according to the invention that specifically binds to a target protein of interest and inhibits, reduces and/or prevents a biological activity of that target protein of interest, as measured using a suitable in vitro, cellular or in vivo assay. Accordingly, 'inhibiting', 'reducing' and/or 'preventing' may also refer to (the use of) an Alphabody, polypeptide or composition according to the invention that specifically binds to a target protein of interest and inhibits, reduces and/or prevents one or more biological or physiological mechanisms, effects, responses, functions pathways or activities in which the target protein of interest is involved. Such an action of the Alphabody, polypeptide or composition according to the invention as an antagonist may be determined in any suitable manner and/or using any suitable (in vitro and usually cellular or in vivo) assay known in the art, depending on the target protein of interest. In this context, the in vitro action of an Alphabody, polypeptide or composition as an antagonist, being determined in any suitable manner and/or using any suitable in vitro assay known in the art, is also referred to herein as 'the detectable in vitro (antagonistic) activity on' a target protein of interest.

As used herein, the terms 'enhancing', 'increasing' and/or 'activating' may refer to (the use of) an Alphabody, polypeptide or composition according to the invention that specifically binds to a target protein of interest and enhances, increases and/or activates the interaction between that target protein of interest, and its natural binding partner. The terms 'enhancing', 'increasing' and/or 'activating' may also refer to (the use of) an Alphabody, polypeptide or composition according to the invention that specifically binds to a target protein of interest and enhances, increases and/or activates a biological activity of that target protein of interest, as measured using a suitable in vitro, cellular or in vivo assay. Accordingly, 'enhancing', 'increasing' and/or 'activating' may also refer to (the use of) an Alphabody, polypeptide or composition according to the invention that specifically binds to a target protein of interest and enhances, increases and/or activates one or more biological or physiological mechanisms, effects, responses, functions pathways or activities in which the target protein of interest is involved. Such an action of the Alphabody, polypeptide or composition according to the invention as an agonist may be determined in any suitable manner and/or using any suitable (in vitro and usually cellular or in vivo) assay known in the art, depending on the target protein of interest.

The inhibiting or antagonizing activity or the enhancing or agonizing activity of an Alphabody, polypeptide or composition of the invention may be reversible or irreversible, but for pharmaceutical and pharmacological applications will typically occur reversibly.

An Alphabody, polypeptide, composition or nucleic acid sequence of the invention is considered to be '(in) essentially isolated (form)' as used herein corresponds to an Alphabody, when it has been extracted or purified from the host cell and/or medium in which it is produced.

In respect of the Alphabodies, polypeptides and (pharmaceutical) compositions, the terms 'binding region', 'binding site' or 'interaction site' present on the Alphabodies, polypeptides or pharmaceutical compositions shall herein have the meaning of a particular site, part, domain or stretch of amino acid residues present on the Alphabodies, polypeptides or pharmaceutical compositions that is responsible for binding to a target molecule. Such binding region essentially consists of specific amino acid residues from the Alphabody which are in contact with the target molecule.

An Alphabody, polypeptide or composition of the invention is said to show 'cross-reactivity' for two different target proteins of interest if it is specific for (as defined herein) both of these different target proteins of interest.

An Alphabody, polypeptide or composition of the invention is said to be 'monovalent' if the Alphabody contains one binding site directed against or specifically binding to a site, determinant, part, domain or stretch of amino acid residues of the target of interest. In cases wherein two or more binding sites of an Alphabody are directed against or specifically bind to the same site, determinant, part, domain or stretch of amino acid residues of the target of interest, the Alphabody is said to be 'bivalent' (in the case of two binding sites on the Alphabody) or 'multivalent' (in the case of more than two binding sites on the Alphabody), such as for example trivalent.

The term 'bispecific' when referring to an Alphabody implies that either a) two or more of the binding sites of an Alphabody are directed against or specifically bind to the same target of interest but not to the same (i.e. to a different) site, determinant, part, domain or stretch of amino acid residues of that target, or b) two or more binding sites of an Alphabody are directed against or specifically bind to different target molecules of interest. The term 'multispecific' is used in the case that more than two binding sites are present on the Alphabody.

Accordingly, a 'bispecific Alphabody' or a 'multi-specific Alphabody' as used herein, shall have the meaning of a single-chain Alphabody of the formula (N-)HRS1-L1-HRS2-L2-HRS3(-C) comprising respectively two or at least two binding sites, wherein these two or more binding sites have a different binding specificity. Thus, an Alphabody is herein considered 'bispecific' or 'multispecific' if respectively two or more than two different binding regions exist in the same, monomeric, single-domain Alphabody.

As used herein, the term 'prevention and/or treatment' comprises preventing and/or treating a certain disease and/or disorder, preventing the onset of a certain disease and/or disorder, slowing down or reversing the progress of a certain disease and/or disorder, preventing or slowing down the onset of one or more symptoms associated with a certain disease and/or disorder, reducing and/or alleviating one or more symptoms associated with a certain disease and/or disorder, reducing the severity and/or the duration of a certain disease and/or disorder, and generally any prophylactic or therapeutic effect of the Alphabodies or polypeptides of the invention that is beneficial to the subject or patient being treated.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The present inventors have identified methods for making (i.e., constructing, producing, generating) single-chain Alphabody libraries [herein referred to as (single-chain) Alphabody libraries of the (present) invention' or 'libraries of the (present) invention'], which libraries comprise different-sequence Alphabody polypeptides. More particularly, the Alphabody libraries of the present invention are essentially random libraries, in that they comprise variegated positions at which essentially random amino acid residues are placed. The libraries of the present invention have the intrinsic potential of yielding good quality Alphabodies or Alphabody polypeptides binding different target proteins of interest.

The present inventors have further considered the usage of randomized Alphabody libraries wherein amino acid sequence variation is introduced within particular, defined regions of an Alphabody. Such particular, defined Alphabody regions essentially correspond to either a groove, a helix surface or a linker fragment within an Alphabody (as herein defined). The corresponding Alphabody libraries are referred to herein as 'groove' libraries, 'helix' (or 'helix surface') libraries or 'linker' (or occasionally 'loop') libraries, respectively.

An important aspect of the invention is the fact that the Alphabody regions that are selected for introducing amino acid sequence variation (i.e., the variegated Alphabody regions) each have their own intrinsic three-dimensional (3-D) shape in a folded Alphabody scaffold structure. For example, an Alphabody groove will intrinsically have an (elongated) concave shape, a helix surface will intrinsically have an (elongated) convex shape, and a linker fragment will intrinsically have a flexible (variable) shape. Alphabodies are unique in this respect, since they are the only scaffold molecules which unite a groove, helix surface and flexible linker fragment (or loop) in one and the same scaffold structure.

In view of this unique feature, the present inventors have considered the construction of Alphabody libraries wherein the introduced sequence variation is not exclusively confined to one particular area. For example, limited sequence variation may be introduced in a helix surface when constructing a linker or loop library. Alternatively, limited sequence variation may be introduced at fully exposed helical residue positions adjacent to the variegated positions in a groove library. Alternatively, limited sequence variegation may be introduced within a linker fragment flanking variegated alpha-helices in either a groove or helix surface library. The said limited sequence variation outside a defined, characteristic area (in combination with sequence variation within a defined, characteristic area such as a groove, helix surface or linker fragment) will be typically restricted to less than 30% of all variegated amino acid residue positions in order to maintain the (concave, convex or variable shape) shape properties of the characteristic area where the vast majority of variegated residue positions are located (typically, at least 70% of all variegated positions will be located within either a groove, a helix surface, or a linker fragment).

The inventors have also found that the Alphabody libraries of the invention can be used for the screening for and/or selection of one or more Alphabodies or Alphabody polypeptides that specifically bind to a target molecule of interest.

It has further been demonstrated that the identified and/or isolated target-binding Alphabodies and Alphabody polypeptides obtained using the Alphabody libraries of the present invention overcome one or more of the disadvantages of target-binding molecules of the prior art. Indeed, it has been found that the target-binding Alphabodies isolated from the libraries of the invention can bind to the target with affinities at least comparable to and often better than traditional binding agents. Moreover, the target-binding Alphabodies that can be selected and isolated from the libraries of the invention maintain the advantages that were initially identified for the basic Alphabody scaffold structure, such as the Alphabody scaffolds provided in WO 2010/066740 and EP 2 161 278, including, but not limited to, a small size (between 10 and 14 kDa), extreme thermostability, high protease resistance, high engineerability (in the sense that multiple substitutions will generally not obliterate their correct and stable folding), and a structure which is based on natural motifs and has been redesigned via protein engineering techniques. Finally, the possibility of using Alphabody scaffold libraries having different intrinsic shapes solves the technical problem of (a lack of) intrinsic shape complementarity between a scaffold library (from which good binders have to be retrieved) and target molecules in general (which may be very diverse in shape). Also, the optional usage of combinations or mixtures of Alphabody libraries of different intrinsic shape may aid in solving the technical problem of (a lack of) intrinsic shape complementarity with a target molecule of interest.

As a main object, the present invention provides single-chain Alphabody libraries. These single-chain Alphabody libraries of the invention are characterized in that they comprise a collection of different-sequence single-chain Alphabody polypeptides.

The different-sequence Alphabody polypeptides comprised in the libraries of the present invention are characterized in that these polypeptides differ from each other in a defined set of variegated amino acid residue positions. Accordingly, the term 'different-sequence' refers to the occurrence of sequence variation or sequence differences in a defined set of amino acid residue positions between two or more Alphabody polypeptides of the libraries of the invention.

A library or collection of Alphabody sequences may contain any suitable number of different Alphabody sequences, such as at least 2, at least 5, at least 10, at least 50, at least 100, at least 1000, at least 10,000, at least $10^5$, at least $10^6$, at least $10^7$, at least $10^8$, at least $10^9$ or more different-sequence (single-chain) Alphabodies.

More particularly, a library or collection of different Alphabody sequences according to the present invention contains at least 100 different-sequence Alphabody polypeptides, such as at least 200, at least 300, at least 400, at least 500, such as at least 1000, at least 10000, at least $10^5$, at least $10^6$, at least $10^7$, at least $10^8$, at least $10^9$ or more sequences.

In particular embodiments, a set, collection or library (as used interchangeably herein) of Alphabody sequences of the present invention contains at least 100 different-sequence Alphabody polypeptides.

In addition, the single-chain Alphabody libraries of the invention are characterized in that the different-sequence single-chain Alphabody polypeptides comprised in those libraries differ from each other in at least one of a defined set of variegated amino acid residue positions.

Accordingly, in particular embodiments, the different Alphabody sequences, also referred to herein as different-sequence (single-chain) Alphabodies, comprised in the libraries of the invention, only differ from each other in a defined, i.e., fixed or predetermined, set of amino acid residue positions.

Such a defined set of variegated amino acid residue positions consists of a number of particular amino acid residue positions, which are characterized by variety or diversity of amino acid residue types when the different-sequence (single-chain) Alphabodies within the produced library are compared to each other.

The notion 'variegated amino acid residue position', when referring to a library of different-sequence Alphabodies, refers to an amino acid residue position at which at least two different amino acid residue types (amino acid residues of a defined type, for example natural amino acid residue types) are located when at least two of the amino acid sequences of the different-sequence Alphabodies from the said library of Alphabodies are compared to each other (note that these positions will not differ for any two different-sequence Alphabodies of the library, but that the library comprises at least two different-sequence Alphabodies which differ in this amino acid residue position). A 'set of variegated amino acid residue positions', when referring to a library of different-sequence Alphabodies, refers to the set of amino acid residue positions at which at least two different amino acid residue types are located when at least two of the amino acid sequences of the different-sequence Alphabodies from the said library of Alphabodies are compared to each other (note that these positions will not differ for any two different-sequence Alphabodies of the library). A 'defined set of variegated amino acid residue positions', when referring to a library of different-sequence Alphabodies, refers to the specific set of amino acid residue positions at which at least two different amino acid residue types are located when all amino acid sequences from the said library of different-sequence Alphabodies are simultaneously compared to each other. Thus, the simultaneous comparison of all amino acid sequences from the said library of different-sequence Alphabodies, and the identification of amino acid residue positions at which at least two different amino acid residue types are located in such simultaneous comparison, allows to identify the said defined set of variegated amino acid residue positions in an Alphabody library. It is herein submitted that a skilled person will known how to determine the sequences in a library of sequences such as a single-chain Alphabody library. It is herein further understood that Alphabody sequences can be compared both at the level of amino acid sequences or nucleotide sequences representing (encoding) these amino acid sequences.

A preferred method to compare two or more different-sequence Alphabodies is based on a pair-wise or multiple sequence alignment, generated by a known computer algorithm for automated sequence alignment such as NCBI Blast. Alternatively, two or more different-sequence Alphabodies can be compared on the basis of a pair-wise or multiple sequence alignment which is generated by a skilled user, such method of alignment also being known as manual sequence alignment. Both of the techniques of automated and manual sequence alignment applied to different-sequence Alphabodies can be based on the maximization of global sequence identity or global sequence similarity (or homology or correspondence), or on the maximization of sequence identity or similarity of the core amino acid positions (i.e., the heptad a- and d-positions as defined herein) of the different-sequence Alphabodies.

Accordingly, a defined set of variegated amino acid residue positions can be deduced from an amino acid or nucleotide sequence comparison of all, or at least a representative subset of all different-sequence Alphabodies in an Alphabody library. It is also acknowledged that, upon generating an Alphabody library, so-called unintended mutations, insertions or deletions may occur. Such unintended mutations, insertions or deletions are nucleotide or amino acid mutations, insertions or deletions that occur at positions which were not intended to be variegated at the time of designing or generating the said Alphabody library. As will be acknowledged by a skilled person, and on condition that the said Alphabody library was generated with state-of-the-art technology, such unintended mutations, insertions or deletions will occur only sporadically and in a scattered fashion (i.e., at different positions) within the Alphabody library sequences. Preferably, such unintended mutations, insertions or deletions will occur at any given position with a frequency of less than 10%, more preferably less than 5%, more preferably less than 2%, 1%, or even less than 1%. Accordingly, unintended mutations, insertions or deletions within an Alphabody library can be identified on the basis of their low frequency as compared to the variability observed at positions showing intended sequence variation. Thus, a preferred method to determine a defined set of variegated amino acid residue positions within an Alphabody library of the invention, without possessing knowledge about the design or production of said library, is by determining the nucleotide or amino acid sequences of at least a representative subset of sequences contained within this library, followed by comparing all determined sequences in a (preferably multiple) alignment, followed by identifying the positions at which sequence variation is observed, followed by identifying the frequencies of the nucleotides or amino acid residue types observed at each variable position, followed by identifying the positions having a mutation, insertion or deletion frequency higher than a given cutoff percentage, wherein this cutoff percentage is set at 10%, 5%, 2%, 1% or even less than 1% such as 0.5%, 0.1% or 0% (in which case all observed variations are included in the defined set of variegated amino acid residue positions. Alternatively, if knowledge about the original design or production of a single-chain Alphabody library is available, then the set of variegated amino acid residue positions is this library is preferably based on said knowledge instead of on the analysis of the library itself. Methods to design single-chain Alphabody libraries, including the selection of variegated positions, are described below.

In the libraries according to the present invention, the number of variegated amino acid residue positions in such a defined set can range from 5 to 20 amino acid residue positions. Thus, a defined set of variegated amino acid residue positions in a library of the invention may comprise 5 to 20, such as 5, 6, 7, 8, 9, 10, 11, 12, 13, 14, 15, 16, 17, 18, 19, or 20, defined variegated amino acid residue positions.

The different-sequence Alphabody polypeptides comprised in a library of the invention can differ from each other in at least one amino acid residue positions of such a defined set of 5 to 20 positions. Thus, for example when the defined set of variegated amino acid residue positions in a library comprises a set of 13 variegated amino acid residue positions, the different-sequence Alphabody polypeptides in the libraries of the invention can differ from each other in 1, 2, 3, 4, 5, 6, 7, 8, 9, 10, 11, 12, or all 13 of these amino acid residue positions. Accordingly, it is clear that the different-sequence Alphabody polypeptide sequences comprised in a library of the invention can be distinguished from each other by the sequence difference(s) present in the defined set of 5 to 20 variegated amino acid residue positions, with the proviso that additional, preferably sporadic, unintended mutations, insertions or deletions may occur at positions other than those of the defined set of variegated positions.

The Alphabody scaffold used as the basis (i.e., as reference or template structure) for the construction of the libraries of the present invention forms a single-chain, 3-stranded alpha-helical coiled coil structure which is represented as HRS1-L1-HRS2-L2-HRS3. The heptad repeat sequences (HRS) 1, 2 and 3 each adopt an alpha-helical conformation and are referred to as (alpha-)helices of the Alphabody. These three helices (being present in an Alphabody) are typically referred to as helices A, B and C, respectively.

Making use of the Alphabody single-chain coiled coil scaffold, different types of Alphabody libraries can be generated, depending on where the set of variegated amino acid residue positions is located within the Alphabody structure. The location of the set of variegated amino acids determines the type and the location of the binding site that is generated on the Alphabodies by application of the methods of the invention. Reference can be made in this context to 'groove libraries' (wherein binding sites are predominantly formed by amino acid residues located in the groove between two of the three helices of the Alphabody), 'helix libraries' (wherein binding sites are predominantly formed by amino acid residues located at the solvent-oriented side of one of the three alpha-helices of the Alphabody), or 'loop libraries' (wherein binding sites are predominantly formed by amino acid residues located in one or more of the Alphabody linker sequences fulfilling the role of a loop).

Libraries wherein the variegated amino acid residue positions are located exclusively (i.e., for 100%) in either a groove, surface or linker of the Alphabody are referred to herein as 'pure groove', 'pure surface', or 'pure loop' libraries. However, as will be detailed herein below, the methods envisage the use of Alphabody libraries, which need not be 'pure' groove, surface or loop libraries.

In particular embodiments of the invention, Alphabody libraries are provided wherein the variegated amino acid residue positions are located predominantly in the groove between two of the three helices of the Alphabody. In these embodiments, in the Alphabodies comprised in a library of the invention, the binding site for binding to a target protein is formed predominantly by amino acid residue positions located in the groove between two of the three alpha-helices of the Alphabody.

Residues implicated in the formation of (the surface of) a groove between two adjacent alpha-helices in an Alphabody are generally located at the heptad e- and g-positions, but some of the more exposed b- and c-positions as well as some of the largely buried core a- and d-positions may also contribute to a groove surface; such will essentially depend on the size of the amino acid side chains placed at these positions.

Depending on the nature of the Alphabodies generated, being folded either as parallel or antiparallel single-chain coiled coils, the positions within the Alphabody sequence which need to be variegated in order to obtain a groove library will vary.

When the two spatially adjacent alpha-helices of the Alphabody (i.e., those between which the groove for binding is located) run parallel, as is the case for all pairs of helices in parallel Alphabodies and for helices A and C in antiparallel Alphabodies, then a binding site located in the groove can be formed by variegation of at least some of the e-residues from a first helix and at least some of the g-residues from a parallel second helix. In addition to these residues, the binding site may optionally further be formed by variegating residues at b-positions in the first helix and/or residues at c-positions in the parallel second helix. Thus, in these embodiments, in order to obtain Alphabodies wherein the binding site is located in a e/g-groove, the variegated amino acid residue positions of the Alphabody libraries used in the generation of target-specific Alphabodies are located at heptad e-positions in a first alpha-helix of the Alphabody polypeptides and at heptad g-positions in a second alpha-helix, parallel to the first alpha-helix, and optionally also at heptad b-positions in the first alpha-helix and/or at heptad c-positions in the second alpha-helix of the Alphabody polypeptides. In particular embodiments of the invention, it is envisaged that Alphabody libraries are provided wherein the variegated amino acid residue positions are predominantly (i.e., for at least 70%) located at heptad e- (and optionally also b-) positions in a first alpha-helix of the Alphabody polypeptides and at heptad g- (and optionally also c-) positions in a second alpha-helix, parallel to the first alpha-helix.

Alternatively or additionally, use can be made of Alphabody scaffolds comprising two spatially adjacent alpha-helices that are positioned antiparallel (if a binding site located in the groove between these antiparallel helices is envisaged). This is typically the case for helices A and B or B and C in antiparallel Alphabodies. In these embodiments, there are typically two possibilities for the type of variegated amino acid residue positions that need to be variegated to ensure that the binding site is formed by the groove between antiparallel helices.

In a first possibility, the groove between two antiparallel helices is formed by at least some of the e-residues from a first helix and at least some of the e-residues from an antiparallel second helix. Thus, in order to obtain a binding site formed within such e/e-groove, at least these amino acid residue positions are variegated. In addition to these residues, such a binding site may optionally further be formed by residues at b-positions in the first helix and/or residues at b-positions in the antiparallel second helix. Thus, in these embodiments, in order to obtain Alphabodies directed against a target protein of interest and wherein the binding site is located in a e/e-groove, the variegated amino acid residue positions are located at heptad e-positions in a first alpha-helix of the Alphabody polypeptides and at heptad e-positions in a second alpha-helix, antiparallel to the first alpha-helix, and optionally also at heptad b-positions in the first alpha-helix and/or at heptad b-positions in the second alpha-helix of the Alphabody polypeptides. In particular embodiments of the of the invention, it is envisaged that Alphabody libraries are provided wherein the variegated amino acid residue positions are predominantly (i.e., for at least 70%) located at heptad e- (and optionally also b-) positions in a first alpha-helix of the Alphabody polypeptides and at heptad e- (and optionally also b-) positions in a second alpha-helix, antiparallel to the first alpha-helix.

In a second possibility, the groove between two antiparallel helices is formed by at least some of the g-residues from a first helix and at least some of the g-residues from an antiparallel second helix. Thus, in order to obtain a binding site formed within such g/g-groove, at least these amino acid residue positions are variegated. In addition to these residues, such a binding site may optionally further be formed by residues at c-positions in the first helix and/or residues at c-positions in the antiparallel second helix. Thus, in these embodiments, in order to obtain Alphabodies wherein the binding site is located in a g/g-groove, the variegated amino acid residue positions are located at heptad g-positions in a first alpha-helix of the Alphabody polypeptides and at heptad g-positions in a second alpha-helix, antiparallel to the first alpha-helix, and optionally also at heptad c-positions in the first alpha-helix and/or at heptad c-positions in the second alpha-helix of the Alphabody polypeptides. In particular embodiments of the of the invention, it is envisaged that Alphabody libraries are provided wherein the variegated amino acid residue positions are predominantly (i.e., for at least 70%) located at heptad g- (and optionally also c-) positions in a first alpha-helix of the Alphabody polypeptides and at heptad g- (and optionally also c-) positions in a second alpha-helix, antiparallel to the first alpha-helix.

Thus, it will be clear that parallel Alphabodies, which have three alpha-helices each oriented parallel to one another, contain three e/g-grooves. Antiparallel Alphabodies, on the other hand, which comprise two alpha-helices that are parallel to each other and one alpha-helix that runs antiparallel, contain one e/g-groove, one e/e-groove and one g/g-groove. Any part of an Alphabody groove is also considered a groove region.

In principle, 'pure' groove libraries are Alphabody libraries characterized in that the variegated amino acid residue positions in such libraries are all located at heptad e- and b- or g- and c-positions in a first alpha-helix of the Alphabody polypeptides and at heptad e- and b- or g- and c-positions in a second alpha-helix of the Alphabody polypeptides. It has been found by the present inventors that Alphabody libraries which are characterized in that the variegated amino acid residue positions in such libraries are not exclusively but only predominantly located at heptad e- and b- or g- and c-positions in a first alpha-helix of the Alphabody polypeptides and at heptad at heptad e- and b- or g- and c-positions in a second alpha-helix of the Alphabody polypeptides, generate more and better target-specific Alphabodies. Accordingly, the methods of the present invention specifically envisage Alphabody libraries wherein the variegated amino acid residue positions in such libraries, are predominantly (i.e., for at least 70%), but not exclusively located at heptad e- and b- or g- and c-positions in a first alpha-helix of the Alphabody polypeptides and at heptad e- and b- or g- and c-positions in a second alpha-helix of the Alphabody polypeptides. In particular embodiments, the variegated amino acid residue positions in the Alphabody libraries used are located for at least 70% at the indicated groove-forming positions. In further particular embodiments, at least one of the variegated amino acid residue positions in the libraries is located outside the positions corresponding to the heptad e- and b- or g- and c-positions in a first alpha-helix of the Alphabody polypeptides and corresponding to the heptad e- and b- or g- and c-positions in a second alpha-helix of the Alphabody polypeptides.

Additionally or alternatively, Alphabody libraries are provided in which the binding site is formed predominantly by the surface of one of the three helices of the Alphabody. Accordingly, in these embodiments, Alphabody libraries are provided in which the variegated amino acid residue positions are located predominantly at the solvent-oriented side of one of the three helices of the Alphabody polypeptides. Such Alphabody libraries are referred to herein as 'helix surface libraries' or 'helix libraries'.

The amino acid residue positions considered to be at the surface of the Alphabody can be located in either helix A, B or C. In particular embodiments, the Alphabody library contains Alphabodies in which the variegated amino acid residues correspond to the fully solvent-exposed amino acid residues of helix C. The most protruding and thus solvent-oriented residues are located at b-, c- and f-positions in each of the alpha-helices of an Alphabody. Thus, in particular embodiments, the Alphabody libraries of the invention comprise variegated amino acid residue positions that are located at heptad b-, c- and f-positions in one alpha-helix of the Alphabody polypeptides.

In principle, 'pure' helix surface libraries are Alphabody libraries characterized in that the variegated amino acid residue positions in such libraries are all located at heptad b-, c- and f-positions in one alpha-helix of the Alphabody polypeptides. It has been found by the present inventors that Alphabody libraries which are characterized in that the variegated amino acid residue positions are not exclusively but only predominantly located at heptad b-, c- and f-positions of an alpha-helix in the Alphabody polypeptides generate more and better target-specific Alphabodies. Accordingly, the present invention specifically envisages Alphabody libraries wherein the variegated amino acid residue positions in such libraries are predominantly (i.e., for at least 70%), but not exclusively located at heptad b-, c- and f-positions of an alpha-helix of the Alphabody polypeptides. In particular embodiments, the variegated amino acid residue positions in the Alphabody libraries used are located for at least 70% at the indicated solvent-exposed positions. In further particular embodiments, at least one of the variegated amino acid residue positions in the libraries is located outside the positions corresponding to the heptad b-, c- and f-positions of an alpha-helix of the Alphabody polypeptides.

Additionally or alternatively, Alphabody libraries are provided in which the binding site on the Alphabodies is formed predominantly by amino acid residue positions located in one of the Alphabody linker sequences interconnecting the alpha-helices. In a parallel Alphabody, the two linkers interconnect distal ends of the coiled coil structure (i.e., they form a link between a helix C-terminus and a helix N-terminus located at the opposite end). In an antiparallel Alphabody, the two linkers interconnect proximal ends of the coiled coil structure (i.e., they form a link between a helix C-terminus and a helix N-terminus located at the same end). In both types of Alphabodies, the linkers are deemed to be conformationally flexible. In addition, the linkers in both types of Alphabodies are also deemed to be flexible with respect to their amino acid sequence. Thus, the linkers in both types of Alphabodies may be subjected to amino acid sequence variation without significant effects on the folding and stability of the Alphabody coiled coil scaffold. Consequently, Alphabody 'loop' or 'linker libraries' are provided wherein sequence variegation is introduced within the amino acid positions of any of the linker fragments in any of the parallel or antiparallel Alphabody types. In particular embodiments, libraries are provided wherein all of the amino acid residue positions of one linker fragment are variegated. In further particular embodiments, a selection of the residue positions located near the middle of a linker fragment are variegated (in order not to interfere with the alpha-helical termini). In further particular embodiments, a selection of residue positions near one of the ends of a linker fragment may be varied; although this increases the risk of interference with the alpha-helical terminus, the Alphabodies will be generally stable enough to tolerate such potential interference. In still further particular embodiments, alternating residue positions over the partial or complete length of the loop sequence may be variegated.

'Pure' linker or loop libraries are Alphabody libraries characterized in that the variegated amino acid residue positions in such libraries, are all located within a linker fragment of the Alphabody polypeptides. It has been found by the present inventors that Alphabody libraries which are characterized in that the variegated amino acid residue positions are not exclusively but only predominantly located at linker positions in the Alphabody polypeptides generate more and better target-specific Alphabodies. Accordingly, the present invention specifically envisages Alphabody libraries wherein the variegated amino acid residue positions in such libraries are predominantly (i.e., for at least 70%), but not exclusively located in one of the linkers of the Alphabody polypeptides. In particular embodiments, the variegated amino acid residue positions in the Alphabody libraries provided are located for at least 70% at positions within one of the Alphabody linker fragments. In further particular embodiments, at least one of the variegated amino acid residue positions in the libraries is located outside the amino acid residue positions of a linker fragment of the Alphabody polypeptides.

As indicated above, in particular embodiments of the methods of the invention, Alphabody libraries are provided which are characterized in that the set of variegated amino acids contains at least one, more particularly two or more amino acid residue positions which are located outside, respectively, a groove, helix surface or linker fragment of an Alphabody such that the binding site is predominantly formed, respectively, by that groove, helix surface or linker fragment. In these embodiments, the percentage of variegated amino acid positions within the groove, helix surface or linker fragment of an Alphabody having a binding site that is predominantly formed by that groove, helix surface or linker fragment, respectively, is less than 100%. However, the percentage of variegated amino acid positions that is located within the groove, helix surface or linker fragment is typically at least 70%.

Thus, in particular embodiments of the present invention, the Alphabody libraries are not pure groove, pure surface or pure loop libraries. More particularly, at least 70% but not all of the variegated amino acid positions, such as for example less than 95%, such as less than 90%, or less than 85% of the variegated amino acid positions are located within either a groove, a helix surface or a linker fragment of the Alphabody.

Depending on the number of amino acid residue positions variegated, the percentages described above will correspond to a different number of actual amino acid residue positions. Accordingly, as will be clear from the above, in particular embodiments of the methods of the invention, Alphabody libraries are provided in which for example at least 5% (i.e., at least 1 position of the 5 to 20 variegated positions), or particularly at least 10% (i.e., at least 1 or at least 2 positions), or particularly at least 15% (i.e., at least 1 to at least 3 positions), or particularly at least 20% (i.e., at least 1 to at least 4 positions), or particularly at least 25% (i.e., at least 2 to at least 5 positions), or particularly 30% (i.e., between 2 and 6 positions) of these 5 to 20 positions are located at positions other than:

- (i) at heptad e- or g-positions in a first alpha-helix of the Alphabody polypeptides and at heptad e- or g-positions in a second alpha-helix, and optionally at heptad b- or c-positions in the first alpha-helix of the Alphabody polypeptides and/or at heptad b- or c-positions in the second alpha-helix of the Alphabody polypeptides, such as
  - (i1) at heptad e-positions in a first alpha-helix of the Alphabody polypeptides and at heptad g-positions in a second alpha-helix, parallel to the first alpha-helix, and optionally at heptad b-positions in the first alpha-helix of the Alphabody polypeptides and/or at heptad c-positions in the second alpha-helix of the Alphabody polypeptides, or
  - (i2) at heptad e-positions in a first alpha-helix of the Alphabody polypeptides and at heptad e-positions in a second alpha-helix, antiparallel to the first alpha-helix, and optionally at heptad b-positions in the first alpha-helix of the Alphabody polypeptides and/or at heptad b-positions in the second alpha-helix of the Alphabody polypeptides, or
  - (i3) at heptad g-positions in a first alpha-helix of the Alphabody polypeptides and at heptad g-positions in a second alpha-helix, antiparallel to the first alpha-helix, and optionally at heptad c-positions in the first alpha-helix of the Alphabody polypeptides and/or at heptad c-positions in the second alpha-helix of the Alphabody polypeptides, or
- (ii) at heptad b-, c- and f-positions in one alpha-helix of the Alphabody polypeptides, or
- (iii) at positions in a linker fragment connecting two consecutive alpha-helices of the Alphabody polypeptides.

Accordingly, the different-sequence (single-chain) Alphabodies in a library differ in a defined set of 5 to 20 amino acid residue positions, wherein, for each library, at least 70% (i.e., at least 4 to at least 14 positions) of these 5 to 20 positions, such as at least 75% (i.e., at least 4 to at least 15 positions), at least 80% (i.e., at least 4 to at least 16 positions), at least 85% (i.e., at least 4 to at least 17 positions), such as at least 90% (i.e., at least 5 to at least 18 positions), for example at least 95% (i.e., at least 5 to at least 19 positions), or more, such as 100% (i.e., all 5 to 20 positions) are located either:

- (i) at a groove formed by or between two adjacent alpha-helices, or
- (ii) at a solvent-oriented surface of one alpha-helix, or
- (iii) within one of the linker fragments interconnecting two alpha-helices, of each the Alphabody polypeptides in the library; more particularly these variegated positions are located at the positions recited for each of the options above.

It is noted that for the Alphabody libraries wherein the variegated amino acid residue positions are located primarily (i.e., at least 70%) in the groove, the remaining variegated positions that are located elsewhere than at the said heptad e-, g-, b- or c-positions may for example be located at heptad a-positions, at heptad d-positions, at heptad f-positions or at amino acid residue positions in the linkers of the Alphabody. The a-positions and d-positions (also referred to as core residues) in each heptad repeat sequence of an Alphabody of the invention are amino acid residue positions of the coiled coil structure which form essentially the solvent-shielded (i.e., buried) part of the Alphabody. It is envisaged that in most Alphabody groove libraries of the present invention, all or some of these core residues are kept conserved in order to maintain the stability of the Alphabodies. In these embodiments, the remaining variegated positions may be located for instance at linker residue positions or heptad f-positions.

Similarly for the Alphabody libraries wherein the variegated amino acid residue positions are located primarily (i.e., at least 70%) at the solvent-oriented surface of an Alphabody helix, the remaining variegated positions that are not located at the said heptad b-, c-, or f-positions may for example be located at heptad e-, g-, a- or d-positions or at amino acid residue positions in the linkers of the Alphabody. As detailed above, it is envisaged that in most Alphabody helix surface libraries according to the present invention, all or some of the core residues (at a- and d-positions) are kept conserved in order to maintain the stability of the Alphabodies. In these embodiments, the remaining variegated positions may be located for instance at heptad e- or g-positions or at linker residue positions.

Finally, for the Alphabody libraries wherein the variegated amino acid residue positions are located primarily (i.e., at least 70%) within a linker fragment of the Alphabody, the remaining variegated positions that are not located within the linker fragment may for example be located at heptad e-, g-, f-, b-, c-, a- or d-positions or at amino acid residue positions in the other of the two linker fragments of the Alphabody. Again, the a-positions and d-positions in each heptad unit of an Alphabody will in some embodiments not be varied to ensure stability. In these embodiments, the remainder of the variegated amino acid residue positions may be located at heptad e-, g-, f-, b-, or c-positions or at amino acid residue positions in the other of the two linker fragments of the Alphabody.

When referring to variegated amino acid residue positions located within the groove formed by or between two adjacent alpha-helices of each of the Alphabody polypeptides, it is meant that these variegated amino acid residue positions are located within one and the same groove, i.e., a groove formed by the two same adjacent alpha-helices, in each of the Alphabody polypeptides comprised in a library. Similarly, when referring to variegated amino acid residue positions located within one alpha-helix of the Alphabody polypeptides, it is meant that these variegated amino acid residue positions are located within one and the same alpha-helix, in each of the Alphabody polypeptides comprised in a library. Also, when referring to variegated amino acid residue positions located at positions within a linker fragment interconnecting two consecutive alpha-helices, it is meant that these variegated amino acid residue positions are located within one and the same linker fragment interconnecting two consecutive alpha-helices in each of the Alphabody polypeptides comprised in a library.

However, it can be envisaged that different groove, surface or loop libraries are combined for use e.g. in the development of Alphabodies against a specific target. More particularly, it can be envisaged that a helix surface library comprising variegated amino acid positions primarily located on the surface of helix C is combined with a helix surface library comprising variegated amino acid positions primarily located on the surface of helix A and/or with a helix surface library comprising variegated amino acid positions primarily located on the surface of helix B. Similarly, it can be envisaged that a groove library comprising variegated amino acid positions primarily located within a e/g-groove is combined with a groove library comprising variegated amino acid positions primarily located within a e/e-groove and/or with a groove library comprising variegated amino acid positions primarily located within a g/g-groove. Similarly, it can be envisaged that a linker library comprising variegated amino acid positions primarily located within a first linker fragment is combined with a linker library comprising variegated amino acid positions primarily located within a second linker fragment. Finally, it can be envisaged that one or more helix surface libraries are combined with one or more groove libraries and/or with one or more linker libraries. A practical way of combining single-chain Alphabody libraries can be accomplished, for example, by mixing different libraries in about equal amounts.

The Alphabody libraries of the present invention can be provided in different forms, and can be but are not limited to protein libraries, nucleic acid libraries, vector libraries or host cell libraries.

In particular embodiments, the libraries of the present invention are libraries of host cells, wherein each host cell comprises maximally one member of a nucleic acid or vector library, each such nucleic acid or vector library member encoding a single-chain Alphabody (polypeptide) of the invention. More particularly, the libraries are libraries of host cells wherein Alphabodies are expressed.

In particular embodiments, the Alphabodies of the library are displayed on the surface of a phage particle, a ribosome, a bacterium, a yeast cell, a mammalian cell or any other suitable (micro)organism, so as to facilitate screening or selection to isolate the desired Alphabody sequences having detectable binding affinity for, or detectable in vitro activity on, the target protein or cell of interest.

Thus, in particular embodiments, the libraries of the invention represent a set or collection of protein sequences and are thus Alphabody protein libraries. The Alphabody members of the library can be presented in the library as separate Alphabody sequences, or can be provided as a mixture of different Alphabody sequences.

In further aspects, the present invention provides nucleic acid and vector libraries, which encode the single-chain Alphabody (polypeptide or protein) libraries of the invention or a mixture of single-chain Alphabody libraries.

In a further aspect, the present invention provides methods for the production of single-chain Alphabody libraries of the invention. Accordingly, these methods comprise producing a polypeptide, nucleic acid or vector library.

It will be understood by the skilled person that the Alphabody libraries of the present invention are typically generated by recombinant DNA techniques. More particularly, libraries of nucleic acid sequences encoding Alphabodies each differing in particular amino acid positions are obtained by site-directed or random mutagenesis of a template sequence. As will be acknowledged by a skilled person, random amino acid residues can be introduced at specific positions in an amino acid sequence by, for example, selecting (introducing) 'NNK' or 'NNS' codons at corresponding positions in the nucleotide sequence encoding said amino acid sequence.

Thus, the generation of a (partially) randomized single-chain Alphabody library requires the (partial) randomization of specific positions within a template or standard or reference Alphabody scaffold sequence. Methods for producing such libraries are known to the skilled person and commercial services are available for generating such libraries. The nucleotide(s) determining the relevant amino acid residues at the positions of interest are mutated in different ways such as to obtain a library of nucleotide sequences encoding different Alphabodies.

In particular embodiments of the present invention, the constant, non-variegated part of the single-chain Alphabody polypeptides that are present in the single-chain Alphabody libraries does not correspond to a naturally occurring protein sequence, and thus the sequence representing the non-variegated part of the scaffold is of non-natural origin. Indeed, typically, the constant, non-variegated part of the Alphabody polypeptides in a library of the invention is an artificial sequence.

A template Alphabody scaffold sequence is the sequence of a reference Alphabody which has been selected on the basis of its (near-) optimal physico-chemical properties. As demonstrated in the examples in WO2010/066740, single-chain Alphabodies generally have a high thermal (i.e., thermodynamic) stability, a high solubility, a high resistance to variations in pH, and, importantly, a high tolerability to amino acid sequence variation. Such single-chain Alphabodies, or other single-chain Alphabodies having suitable physico-chemical properties such as a high tolerability to amino acid sequence variation, can be selected as reference or template Alphabody scaffolds (or scaffold sequences) for the generation of single-chain Alphabody libraries of the present invention.

The variegation envisaged in the libraries of the present invention is envisaged to encompass both naturally occurring and synthetic amino acid residues. However, in particular embodiments of the invention, the variegated amino acid residue positions are exclusively occupied by naturally occurring amino acid types, such as for instance but not limited to natural amino acid types, such as glycine, alanine, proline, asparagine, aspartic acid, glutamine, glutamic acid, histidine, arginine, lysine, threonine, serine, cysteine, leucine, isoleucine, methionine, phenylalanine, tyrosine, tryptophan and valine.

In particular embodiments, the production of an Alphabody polypeptide library of the invention involves the step of producing a nucleic acid or vector library of at least 100 members, wherein each member encodes a polypeptide comprising a single-chain Alphabody and wherein the encoded different-sequence Alphabody polypeptides differ from each other in at least one of a defined set of 5 to 20 variegated amino acid residue positions. In particular embodiments, at least 70% but not all of these variegated amino acid residue positions are located either:
  (i) at heptad e- or g-positions in a first alpha-helix of the Alphabody polypeptides and at heptad e- or g-positions in a second alpha-helix, and optionally at heptad b- or c-positions in the first alpha-helix of the Alphabody polypeptides and/or at heptad b- or c-positions in the second alpha-helix of the Alphabody polypeptides, or
  (ii) at heptad b-, c- and f-positions in one alpha-helix of the Alphabody polypeptides, or
  (iii) at positions in a linker fragment connecting two consecutive alpha-helices of the Alphabody polypeptides.

Upon expression of these Alphabody sequences in host cells, an Alphabody polypeptide library is obtained. The production of a random library can be achieved in different ways, as will be known by the person skilled in the art. In general, the methods for the production of Alphabody libraries of the invention typically comprise the step of transforming or transfecting suitable host cells with a nucleic acid or vector library or an infectious particle which encodes a single-chain Alphabody library. Further, the methods for the production of Alphabody libraries typically comprise a step of culturing said host cells under conditions suitable for the proliferation (multiplication, growth) of said host cells and a culturing step under conditions suitable for the production (expression, synthesis) of the encoded single-chain Alphabodies. The culturing of host cells under conditions suitable for proliferation or expression is typically accomplished in the presence of media comprising components suitable for cell growth or induction of expression. In particular embodiments, the methods for the production of Alphabody libraries of the invention further comprise the step of isolating the produced single-chain Alphabodies form the host cells or medium. It is further noted that expressed Alphabody libraries may, in addition to the different-sequence polypeptides also contain multiple copies of identical polypeptides.

In yet a further aspect, the present invention provides uses of the single-chain Alphabody libraries of the invention for the production of an Alphabody directed against a target protein of interest. More particularly, the invention provides the use of Alphabody libraries or mixtures of single-chain Alphabody libraries of the invention for in vitro display methods such as a phage display, yeast display, bacterial display or mRNA display.

The present invention thus also provides methods for the generation of one or more single-chain Alphabodies having detectable binding affinity for (as defined herein), or having detectable in vitro activity on (as defined herein), such as detectable in vitro antagonistic or agonistic activity on, a target molecule or cell of interest. These methods are based on the concept of random library production and screening for binding to or activity on target molecules of interest.

In order to obtain a target-specific Alphabody, the methods for the generation of a target-specific Alphabody comprise the steps of a) generating a single-chain Alphabody library according to the invention and b) selecting from such a single-chain Alphabody library according to the present invention at least one single-chain Alphabody having detectable binding affinity for, or detectable in vitro activity on, the protein or cell of interest.

Accordingly, the methods for the production of one or more single-chain Alphabodies having detectable binding affinity for a target molecule of interest, or detectable in vitro activity on target proteins or cells of interest according to the invention at least comprise the steps of:
a) producing a single-chain Alphabody library according to the invention or a mixture of single-chain Alphabody libraries according to the invention,
b) selecting one or more single-chain Alphabodies having detectable binding affinity for a target molecule of interest, or detectable in vitro activity on target proteins or cells of interest, and, optionally,
c) isolating the one or more single-chain Alphabodies.

The step of selecting a single-chain Alphabody that specifically binds to or is directed against or has detectable binding affinity for a target molecule or protein of interest can be performed in different ways, such as by way of a method commonly known as a selection method or a by way of a method commonly known as a screening method. Both methods envisage the identification and subsequent isolation (i.e., the selection step) of desirable components (i.e., Alphabody library members) from an original ensemble comprising both desirable and non-desirable components (i.e., an Alphabody library). In the case of a selection method, library members will typically be isolated by a step wherein the desired property is applied to obtain the desired goal; in such case, the desired property is usually restricted to the property of a high affinity for a given target molecule of interest and the desired goal is usually restricted to the isolation of such high-affinity library members from the others. Such method is generally known as an affinity selection method and, in the context of the present invention, such affinity selection method will be applied to a single-chain Alphabody library for the purpose of selecting Alphabodies having a high affinity for a protein of interest or a subdomain or subregion thereof. Alternatively, in the case of a screening method, library members will typically be isolated by a step wherein all library members, or at least a substantial collection of library members, are individually examined with respect to a given desired property, and wherein members having such desired property are retained whereas members not having such desired property are discarded; in such case, and in the context of the present invention, desired properties may relate to either a high affinity for the protein of interest or a subdomain or subregion thereof, or a functional activity, including the inhibition, reduction and/or prevention of the activity of the target protein of interest. Accordingly, it is submitted that the selection step of the methods of the invention may be accomplished by either an (affinity) selection technique or by an affinity-based or activity-based functional screening technique, both techniques resulting in the selection of one or more single-chain Alphabodies having beneficial (favorable, desirable, superior) affinity or activity properties compared to the non-selected Alphabodies of the single-chain Alphabody library of the invention.

Thus, in particular embodiments, the selection step comprises contacting a single-chain Alphabody library of the invention or a mixture of single-chain Alphabody libraries of the invention, with a target molecule of interest and determining binding between the target molecule and an Alphabody present in the library. Specific binding of an Alphabody to a target molecule or protein of interest can be determined in any suitable manner known per se, including, for example biopanning, Scatchard analysis and/or competitive binding assays, such as radioimmunoassays (RIA), enzyme immunoassays (EIA) and sandwich competition assays, and the different variants thereof known in the art.

It is noted that the selection or screening of an Alphabody library may be performed in different ways, and that such methods will be adjusted to the form in which the Alphabody library is provided. Suitable methods, techniques and host organisms for displaying and selecting or screening (a set, collection or library of) variegated polypeptide sequences or nucleotide sequences encoding such variegated polypeptide sequences, and which may be applicable to Alphabodies, are known to the person skilled in the art. Such methods are described, for example, in Georgiou et al. *Nat Biotechnol* 1997, 15:29-34; Wittrup *Curr Opin Biotechnol* 2001, 12:395-399; Lipovsek and Pluckthun *J Immunol Methods* 2004, 290: 51-67; Reiersen et al. *Nucl Acids Res* 2005, 33:e10; Levin and Weiss *Mol BioSyst* 2006, 2:49-57; Bratkovic *Cell Mol Life Sci* 2010, 67:749-767.

In particular embodiments, the Alphabody library of the invention is provided as a phage library and binding Alphabodies are identified by contacting the phage with the labeled target molecule, after which binding phages are retrieved by detection or selective collection of the labeled, bound target.

In particular embodiments biopanning methods are used. In the direct biopanning protocol the target is immobilized on a solid support. Examples of solid support are microtiter plates or tubes (e.g. Maxisorp plates, Maxisorp tubes, Nunc) or magnetic beads (Dynabeads, Invitrogen). The target can either be directly coated on the plastic or the beads (surface activated Dynabeads, e.g. Dynabeads M270 Epoxy, Invitrogen) or via streptavidin when the target is biotinylated (e.g. Dynabeads MyOne Streptavidin T1, Invitrogen). Other tags can be used to capture the targets such as His-tags or alternatively, an antibody directed against the target can also be used to capture the target on the support. These alternative tags are also compatible with the Dynabeads (Dynabeads His-tag isolation and pull down, Invitrogen) and Protein A or Protein G coupled Dynabeads (Dynabeads-Protein A/G, Invitrogen). To immobilize the target on magnetic beads, the recommendations of the manufacturer are followed for each specific bead type.

Additionally a soluble biopanning protocol can be used. This implies that the target is captured on the solid support AFTER incubation with the phage library. The target-phage interaction is performed in solution. To be able to wash away the non-binding phage, the target needs to be immobilized on a solid support. The immobilization of the target in the soluble biopanning method is identical to the immobilization possibilities in the direct biopanning protocols.

In particular embodiments, a biotinylated target is used, whereby phages which display an Alphabody binding to the target are captured with a streptavidin-coated support (e.g. magnetic beads). The technology of phage library display, and the selection by means of a phage display technique may be chosen as a method for high-throughput identification of target-specific binders, because it is one of the most robust and versatile selection techniques available (Scott and Smith Science 1990, 249:386-390; Bratkovic Cell Mol Life Sci 2010, 67:749-767). A major advantage of this technology is the coupling of genotype (i.e., the encapsulated DNA encoding the displayed protein) and phenotype (i.e., the displayed protein such as an Alphabody of the present invention) which allows affinity-based selection from large libraries with millions to trillions of polypeptide variants in a relatively simple in vitro assay.

In cases where an Alphabody polypeptide sequence, comprised in a set, collection or library of Alphabody polypeptide sequences, is displayed on a suitable cell or phage or particle, it is also possible to isolate from said cell or phage or particle, the nucleotide sequence that encodes that Alphabody polypeptide sequence. Then, the nucleotide sequences of the selected Alphabody library members can be determined by a routine sequencing method. Finally, the actual desired Alphabody polypeptide sequence(s) can be obtained by expressing said nucleotide sequence(s) in a host organism under suitable conditions, as known to the person skilled in the art.

The methods of the present invention may further comprise the step of amplifying the at least one single-chain Alphabody having detectable binding affinity for, or detectable in vitro activity on, a target protein or cell of interest. For example, a phage clone displaying a particular single-chain Alphabody, obtained from a selection step of a method of the invention, may be amplified by reinfection of a host bacteria and incubation in a growth medium.

In addition, the obtained Alphabody sequences having detectable binding affinity for, or detectable in vitro activity on, a target protein or cell of interest, may be synthesized as soluble protein construct, optionally after their sequence has been identified.

For instance, the Alphabodies obtained, obtainable or selected by the methods of the present invention can be synthesized using recombinant or chemical synthesis methods known in the art. Also, the Alphabodies obtained, obtainable or selected by the methods of the present invention can be produced by genetic engineering techniques. Thus, methods for synthesizing an Alphabody obtained, obtainable or selected by the methods of the present invention may comprise transforming or infecting a host cell with a nucleic acid or a vector encoding an Alphabody sequence having detectable binding affinity for, or detectable in vitro activity on, a target protein or cell of interest. Accordingly, the Alphabody sequences having detectable binding affinity for, or detectable in vitro activity on, a target protein or cell of interest can be made by recombinant DNA methods. DNA encoding the Alphabodies can be readily synthesized using conventional procedures. Once prepared, the DNA can be introduced into expression vectors, which can then be transformed or transfected into host cells such as E. coli or any suitable expression system, in order to obtain the expression of Alphabodies in the recombinant host cells and/or in the medium in which these recombinant host cells reside.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired Alphabodies may be any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

In particular embodiments of the present invention, the selection steps of the methods for producing one or more single-chain Alphabodies having detectable binding affinity (as defined herein) for a target molecule of interest, may comprise the (further) enrichment of the Alphabody library or the mixture of Alphabody libraries for single-chain Alphabodies having detectable binding affinity for the target molecule of interest by iterative execution of the steps of contacting a target molecule of interest with a single-chain Alphabody library or with a mixture of single-chain Alphabody libraries of the invention and subsequently identifying from the single-chain Alphabody library or mixture of single-chain Alphabody libraries being contacted with the target molecule of interest, the one or more single-chain Alphabodies having detectable binding affinity for the target molecule of interest.

The present invention further provides dedicated Alphabody libraries which can be produced in the context of improving or optimizing the binding specificity and/or efficacy of a target-specific Alphabody obtained using the Alphabody libraries of the invention.

In particular embodiments, the methods for the production of one or more target-binding Alphabodies based on the Alphabody libraries according to the invention described above, may further be followed by steps or methods involving the rationalization of the obtained or produced Alphabody sequences. Such a sequence rationalization process may include the identification or determination of particular amino acid residues, amino acid residue positions, stretches, motifs or patterns that are conserved between or among different Alphabodies directed against (i.e., binding to) a specific target molecule of interest. Accordingly, this rationalization process can be conducted by comparing different Alphabody sequences that have been identified to bind the target protein of interest, and by identifying the sequence conservation between these sequences. Such a process can be optionally supported by or be performed by using techniques for molecular modeling and interactive ligand docking.

The particular amino acid residues, amino acid residue positions, stretches, motifs or patterns that are identified as being conserved between or among different Alphabodies against a specific target molecule of interest may be considered as contributing significantly to the binding or activity of the target-specific Alphabodies.

In particular embodiments, the process of sequence rationalization as described above may further be followed by the creation of a new library of Alphabody sequences, starting from the set of different Alphabody sequences that have been identified as being specific for a target molecule of interest and that have been produced using the methods of the invention. In such embodiments, the positions where the amino acid residues, stretches, motifs or patterns are located that are conserved between or among different target-binding Alphabodies are kept constant, and the Alphabody sequences are varied in a new defined set of variegated amino acid residue positions. In this newly defined set, the variegated positions are located outside the positions where the amino acid residues, stretches, motifs or patterns are located that are conserved between or among different target-binding Alphabodies. The Alphabody libraries so obtained are referred to as 'dedicated libraries' of Alphabodies. These dedicated libraries can then again be screened to identify the best target-binding Alphabody.

Accordingly, the present invention further provides methods for the production of dedicated libraries for a target protein of interest, which methods comprise, in addition to the method steps for generating a target-binding Alphabody described above, after the identification of two or more target-binding Alphabodies from a random library, the steps of:

comparing the produced Alphabody sequences that bind the target protein of interest, identifying the amino acid residues, amino acid residue positions, stretches, motifs or patterns that are conserved between or among these different Alphabody sequences, and:

starting from at least one of the two or more Alphabody sequences compared, producing a dedicated library, wherein the library comprises different Alphabody sequences that are variegated in a set of amino acid positions, which are not the amino acid residues, amino acid residue positions, stretches, motifs or patterns that are conserved between or among the different target-binding Alphabody sequences.

These dedicated libraries can be used to obtain Alphabodies with improved properties. More particularly, this comprises:

selecting and/or identifying from the dedicated library those Alphabody sequences having an improved or optimized binding specificity for and/or in vitro activity on the target molecule or cell of interest, and optionally isolating these Alphabody sequences having an improved or optimized binding specificity for and/or in vitro activity on the target molecule or cell of interest.

It will be understood that the steps involved in the methods for producing a dedicated library and selecting, identifying and isolating Alphabody sequences having an improved or optimized binding specificity for and/or in vitro activity on the target molecule or cell of interest, as described above, may be performed in a similar manner as described for the corresponding steps of the methods for producing target-binding Alphabodies of the invention.

As further described herein, the total number of amino acid residues in an Alphabody of the invention can be in the range of about 50 to about 210, depending mainly on the number of heptads per heptad repeat sequence and the length of the flexible linkers interconnecting the heptad repeat sequences. Parts, fragments, analogs or derivatives of an Alphabody, polypeptide or composition of the invention are not particularly limited as to their length and/or size, as long as such parts, fragments, analogs or derivatives still have the biological function of an Alphabody, polypeptide or composition of the invention from which they are derived and can still be used for the envisaged (pharmacological) purposes.

In a further aspect, the present invention also provides single-chain Alphabodies having detectable binding affinity for a target molecule of interest, or detectable in vitro activity on a target molecule or cell of interest, wherein these single-chain Alphabodies are obtainable by methods involving the Alphabody libraries of the present invention, These target-specific Alphabodies and the polypeptides and compositions comprising these target-specific Alphabodies are also referred to herein as 'Alphabodies of the invention' and 'polypeptides and compositions of the invention', respectively.

Accordingly, the present invention also provides Alphabodies that specifically bind to a target molecule or protein of interest, as well as polypeptides and pharmaceutical compositions that comprise or essentially consist of one or more such Alphabodies and to uses of such Alphabodies, polypeptides or compositions for prophylactic, therapeutic or diagnostic purposes.

Thus, the Alphabodies, polypeptides and compositions of the present invention can be used for the prevention and treatment of diseases and disorders which are mediated by biological pathway(s) in which the target molecule of interest, against which the Alphabodies, polypeptides and/or compositions are directed, is involved.

According to particular embodiments, by binding to one or more particular target molecules of interest, the Alphabodies, polypeptides and pharmaceutical compositions of the present invention can be used to prevent or inhibit the interaction between one or more target molecules of interest and their corresponding receptors or natural binding partners, thereby preventing, inhibiting or reducing the signaling pathways that are mediated by those target molecules of interest and/or modulating the biological pathways and mechanisms in which those target molecules of interest are involved.

Thus, in particular embodiments, the Alphabodies, polypeptides and compositions of the invention, specifically bind to target molecules of interest, and more particularly to the receptor-binding site on those target molecules of interest.

Accordingly, in particular embodiments, the Alphabodies, polypeptides and compositions of the invention are directed against a target molecule of interest. The result of the binding of the Alphabodies to the target molecules of interest can be such that, upon binding to that target molecule of interest, it prevents, reduces or inhibits binding of that target molecule of interest to its receptor or to at least one subunit thereof compared to the binding of the target molecule of interest to its receptor in the absence of such Alphabodies, polypeptides or pharmaceutical compositions of the invention, and this by at least 20%, for example by at least 50%, as at least 70%, at least 80%, at least 90%, at least 95% or more, as determined by a suitable assay known in the art.

Alternatively, the binding of the Alphabodies to the target molecule of interest is such that it still allows the target molecule of interest to bind to its receptor, but prevents, reduces or inhibits the signaling that would be triggered by binding of the target molecule of interest to its receptor or at least one subunit thereof compared to the signaling upon binding of the target molecule of interest to its receptor in the absence of such Alphabodies, polypeptides or pharmaceutical compositions of the invention, and this by at least 20%, for example by at least 50%, as at least 70%, at least 80%, at least 90%, at least 95% or more, as determined by a suitable assay known in the art. In further particular embodiments, the binding of the Alphabodies to the target molecule of interest is such that it prevents, reduces or inhibits activation and/or association of the receptor, and in particular target molecule of interest-mediated association of the receptor (i.e., compared to the target molecule of interest-mediated association of the receptor without the presence of such Alphabodies, polypeptides and compositions of the invention, and this by at least 20%, for example by at least 50%, as at least 70%, at least 80%, at least 90%, at least 95% or more, as determined by a suitable assay known in the art.

In particular embodiments the Alphabody, polypeptide or composition obtained using the libraries of the invention inhibit, reduce and/or prevent the interaction between a target protein of interest and its natural binding partner, or, inhibit, reduce and/or prevent the activity of a target protein of interest, or, inhibit, reduce and/or prevent one or more biological or physiological mechanisms, effects, responses, functions pathways or activities in which the target protein of interest is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of the target protein of interest in the same assay under the same conditions but without using the Alphabody, polypeptide or composition of the invention. In addition, 'inhibiting', 'reducing' and/or 'preventing' may also mean inducing a decrease in affinity, avidity, specificity and/or selectivity of a target protein of interest for one or more of its natural binding partners and/or inducing a decrease in the sensitivity of the target protein of interest for one or more conditions in the medium or surroundings in which the target protein of interest is present (such as pH, ion strength, the presence of co-factors, etc.), compared to the same conditions but without the presence of the Alphabody, polypeptide or composition of the invention. In the context of the present invention, 'inhibiting', 'reducing' and/or 'preventing' may also involve allosteric inhibition, reduction and/or prevention of the activity of a target protein of interest.

As will be known to the skilled person, the above Alphabodies, polypeptides and compositions of the invention will generally act as antagonists of target molecule of interest-mediated signaling, i.e., the signaling that is caused by binding of a target molecule of interest to its receptor, as well as the biological mechanisms and effects that are induced by such signaling.

In certain non-limiting embodiments, an Alphabody, polypeptide or composition according to the invention may specifically bind to a target molecule of interest thereby enhancing, increasing and/or activating the interaction between that target molecule of interest and its receptor. Alternatively, an Alphabody, polypeptide or composition according to the invention may also mimic the natural ligand and directly bind to a receptor and thereby enhance, increase and/or activate the biological function of that receptor. Such an agonizing Alphabody, polypeptide or composition according to the invention may thereby enhance, increase and/or activate the biological activity and/or one or more biological or physiological mechanisms, effects, responses, functions or pathways of that target molecule of interest, as measured using a suitable in vitro, cellular or in vivo assay.

Accordingly, in these particular embodiments, the Alphabodies, polypeptides and pharmaceutical compositions of the present invention can be used to increase one or more specific cellular responses in a subject in which the target molecule of interest to which the one or more of the Alphabodies, polypeptides and compositions of the present invention bind, are involved. Agonistic Alphabodies, polypeptides or pharmaceutical compositions of the invention binding to certain target molecule of interest can, for example, be used to stimulate or enhance one or more immune responses in a subject, e.g., for the prevention and/or treatment of diseases that are characterized by a disturbed immune system or that may occur as a result of having a disturbed immune system.

In a further aspect, the present invention provides polypeptides that comprise or essentially consist of at least one Alphabody of the present invention that specifically binds to a protein of interest (also referred to herein as polypeptides of the invention). The polypeptides of the invention may comprise at least one Alphabody of the present invention and optionally one or more further groups, moieties, residues optionally linked via one or more linkers.

Accordingly, a polypeptide of the invention may optionally contain one or more further groups, moieties or residues for binding to other targets or target proteins of interest. It should be clear that such further groups, residues, moieties and/or binding sites may or may not provide further functionality to the Alphabodies of the invention (and/or to the polypeptide or composition in which it is present) and may or may not modify the properties of the Alphabody of the invention. Such groups, residues, moieties or binding units may also for example be chemical groups which can be biologically and/or pharmacologically active.

These groups, moieties or residues are, in particular embodiments, linked N- or C-terminally to the Alphabody. In particular embodiments however, one or more groups, moieties or residues are linked to the body of the Alphabody, e.g. via coupling to a cysteine in an alpha-helix.

In particular embodiments, the polypeptides of the present invention comprise Alphabodies that have been chemically modified. For example, such a modification may involve the introduction or linkage of one or more functional groups, residues or moieties into or onto the Alphabody of the invention. These groups, residues or moieties may confer one or more desired properties or functionalities to the Alphabody of the invention. Examples of such functional groups will be clear to the skilled person and include, without limitation, a purification tag, a detection tag, a fluorescent tag, a glycan moiety, a PEG moiety.

The introduction or linkage of functional groups to an Alphabody of the invention may also have the effect of an increase in the half-life, the solubility and/or the stability of the Alphabody of the invention, or it may have the effect of a reduction of the toxicity of the Alphabody of the invention, or it may have the effect of the elimination or attenuation of any undesirable side effects of the Alphabody of the invention, and/or it may have the effect of other advantageous properties.

In particular embodiments, the polypeptides of the present invention comprise Alphabodies that have been modified to specifically increase the half-life thereof, for example, by means of PEGylation, by means of the addition of a group or protein or protein domain which binds to or which is a serum protein (such as serum albumin) or, in general, by linkage of the Alphabody to a moiety that increases the half-life of the Alphabody of the invention. Typically, the polypeptides of the invention with increased half-life have a half-life that is at least twice, such as at least three times, such as at least five times, for example at least ten times or more than ten times greater than the half-life of the corresponding Alphabody of the invention lacking the said chemical modification.

A particular modification of the Alphabodies of the invention may comprise the introduction of one or more detectable labels or other signal-generating groups or moieties, depending on the intended use of the labeled Alphabody. Yet a further particular modification may involve the introduction of a chelating group, for example to chelate one or more metals or metallic cations. A particular modification may comprise the introduction of a functional group that is one part of a specific binding pair, such as the biotin-(strept)avidin binding pair. Other potential chemical and enzymatic modifications will be clear to the skilled person.

In particular embodiments, the one or more groups, residues, moieties are linked to the Alphabody via one or more suitable linkers or spacers.

In further particular embodiments, the polypeptides of the invention comprise two or more target-specific Alphabodies. In such particular embodiments, the two or more target-specific Alphabodies may be linked (coupled, concatenated, interconnected, fused) to each other either in a direct or in an indirect way. In embodiments wherein the two or more Alphabodies are directly linked to each other, they are linked without the aid of a spacer or linker fragment or moiety. Alternatively, in embodiments wherein the two or more Alphabodies are indirectly linked to each other, they are linked via a suitable spacer or linker fragment or linker moiety.

In embodiments wherein two or more Alphabodies are directly linked, they may be produced as single-chain fusion constructs (i.e., as single-chain protein constructs wherein two or more Alphabody sequences directly follow each other in a single, contiguous amino acid sequence). Alternatively, direct linkage of Alphabodies may also be accomplished via cysteines forming a disulfide bridge between two Alphabodies (i.e., under suitable conditions, such as oxidizing conditions, two Alphabodies comprising each a free cysteine may react with each other to form a dimer wherein the constituting momomers are covalently linked through a disulfide bridge).

Alternatively, in embodiments wherein two or more Alphabodies are indirectly linked, they may be linked to each other via a suitable spacer or linker fragment or linker moiety. In such embodiments, they may also be produced as single-chain fusion constructs (i.e., as single-chain protein constructs wherein two or more Alphabody sequences follow each other in a single, contiguous amino acid sequence, but wherein the Alphabodies remain separated by the presence of a suitably chosen amino acid sequence fragment acting as a spacer fragment). Alternatively, indirect linkage of Alphabodies may also be accomplished via amino acid side groups or via the Alphabody N- or C-termini. For example, under suitably chosen conditions, two Alphabodies comprising each a free cysteine may react with a homo-bifunctional chemical compound, yielding an Alphabody dimer wherein the constituting Alphabodies are covalently cross-linked through the said homo-bifunctional compound. Analogously, one or more Alphabodies may be cross-linked through any combination of reactive side groups or termini and suitably chosen homo- or heterobifunctional chemical compounds for cross-linking of proteins.

In particular embodiments of linked Alphabodies, the two or more linked Alphabodies can have the same amino acid sequence or different amino acid sequences. The two or more linked Alphabodies can also have the same binding specificity or a different binding specificity. The two or more linked Alphabodies can also have the same binding affinity or a different binding affinity.

Suitable spacers or linkers for use in the coupling of different Alphabodies of the invention will be clear to the skilled person and may generally be any linker or spacer used in the art to link peptides and/or proteins. In particular, such a linker or spacer is suitable for constructing proteins or polypeptides that are intended for pharmaceutical use.

Some particularly suitable linkers or spacers for coupling of Alphabodies in a single-chain amino acid sequence include for example, but are not limited to, polypeptide linkers such as glycine linkers, serine linkers, mixed glycine/serine linkers, glycine- and serine-rich linkers or linkers composed of largely polar polypeptide fragments. Some particularly suitable linkers or spacers for coupling of Alphabodies by chemical cross-linking include for example, but are not limited to, homo-bifunctional chemical cross-linking compounds such as glutaraldehyde, imidoesters such as dimethyl adipimidate (DMA), dimethyl suberimidate (DMS) and dimethyl pimelimidate (DMP) or N-hydroxysuccinimide (NHS) esters such as dithiobis(succinimidylpropionate) (DSP) and dithiobis (sulfosuccinimidylpropionate) (DTSSP). Examples of hetero-bifunctional reagents for cross-linking include, but are not limited to, cross-linkers with one amine-reactive end and a sulfhydryl-reactive moiety at the other end, or with a NHS ester at one end and an SH-reactive group (e.g., a maleimide or pyridyl disulfide) at the other end.

A polypeptide linker or spacer for usage in single-chain concatenated Alphabody constructs may be any suitable (e.g., glycine-rich) amino acid sequence having a length between 1 and 50 amino acids, such as between 1 and 30, and in particular between 1 and 10 amino acid residues. It should be clear that the length, the degree of flexibility and/or other properties of the spacer(s) may have some influence on the properties of the final polypeptide of the invention, including but not limited to the affinity, specificity or avidity for a target protein of interest. It should be clear that when two or more spacers are used in the polypeptides of the invention, these spacers may be the same or different. In the context and disclosure of the present invention, the person skilled in the art will be able to determine the optimal spacers for the purpose of coupling Alphabodies of the invention without any undue experimental burden.

The linked Alphabody polypeptides of the invention can generally be prepared by a method which comprises at least one step of suitably linking the one or more Alphabodies of the invention to the one or more further groups, residues, moieties and/or other Alphabodies of the invention, optionally via the one or more suitable linkers, so as to provide a polypeptide of the invention.

Also, the polypeptides of the present invention can be produced by methods at least comprising the steps of: (i) expressing, in a suitable host cell or expression system, the polypeptide of the invention, and (ii) isolating and/or purifying the polypeptide of the invention. Techniques for performing the above steps are known to the person skilled in the art.

The present invention also encompasses parts, fragments, analogs, mutants, variants, and/or derivatives of the Alphabodies and polypeptides of the invention and/or polypeptides comprising or essentially consisting of one or more of such parts, fragments, analogs, mutants, variants, and/or derivatives.

Such parts, fragments, analogs, mutants, variants, and/or derivatives according to the invention may still be capable of specifically binding to a target molecule of interest. In particular embodiments the invention provides target-binding fragments, variants or derivatives of the Alphabodies of the invention.

It should be noted that the libraries, Alphabodies, polypeptides or compositions of the invention (or of the nucleotide sequences of the invention used to express them) are not naturally occurring proteins (or nucleotide sequences). Typically, the Alphabodies of the invention are recombinant, synthetic or semi-synthetic amino acid sequences, polypeptides or proteins (or nucleotide sequences).

The Alphabodies, polypeptides and compositions provided by the invention can be in essentially isolated form (as defined herein), or alternatively can form part of a polypeptide or composition of the invention, which may comprise or essentially consist of at least one Alphabody of the invention and which may optionally further comprise one or more other groups, moieties or residues (all optionally linked via one or more suitable linkers).

It will be appreciated based on the disclosure herein that for prophylactic, therapeutic and/or diagnostic applications, the Alphabodies, polypeptides and compositions obtainable using the libraries of the invention will in principle be directed against or specifically bind to human target molecules of interest. However, where the Alphabodies, polypeptides and compositions of the invention are intended for veterinary purposes, they will be directed against or specifically bind to target molecules of interest from the species intended to be treated, or they will be at least cross-reactive with target molecules of interest from the species to be treated. Accordingly, Alphabodies, polypeptides and compositions that specifically bind to target molecules of interest from one subject species may or may not show cross-reactivity with target molecules of interest from one or more other subject species. Of course it is envisaged that, in the context of the development of Alphabodies for use in humans or animals, Alphabodies may be developed which bind to target molecules of interest from another species than that which is to be treated for use in research and laboratory testing.

It is also expected that the Alphabodies and polypeptides of the invention may bind to some naturally occurring or synthetic analogs, variants, mutants, alleles, parts and fragments of a target molecule of interest. More particularly, it is expected that the Alphabodies and polypeptides of the invention will bind to at least to those analogs, variants, mutants, alleles, parts and fragments of a target molecule of interest that (still) contain the binding site, part or domain of the (natural/wild-type) target molecule of interest and/or the target molecule of interest to which those Alphabodies and polypeptides bind. In particular embodiments the Alphabodies, polypeptides and compositions that specifically bind to target molecules of interest do not show cross-reactivity with a naturally occurring protein other than the target protein of interest.

In yet a further aspect, the present invention provides nucleic acids encoding the single-chain Alphabodies selected and/or produced by the methods of the invention.

In further aspects, the invention provides nucleic acids encoding single-chain Alphabodies, which are obtainable by the methods according to the invention (also referred to herein as 'nucleic acids or nucleic acid sequences of the invention') as well as vectors and host cells comprising such nucleic acid sequences.

These nucleic acid sequences can also be in the form of a vector or a genetic construct or polynucleotide. The nucleic acid sequences of the invention may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

The genetic constructs of the invention may be DNA or RNA, and are preferably double-stranded DNA. The genetic constructs of the invention may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system). The genetic constructs of the invention may comprise a suitable leader sequence to direct the expressed Alphabody to an intended intracellular or extracellular compartment. For example, the genetic constructs of the invention may be inserted in a suitable vector at a pelB leader sequence site to direct the expressed Alphabody to the bacterial periplasmic space. Also, the vector may be equipped with a suitable promoter system to, for example, optimize the yield of the Alphabody.

In a further aspect, the invention provides vectors comprising nucleic acids encoding single-chain Alphabodies, which are obtainable by the methods according to the invention.

In yet a further aspect, the present invention provides host cells comprising nucleic acids encoding single-chain Alphabodies, which are obtainable by the methods according to the invention or vectors comprising these nucleic acids. Accordingly, a particular embodiment of the invention is a host cell transfected or transformed with a vector comprising the nucleic acid sequence encoding the Alphabodies obtainable by the methods of the invention and which is capable of expressing the Alphabodies. Suitable examples of hosts or host cells for expression of the Alphabodies or polypeptides of the invention will be clear to the skilled person and include any suitable eukaryotic or prokaryotic cell (e.g., bacterial cells such as *E. coli*, yeast cells, mammalian cells, avian cells, amphibian cells, plant cells, fish cells, and insect cells), whether located in vitro or in vivo.

In yet a further aspect, the present invention provides pharmaceutical compositions comprising one or more Alphabodies, polypeptides and/or nucleic acid sequences, which are obtainable by the methods according to the invention and optionally at least one pharmaceutically acceptable carrier (also referred to herein as pharmaceutical compositions of the invention). According to certain particular embodiments, the pharmaceutical compositions of the invention may further optionally comprise at least one other pharmaceutically active compound.

The pharmaceutical compositions of the present invention can be used in the diagnosis, prevention and/or treatment of diseases and disorders associated with a target molecule of interest.

In particular, the present invention provides pharmaceutical compositions comprising Alphabodies and polypeptides of the invention that are suitable for prophylactic, therapeutic and/or diagnostic use in a warm-blooded animal, and in particular in a mammal, and more in particular in a human being.

The present invention also provides pharmaceutical compositions comprising Alphabodies and polypeptides of the invention that can be used for veterinary purposes in the prevention and/or treatment of one or more diseases, disorders or conditions associated with and/or mediated by a target molecule of interest.

Generally, for pharmaceutical use, the polypeptides of the invention may be formulated as a pharmaceutical preparation or compositions comprising at least one Alphabody or polypeptide of the invention and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation. Thus, the Alphabodies, or polypeptides of the invention and/or the compositions comprising the same can for example be administered orally, intraperitoneally, intravenously, subcutaneously, intramuscularly, transdermally, topically, by means of a suppository, by inhalation, again depending on the specific pharmaceutical formulation or composition to be used. The clinician will be able to select a suitable route of administration and a suitable pharmaceutical formulation or composition to be used in such administration.

The pharmaceutical compositions may also contain suitable binders, disintegrating agents, sweetening agents or flavoring agents. Tablets, pills, or capsules may be coated for instance with gelatin, wax or sugar and the like. In addition, the Alphabodies and polypeptides of the invention may be incorporated into sustained-release preparations and devices.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Antibacterial and antifungal agents and the like can optionally be added.

Useful dosages of the Alphabodies and polypeptides of the invention can be determined by determining their in vitro activity, and in vivo activity in animal models. Methods for the extrapolation of effective dosages in mice, and other animals, to humans are known to the skilled person.

The amount of the Alphabodies and polypeptides of the invention required for use in prophylaxis and/or treatment may vary not only with the particular Alphabody or polypeptide selected but also with the route of administration, the nature of the condition being treated and the age and condition of the patient and will be ultimately at the discretion of the attendant physician or clinician. Also the dosage of the Alphabodies and polypeptides of the invention may vary depending on the target cell, tumor, tissue, graft, or organ, or the plasma concentration of the target molecule.

The Alphabodies or polypeptides of the invention and/or the compositions comprising the same are administered according to a regimen of treatment that is suitable for preventing and/or treating the disease or disorder to be prevented or treated. The clinician will generally be able to determine a suitable treatment regimen. Generally, the treatment regimen will comprise the administration of one or more Alphabodies and/or polypeptides of the invention, or of one or more compositions comprising the same, in one or more pharmaceutically effective amounts or doses.

The desired dose may conveniently be presented in a single dose or as divided doses (which can again be sub-dosed) administered at appropriate intervals. An administration regimen could include long-term (i.e., at least two weeks, and for example several months or years) or daily treatment.

The Alphabodies and polypeptides of the present invention will be administered in an amount which will be determined by the medical practitioner based inter alia on the severity of the condition and the patient to be treated. Typically, for each disease indication an optical dosage will be determined specifying the amount to be administered per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

In particular, the Alphabodies and polypeptides of the invention may be used in combination with other pharmaceutically active compounds or principles that are or can be used for the prevention and/or treatment of the diseases and disorders in which the target molecule of interest is involved, as a result of which a synergistic effect may or may not be obtained. Examples of such compounds and principles, as well as routes, methods and pharmaceutical formulations or compositions for administering them will be clear to the clinician.

According to a further aspect, the present invention provides the use of Alphabodies or polypeptides of the invention that specifically bind to a target molecule of interest for the preparation of a medicament for the prevention and/or treatment of at least one target molecule of interest-mediated disease and/or disorder in which the target molecule of interest is involved. Accordingly, the invention provides Alphabodies, polypeptides and pharmaceutical compositions specifically binding to a target molecule of interest for use in the prevention and/or treatment of at least one target molecule of interest-mediated disease and/or disorder in which said target molecule of interest are involved. In particular embodiments, the present invention also provides methods for the prevention and/or treatment of at least one target molecule of interest-mediated disease and/or disorder, comprising administering to a subject in need thereof, a pharmaceutically active amount of one or more Alphabodies, polypeptides and/or pharmaceutical compositions of the invention. In particular, the pharmaceutically active amount may be an amount that is sufficient (to create a level of the Alphabody or polypeptide in circulation) to inhibit, prevent or decrease the biological activity and/or the biological pathways or signaling in which target molecules of interest are involved.

The subject or patient to be treated with the Alphabodies or polypeptides of the invention may be any warm-blooded animal, but is in particular a mammal, and more in particular a human suffering from, or at risk of, diseases and disorders in which the target molecule of interest to which the Alphabodies or polypeptides of the invention specifically bind to are involved.

The efficacy of the Alphabodies and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person. Depending on the target molecules of interest involved, the skilled person will generally be able to select a suitable in vitro assay, cellular assay or animal model to test the Alphabodies and polypeptides of the invention for their capacity to affect the activity of these target molecules of interest, and/or the biological mechanisms in which these are involved; and for their therapeutic and/or prophylactic effect in respect of one or more diseases and disorders that are associated with a target molecule of interest.

BRIEF DESCRIPTION OF THE DRAWINGS

The invention will now be further described by means of the following non-limiting Examples and Figures, in which the FIGURES show:

FIG. 2. Illustration of the amino acid sequences of single-chain Alphabody scAB013_L16. The full amino acid sequence in single-letter code is listed at the bottom, to the right of the label 'Full'. Specific segments within the same sequence are also shown on top, to facilitate identification of N- and C-terminal flanking segments (labeled 'N' and 'C', respectively), linker segments (labeled and 'L2', respectively) and the actual heptad repeat sequences (labeled 'HRS1', 'HRS2' and 'HRS3'). Heptad a- and d-positions are provided at the top row to facilitate their identification within the heptad repeat sequences.

FIG. 3. Illustration of single-chain Alphabody libraries. Three Alphabody libraries are shown, each being C-terminally connected to the N-terminus of the phage coat protein pIII. The name of each library is indicated at the top row of each of the three panels ('scLib_AC11', 'scLib_C9' and 'scLib_C7'). Their full amino acid sequences are listed (in single-letter notation) at the bottom of each table panel, to the right of the label 'Full'. The symbol 'x' is used at positions that are randomized. 'PIII' denotes the phage pIII coat protein. Specific segments within the same sequences are also shown on top, to facilitate identification of N- and C-terminal flanking segments (labeled 'N' and 'C', respectively), linker segments (labeled 'L1' and 'L2', respectively) and the actual heptad repeat sequences (labeled 'HRS1', 'HRS2' and 'HRS3'). Heptad a- and d-positions are provided at the top row to facilitate their identification within the heptad repeat sequences.

FIG. 4. Illustration of additional single-chain Alphabody libraries. The name of each library is indicated at the top row of each of the three panels ('scLib_AC11b', 'scLib_AC12' and 'scLib_B10'). The notations, symbols and formatting are the same as in FIG. 3. Some amino acid residue positions are indicated with gray background to highlight the differences in variegated positions with respect to the libraries from which they were derived (scLib_AC12 compared to scLib_AC11 and scLib_B10 compared to scLib_C9).

FIG. 8. Table 3: Multiple alignment of 77 Alphabody sequences resulting from the AC12 library against IL-23

EXAMPLES

Example 1

Generation of Single-Chain Alphabody Libraries

The present example demonstrates that single-chain Alphabody libraries can be obtained which are well-displayed on phage and which are potentially useful for obtaining single-chain Alphabody sequences that bind to a target protein of interest.

Figure 1:
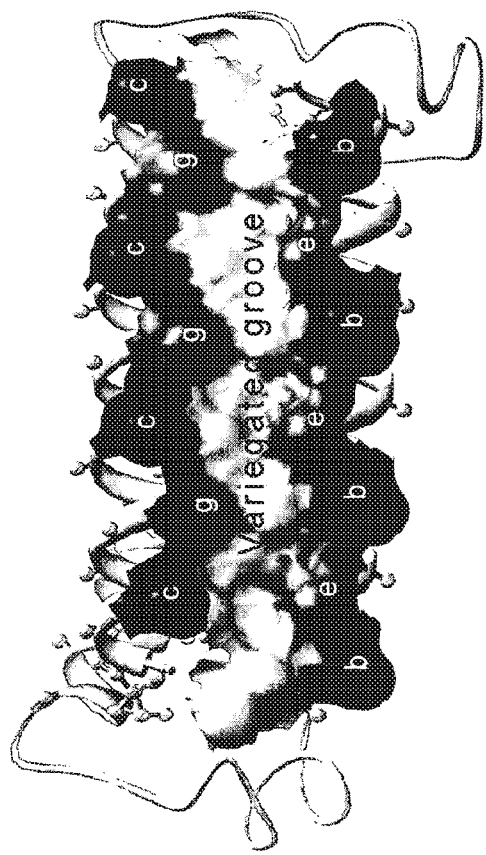
FIG. 1. Illustration of Alphabody groove. The drawing shows a simplified representation of a single-chain Alphabody of the same dimensions as the 'scAB013_L16' Alphabody described herein. All amino acid residues are depicted as alanines (C-beta atoms only). The backbone trace is shown in ribbon representation. Primary, secondary and core groove positions (as defined herein) are surface-rendered to illustrate the location and shape of a groove. The c- and g-residues from one alpha-helix (the A-helix in library scLib_AC11) and the b- and e-residues from a second alpha-helix (the C-helix in library scLib_AC11) are labeled accordingly.

A single-chain Alphabody random library was designed starting from the annotated amino acid sequence and a 3-D model of a reference Alphabody denoted 'scAB013_L16'. A simplified 3-D model of this reference Alphabody is illustrated in FIG. 1. The amino acid sequence of scAB013_L16 is also provided herein as SEQ ID No: 1. The sequence is further shown in FIG. 2, wherein the conventional heptad core positions are indicated as well.

An Alphabody groove is formed by two spatially adjacent alpha-helices of a folded Alphabody protein (FIG. 1). Such groove is characterized by an (elongated) concave shape. Since there are three alpha-helices per Alphabody, there are in principle three candidate grooves which can be randomized. The said 3-D model was inspected first to select the most suitable groove for randomization. It was decided to select the groove between the first alpha-helix ('A-helix') and third alpha-helix ('C-helix'), which run parallel in the 3-D model. Next, the model was further inspected to identify the most suitable amino acid residue positions to be randomized (variegated, varied) in each alpha-helix. It was observed that the groove is actually formed by residues located at heptad c- and g-positions in the A-helix and at heptad b- and e-positions in the C-helix. The g- and e-positions were found to contribute the most (i.e., most directly) to the groove, and are therefore denoted 'primary groove positions'. The c- and b-positions are located somewhat remotely from the middle of the groove, and are therefore denoted 'secondary groove positions'. In addition to these primary and secondary groove positions, the bottom of a groove is formed by some core (a- and d-) positions; in particular, the model showed that core d-positions of the A-helix and a-positions of the C-helix might contribute to the shape of the groove as well, especially if the primary groove positions are occupied by tiny amino acid residues such as glycine, alanine or serine. Such core a- and d-positions which may conditionally contribute to the shape of a groove are herein denoted 'core groove positions'.

FIG. 1 shows that there are 3 primary e- and also 3 primary g-positions within the coiled coil part of the scAB013_L16 Alphabody model. It is further seen that there are 4 b- and 4 c-positions at secondary groove positions. Further, there are 4 core d- and 4 core e-positions which may potentially contribute to the groove. Thus, there are in total 22 positions which can influence the shape of a groove when being variegated. When all 22 would be fully randomized into the 20 natural amino acid residues, this would correspond to a sequence space (i.e., the total number of possible combinations) of $20^{22}$ or about $4 \times 10^{28}$ distinct sequences. Clearly such huge libraries cannot be made in a form wherein all different sequences are physically present (i.e., such library cannot be 'complete'). Consequently, and if the envisaged library is aimed to be complete (or nearly complete), then the number of variable positions should be drastically reduced.

It was therefore decided not to vary any of the core groove positions. This decision was further motivated by the (avoidance of) risks associated with mutating core positions in a coiled coil: many such substitutions would be detrimental for the stability and/or correct folding of the respective Alphabody constructs. Further, it was also decided not to vary two secondary groove positions. In particular, the first c-position in the A-helix and the first b-position in the C-helix were kept constant. Finally, the first primary groove e-position in the C-helix was also kept fixed as well. This resulted in the selection of 11 variegated positions within the context of the reference Alphabody scAB013_L16. The theoretic sequence space of such library, when fully randomized, is thus $20^{11}$ or about $2 \times 10^{14}$ distinct sequences.

In addition to the variegated positions, two other types of modifications to the reference Alphabody scAB013_L16 were made. First, two lysine to glutamic acid mutations were introduced, i.e., one such mutation at the f-position of the second heptad in each of helices A and C. Second, two arginine to alanine mutations were introduced, i.e., one such mutation at the c-position of the fourth heptad in each of helices B and C. The sequence of this modified single-chain Alphabody, wherein positions to be variegated are indicated by 'x'-symbols, is shown in FIG. 3. This sequence is also provided as SEQ ID No: 2. The single-chain Alphabody library that was constructed on the basis of this design is hereinafter referred to as 'scLib_AC11'. Since all variegated positions are located in an Alphabody groove, this library is also referred to as a 'pure groove library'.

A second single-chain Alphabody pure groove library was designed starting from a 3-D model of a smaller Alphabody reference construct denoted 'scAB140_L14'. The latter essentially corresponds to the scAB013_L16 construct wherein the third heptad in each of the alpha-helices is deleted, the glycine/serine linker sequences are reduced from 16 to 14 residues, and the N-terminal alpha-helix capping residues are substituted by an alternative, less negatively charged, motif. Apart from these differences, exactly the same choices with respect to primary, secondary and core groove positions to be variegated were made when designing the library. In view of the deletion of one heptad unit in each of the helices, this library comprises only 7 variable residue positions. The theoretic sequence space for full randomization is therefore $20^7$ or about $10^9$, which should guarantee near-completeness of the actual produced library. The sequence of this single-chain Alphabody groove library, denoted 'scLib_AC7', is shown in FIG. 3. This sequence is also provided as SEQ ID No: 3.

A third single-chain Alphabody pure groove library was designed which was actually a revision of the scLib_AC11 library. This library, denoted 'scLib_AC11b', comprised the same (eleven) variegated groove residue positions, but some modifications were made within the N-terminal helix capping regions and within the linker regions. First, the methionines preceding the alpha-helical heptad repeat sequences were mutated into glycine. The reason for these mutations is that these methionines fulfill a helix capping role and that the 3-D model used for the construction of the scLib_AC11 library indicates that they lie in the grooves; such location in a groove may form a steric obstruction to ligands occupying the groove, and therefore they were replaced by the smallest possible and structurally more flexible amino acid residue type, i.e., glycine. In addition, the glutamic acids at the c-positions in the first heptad of each alpha-helix were substituted into glutamines in order to reduce the negative charges at the N-terminal ends of each helix and, thus, the potential electrostatic bias resulting from such negative charges. Third, the distribution of glycines and serines in the linker fragments was altered in order to reduce the repetitive character. The sequence of the scLib_AC11b library is shown in FIG. 4 and is also provided as SEQ ID No: 4.

A fourth single-chain Alphabody library was designed to explore the potential of generating Alphabodies that bind to their target via a solvent-exposed area on a single alpha-helix. Such solvent-exposed alpha-helical region is characterized by an (elongated) convex shape. In other words, the purpose of this design was to generate an Alphabody 'helix library' (as opposed to the scLib_AC11 and scLib_AC7 libraries which are groove libraries) wherein sequence variegation is introduced within a convex, solvent-oriented area of a single Alphabody helix. The 3-D model of scAB013_L16 was again used as the template structure for guiding the selection of positions to be variegated. It was decided to select the C-helix in this structure as the one to be variegated. Further inspection of the model shows that the b-, c- and f-positions together form a contiguous rim with an (elongated) convex shape. There are 11 such surface positions discernible in this alpha-helix. It was observed that, in principle, some flanking e- and g-positions might potentially aid in the formation of a contiguous binding surface, but this option was discarded in view of the risk to destabilize the Alphabodies and because the number of variable positions would run up too much. Thus, all 11 b-, c- and f-positions in the C-helix were initially considered for variegation, but the two N-terminal glutamates were finally left unaltered in order not to cancel out their capping function and to maintain the library completeness within reasonable bounds. This finally resulted in 9 b-, c- and f-positions to be variegated in the library. This library was accordingly termed 'scLib_C9'. Since all variegated residue positions are located at fully solvent-exposed residue positions in a single alpha-helix, this library is an example of a 'pure helix (surface) library'. The sequence of this library is shown in FIG. 3. This sequence is also provided as SEQ ID No: 5.

A fifth single-chain Alphabody library was designed to examine the potential of Alphabody libraries comprising sequence variation which is not exclusively confined to a groove. Such 'non-pure groove library' was designed to check whether variegated residue positions outside a groove, yet immediately flanking this groove region, would also contribute in a favorable sense to the discovery of specific target-binding Alphabodies. This strategy was further motivated by the fact that such extensions of variegation outside a groove would give rise to variegated surface areas having intrinsic conformational shapes different from an elongated groove shape. Alphabodies contained in a library comprising extended variegated surfaces might potentially bind to shape-complementary epitopes (surface regions) on a target molecule of interest which are different from those which optimally fit a pure groove. Thus, such extended libraries were designed to check whether they would be intrinsically better suited to address (i.e., generate binders to) target molecules (and surface areas thereon) of diverse shape. A concrete design of such library was made, starting from the scLib_AC11 library and again using the said scAB013_L16 Alphabody model. A first modification involved the reduction of the length of the linker fragments (both linkers were shortened by 8 residues). Concerning the variable positions, one secondary groove position (at position c in the fourth heptad of helix A) was no longer variegated but kept fixed as alanine. In helix C, two non-groove f-positions were selected to be variegated in addition to the groove positions that are variegated in the scLib_AC11 library (these non-groove positions are at the f-positions of both the second and third heptad of helix C). The model indicated that the new selection of 12 variegated residue positions results in a more condensed, 'patch-like' variable surface; the intrinsic shape of this surface is less elongated and broader compared to that of a pure groove library, and the concave area is appended by a small convex subarea formed mainly by the newly selected f-positions. This library was accordingly termed 'scLib_AC12'. The sequence of this library is shown in FIG. 4 and is also provided as SEQ ID No: 6.

A sixth single-chain Alphabody library was designed to examine the potential of Alphabody libraries comprising sequence variation which is not exclusively confined to a single helix surface. Such 'non-pure helix library' was designed to check whether variegated residue positions outside a helix surface, yet immediately flanking this helix surface region, would also contribute in a favorable sense to the discovery of specific target-binding Alphabodies. Again, this strategy was motivated by the fact that such extensions of variegation outside a helical surface would give rise to variegated surface areas having intrinsic conformational shapes different from an elongated rim of helix surface residues. Alphabodies contained in a such library might potentially bind to shape-complementary epitopes on a target molecule of interest which are different from those which optimally fit a single helix. Thus, such extended libraries were designed to check whether they would be intrinsically better suited to address target molecules (and surface areas thereon) of diverse shape. A concrete design of such library was made, starting from the scLib_C9 library and again using the said scAB013_L16 Alphabody model. A first modification involved the selection of the linker fragments, which were chosen identical to those in the scLib_AC11b library. A second modification involved the selection of the helix to be randomized: here it was opted to introduce sequence variation in the B-helix instead of the C-helix as in the scLib_C9. Concerning the actual selection of variable positions, two previously modified, topologically equivalent helix surface positions were kept constant (positions f and b in the first and second heptad of helix B were kept fixed as lysine and alanine, respectively). Then, two groove g-positions in the B-helix were selected to be variegated in addition to the helix surface positions that are variegated in the C-helix of scLib_C9 (these groove positions are at the g-positions of both the second and third heptad of helix B). Finally, the model suggested that a C-helix position (at the g-position in the first heptad of the C-helix) would directly adjoin the other variegated positions, and this position was therefore kept variable as well. In summary, the model indicated that the new selection of 10 variegated residue positions results in a more condensed, 'patch-like' variable surface; the intrinsic shape of this surface is less elongated and broader compared to that of a pure helix surface library, and the convex area is appended by a small concave subarea formed mainly by the newly selected groove g-positions. This library was accordingly termed 'scLib_B10'. The sequence of this library is shown in FIG. 4 and is also provided as SEQ ID No: 7.

Figure 5:
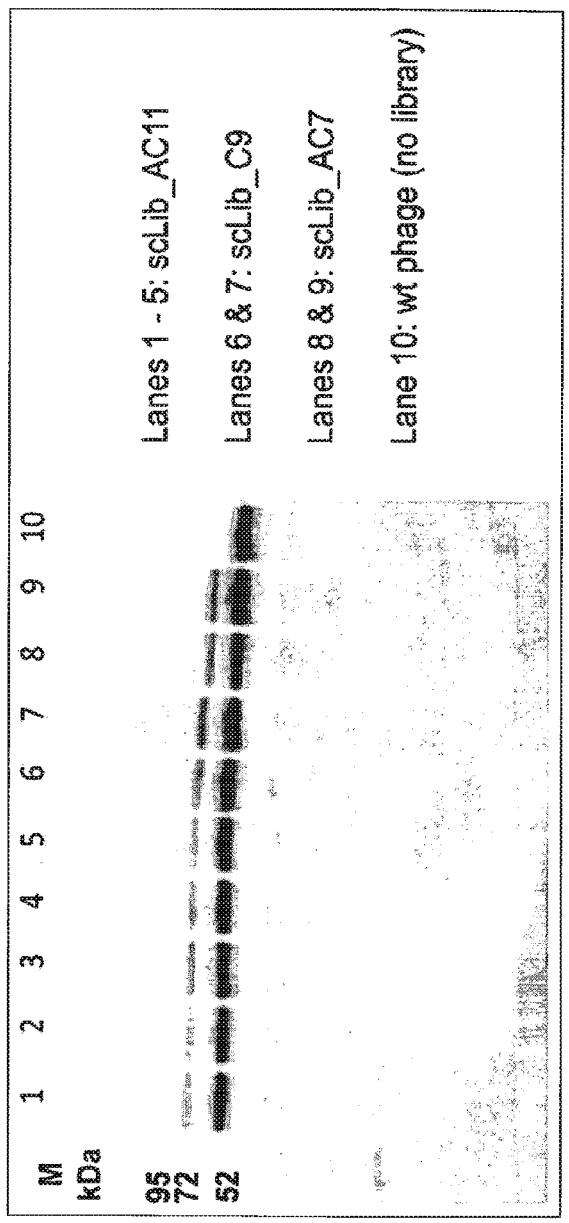
FIG. 5. Western-Blot analysis of Alphabody library phages. In each lane, $2 \times 10^{11}$ phages were applied. Several batches of phages from each library were tested. Samples were blotted onto nitrocellulose membrane after SDS-PAGE in reducing conditions. The presence of the fusion product was demonstrated by using a mouse anti-gpIII antibody followed by an AP-anti-mouse conjugate and the blot was developed by adding the NBT-BCIP substrate.

The actual single-chain Alphabody libraries were ordered at Geneart AG (Regensburg, Germany). A '3+3' monovalent display format (Smith, Gene 128:1-2(1993)) was adopted using the pCx1 vector, a pHEN-derived phagemid. The libraries scLib_AC11, scLib_AC7 and scLib_C9 were delivered as transformed E. coli TG1cells with a guaranteed minimum of 108 unique clones. The libraries scLib_AC11b, scLib_AC12 and scLib_B10 were delivered with a guaranteed minimum of 109 unique clones. The Alphabody sequences were fused to the pill coat protein of M13 phages. They were attached via their C-terminus to the pill coat protein through a linker sequence that contains an amber codon (at the genetic level) and a His6-tag (SEQ ID NO: 86). Exportation of the fused Alphabodies to the periplasm was ensured by the presence of a PelB leader sequence at the N-terminus The level of display on phage was checked using Western-Blotting and was found to be suitably high. Analysis showed that in general one third of the phages displayed an Alphabody (FIG. 5).

Example 2

Use of the Alphabody Libraries of the Invention for the Generation of Target-Specific Alphabodies Using the Alphabody libraries such as those described above, binders for human IL-23 were generated. Interleukin-23 (IL-23) is a heterodimeric cytokine consisting of two subunits, p40 consisting of 3 domains, each formed by beta-strands and another p19 which has a four-helix bundle organization. The p40 subunit is also found in IL-12. Accordingly, the biopanning protocol was slightly adjusted to further the selection of Alphabodies binding the P19 subunit, in order to obtain Alphabodies specific for IL-23.

Libraries

The phage libraries scLib_AC12 and scLib_B10 obtained as described in Example 1 were used. These phage libraries displayed the randomized Alphabody sequences as fusion proteins with the viral pIII protein.

The scLib B10 is a helix library, while scLib AC12 is a groove library.

Figure 7:
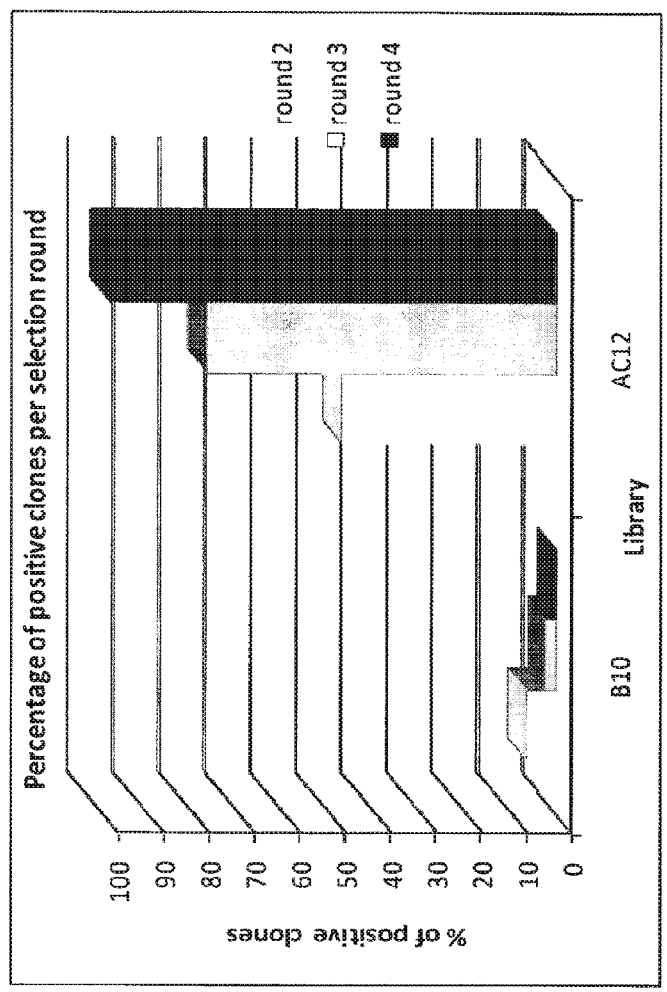
FIG. 7. Percentage of positive clones in the successive biopanning rounds of library scLib_B10, noted as B10 and scLib_AC12, noted as AC12.

The definition of the libraries is shown in FIG. 7.

Rescue of the phage libraries*PLEASE CONSIDER TO WHAT EXTENT WE REALLY HAVE TO PROVIDE ALL THIS DETAIL. IS THIS NOT COMMON GENERAL KNOWLEDGE+KNOW HOW?*

The inoculums (0.608 ml and 1.157 ml, of respectively) of the library stock were transferred to the calculated volume (respectively 933 and 1466 ml) of growth medium consisting of 2×TY supplemented with 0.1 mg/ml ampicillin and 2% of glucose (2×TY-AG). The bacterial cultures were grown at 37° C. with shaking (300 rpm) in baffle flasks to reach an OD600 nm of 0.5 (mid-log phase). The bacterial culture was used for superinfection with helper phage M13K07 (GE Healthcare) to produce phage particles. The ratio helper phage/bacteria applied for the superinfection was 20:1.

The infection culture was incubated at 37° C. for 30 min without shaking to allow infection of the bacteria. After incubation, a sample of the infection culture was taken for titration on 2×TY-AG agar plates and 2×TY-AGK agar plates (K standing for kanamycin (25 microgram/ml) since helper phage are kanamycin resistant) to determine the number of viable and infected bacteria, respectively. The infection culture was then incubated for an additional 30 min, at 37° C. with shaking.

After incubation, bacterial cell pellets were obtained by centrifugation of the cultures at 4000 rpm for 10 min at room temperature. The bacterial pellets were resuspended in the same volume of pre-warmed 2×TY-AK medium as the initial start volume. Cultures were grown overnight at 30° C. with shaking (300 rmp).

After overnight incubation, a sample of the culture was taken for titration on 2×TY-AGK agar plates to determine viable cells. The cultures were cooled for 5 min on ice and bacteria were pelleted at 7000 rpm for 20 min. The supernatant was collected to precipitate phage by adding ⅕th of the volume of a solution of 20% PEG 4000/2.5 M NaCl and incubated 1 to 2 hours on ice. After incubation phage were recovered by centrifugation at 4° C., 7000 rpm for 20 min. Phage pellet was solved in 35 ml Phosphate Buffered Saline (PBS)/900 ml of bacterial culture and bacterial debris was removed by centrifugation at 12000 rpm, 10 min. A second PEG/NaCl precipitation was performed for 1 hr followed by removal of bacterial debris. Finally, purified phage corresponding to the library were obtained (10 ml/900 ml initial bacterial culture). 15% of glycerol was added to the phage to store at −80° C.

The titer of the phage preparation corresponding to the library was determined by infecting bacteria (*E. coli* TG1 strain) with serial dilutions of purified phage and plating out these dilutions on 2×TY-AG agar plates. This titration allowed to determine the number of infectious phage particles (colony forming units (cfu) or transducing units (TU)). Although the libraries were provided as transformed *E. coli* ER 2738 bacteria, all further phage propagations were performed using a *E. coli* TG1 strain (Stratagene), a common strain used in phage display technology.

The expression of Alphabodies was evaluated in Western Blot analysis using an anti-pIII antibody to determine the presence of wild type pIII protein and the Alphabody fusion pIII protein. The molecular weight of the fusion pIII protein is higher than the wild type pIII protein and will thus migrate slower in the SDS-PAGE gel. When fusion protein is present, two bands should be visualized using the anti-pIII antibody.

Figure 6:
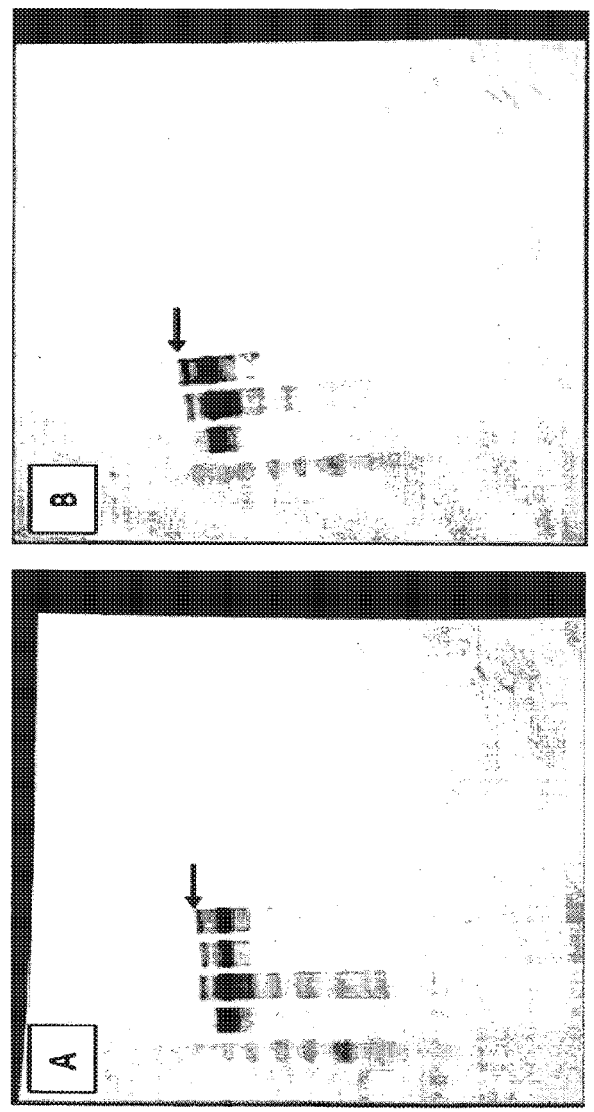
FIG. 6. Western-Blot analysis of additional Alphabody library phages. Phages were run on an 12% SDS-PAGE gel and transferred on a PVDF membrane for Western blot analysis. The pIII protein was visualized with an anti-pIII antibody. Panel A: The first two lanes are respectively, a size ladder (Color Plus Pre-stained protein Ladder broad range 10-230 kDa, NEB) and empty phages. The empty phages displayed only wild type pIII protein. The next three lanes are a reference Alphabody library, the scLib_AC12 and the scLib_AC11b library, respectively. Panel B: The first two lanes are respectively, a size ladder (Color Plus Pre-stained protein Ladder broad range 10-230 kDA, NEB) and phages. The next two lanes are a reference Alphabody library and the scLib_B10 library, respectively. The arrow indicates the Alphabody fusion pIII protein displaying a higher molecular weight than the wild type pIII protein.

The titers of the rescued libraries of this particular example are shown in Table 1. For the libraries scLib013APL8_AC12, scLib013APL16_B10 titers of 14 and 8 times the size of the library, respectively were obtained. Western blot analysis showed that for all libraries Alphabody-fusion pIII protein was present (FIG. 6). Two bands were visualized. The lower band corresponded to wild type pIII and the upper band with higher molecular weight to fusion pIII protein (FIG. 6). In conclusion, the rescue of the libraries was successful. Titers of a factor 10 above the initial library size were obtained and according the Western Blot, all libraries displayed fusion pIII proteins.

TABLE 1

| Library | Size of the library | Stock | Titer after rescue |
|---|---|---|---|
| scLib013APL8_AC12 | $1.4 \times 10^9$ | $2.3 \times 10^{10}$/ml | $2 \times 10^{10}$, 14 times library size |
| scLib013APL16_B10 | $2.2 \times 10^9$ | $1.9 \times 10^{10}$/ml | $1.9 \times 10^{10}$, 8 times library size |

Biopanning Protocol

A soluble biopanning protocol was used. The capturing of the target IL-23 after interaction with the phage library was performed using a biotinylated anti-p40 IL-23 antibody (Biolegend, 508802, clone C8.6) recognizing the subunit p40 of the cytokine IL-23. Prior to incubation with the library, the cytokine IL-23 (eBioscience, 34-8239-85, lot E034049) was incubated with the anti-p40 antibody. This strategy was developed to drive the selections towards binders of the p19 subunit of IL-23 by blocking the p40 unit with an antibody. This particular antibody was then also used to immobilize IL-23 on solid support for washing purposes.

Concretely, variable concentrations of IL-23 were incubated at twice the concentration of biotinylated anti-p40 IL-23 antibody in 0.1% BSA in PBS (phosphate buffered saline, pH 7.2) buffer for 1 hrs. The concentrations of IL-23 varied in function of the selection round as a part of the stringency protocol to obtain target-specific phage. Five rounds were performed using 200, 100, 50, 25, 12.5 nM of IL-23. In contrast, the concentration of input phage, i.e. phage added to the target in each selection round remained constant.

To avoid the selection of IgG-Fc binders since an anti-p40 antibody was used to bind IL-23, from the second round on, 20 micromolar of whole IgG (Sanguin, The Netherlands) was added to the IL-23_anti-p40 antibody_phage mixture. The phage were incubated with the target (anti-p40+IL-23) for 1 hr at room temperature followed by capturing on 0.1 ml streptavidin coated magnetic Dynabeads (Dynabeads M280 Streptavidin, Invitrogen) for 30 min. Prior use, the magnetic beads were washed as recommended by the manufacturer and blocked with 0.1% BSA in PBS for 1 hr at room temperature on a rotating wheel.

After capturing, the magnetic beads were then washed 10 times with 1 ml of PBS containing 0.1% of Tween 20 to eliminate non-specific phage. Magnetic beads can be easily washed by using a magnet as known to anyone skilled in the art of biopanning.

Target-specific phage were eluted from the beads using 0.2 ml glycine-HCl buffer pH 2 for 5 min. followed by neutralization with 0.05 ml of Tris buffer pH8. A supplementary fraction was recovered by adding directly mid-log bacteria to the magnetic bead.

A sample of the eluted phage was used to prepare ten-fold dilutions (1E-1 to 1 E-4) of the eluted phage in 2×TY for titration by infection of *E. coli* TG1 bacteria grown to mid-log phase (OD600 nm=0.5). The same dilutions (1E-7 to 1E-9) were also prepared from a small sample of the phage used as INPUT in the selection round. These titration results will allow the calculation of the yield of the selection round using the formula described earlier.

In this example, 0.9 ml bacteria were added to the 0.1 ml phage dilutions and incubated for 30 min at 37° C. 0.1 ml of the infection culture is plated on 2×TY-AG agar plates for colony counting and titer determination.

The eluted phage were used to infect 20 ml of mid-log phage *E. coli* TG1 bacteria during 30 min at 37° C. After incubation a bacterial pellet was obtained by centrifugation at 4000 rpm for 10 min. The pellet was resuspended in 2 ml of 2×TY and plated out on 2 big 2×TY-AG agar plates (25×25 cm).

A volume of 0.25 ml of mid-log phase bacteria were added directly on the magnetic beads and incubated for 30 min at 37° C. A sample was taken for titration as previously described. The infection culture was plated out on a big 2×TY-AG agar plate.

The next day colonies on each plate were counted and the titer of the INPUT and OUTPUT phage was determined for yield calculations. Bacteria on the big agar plates corresponding to the large infection culture were scraped from the plate using LB, the number of bacteria was determined by measuring at OD600 nm and 15% glycerol was added to store at −80° C. Phage were rescued from these glycerolstocks as previously described to obtain purified phage for the consecutive selections rounds. 1E12 phage were taken for the next selection round.

The titers obtained for the 5 selection rounds with the individual and pooled libraries on IL-23 are shown in Table 2. For biopanning with AC12 library the highest yield was obtained after four selection rounds (Table 2). Biopanning with the library B10 resulted in the highest yield after 5 rounds (Table 2). For the biopanning campaigns, enrichments were observed since the output titer increased between 48 and 100 times.

TABLE 2

| Round | IL-23 (nM) | concentration | INPUT titer | OUTPUT titer |
|---|---|---|---|---|
| | | Library AC12 | | |
| 1 | 200 | | $10 \times 10^{12}$ | $9 \times 10^5$ |
| 2 | 100 | | $10 \times 10^{12}$ | $3 \times 10^6$ |
| 3 | 50 | | $10 \times 10^{12}$ | $24 \times 10^6$ |
| 4 | 25 | | $10 \times 10^{12}$ | $43 \times 10^6$ |
| 5 | 12.5 | | $10 \times 10^{12}$ | $17 \times 10^6$ |
| | | Library B10 | | |
| 1 | 200 | | $10 \times 10^{12}$ | $3 \times 10^5$ |
| 2 | 100 | | $10 \times 10^{12}$ | $6 \times 10^5$ |
| 3 | 50 | | $10 \times 10^{12}$ | $9 \times 10^6$ |
| 4 | 25 | | $10 \times 10^{12}$ | $28 \times 10^6$ |
| 5 | 12.5 | | $10 \times 10^{12}$ | $2 \times 10^7$ |

To isolate target positive clones from the different selection rounds and to further determine the efficacy of the biopanning, screening by ELISA assays was performed. In this assay, supernatant from small volume bacterial cultures was tested. These bacterial cultures corresponded to individual clones (=individual phage) randomly picked from the titration plates from the different selection rounds. These bacterial clones were grown in 96 deep-well plates in 0.12 ml 2×TY-AG at 30° C. overnight while shaking (180 rpm) (MASTERPLATE). The next day, 0.002 ml of this plate was used to inoculate 0.1 ml/well of 2×TY-A without glucose and M13K07 helper phage were added (2×10⁹ plaque forming units/0.02 microl/well) immediately. After 2.5 hours of incubation at 37° C. while shaking (180 rpm), 0.030 ml 2×TY-AK (Amp: 0.1 mg/ml and Kan: 0.05 mg/ml) was added to the cultures and further incubated overnight for phage propagation at 30° c. while shaking (180 rpm).

For the masterplate, 0.020 ml of 80% glycerol was added for storage at −80° C. The masterplate serves to grow individual positive clones and subsequent phage purification for further characterization of their target interaction.

In this example, 44 clones per selection round from the 4 biopanning campaigns were screened. No clones were screened from the first selection round since the expectations to isolate target-specific clones from this round are low.

The set-up of the ELISA was as followed. Neutravidin was immobilized on the plate at a concentration of 0.010 mg/ml in PBS (0.100 ml) for 1 hour at room temperature (RT). Plates were washed 5 times with PBS containing 0.05% Tween 20 (PBST) for 5 min. Subsequently, 0.1 ml Biotinylated anti-p40 antibody (100 nM) was added to the plates in PBS containing 0.1% BSA and incubated overnight at 4° C. or at RT for 1 hour. After incubation, plates were washed 5 times with PBST and blocked with PBS containing 0.1% BSA and 0.5% gelatin (0.120 ml/well) for at least 1 hour at room temperature or overnight at 4° C. After washing 5 times with PBST, 100 nM IL-23 was added in 0.1 ml PBS, 0.1% BSA (=target). For individual negative controls no IL-23 was added (=background).

In the meanwhile, the bacteria plates were centrifuged at 1700 rpm for 10 min to pellet the bacteria. Plates with the immobilized IL-23 were washed 5 times with PBST and 0.050 ml of PBS with 0.2% BSA were added to the plate together with 0.050 ml of the bacterial culture supernatant containing phage. Plates were incubated for 1 to 1.5 hours at room temperature with shaking. Shaking of the plates enhanced the ELISA signals.

After the incubation the plates were washed 5 times with PBST and incubated with an anti-M13 antibody conjugated to HRP diluted 1:5000 in 2% PBS containing 0.1% BSA (0.1 ml/well) for 40 min at room temperature while rocking. Plates were washed 5 times and TMB (substrate of HRP) solution (0.1 ml/well) was added and plates were incubated in the dark between 5 to 30 min. The reaction was stopped by adding 0.05 ml 2N H2SO4 to each well and the plates were read at 450 nm.

Identification of Positive Clones

Clones were considered positive when the signal on the target was at least 3 times above background.

The biopanning campaign for AC12 resulted in a positive correlation between the percentage of positive clones determined by ELISA and the increasing selection rounds.

The library B10 performed less well and only a weak number of positive clones was retrieved from this library. For the AC12 library, more than 90% of positive clones were obtained after 4 selection rounds This ELISA can also be performed using soluble Alphabodies instead of Alphabodies displayed on phage. The production of soluble Alphabodies is based on the catabolic repression of the lacZ promoter by using glucose free conditions and the isopropylthio-beta-galactosidase (IPTG) induction of transcription by inactivating the lacIq repressor on the bacterial genome. The gene coding for Alphabody is transcribed and soluble Alphabody is produced.

Bacterial colonies are randomly picked from the titration plates of the selection rounds and grown in 96-well plates in 0.12 ml 2×TY-AG at 30° C., overnight while shaking (180 rpm). The next day, 0.002 ml of this plate is used to inoculate 0.1 ml/well of 2×TY-A with 0.1% glucose and further grown at 37° C. to reach an OD600 nm of 0.9 (approximately 2 to 3 hours). Then, 0.03 ml 2×TY-A with 3.3 mM IPTG is added to the cultures and further incubated at 30° c. while shaking (180 rpm) for 16 to 18 hours. After the induction of the expression with IPTG, 0.014 ml of freshly prepared B-per (Pierce) is added per well and incubated for 15 min at room temperature while mixing. The supernatant is then used in ELISA assays.

Sequencing

The Alphabody sequences were determined for all positive clones binding to IL-23 from the AC12 biopanning (picked from the different biopanningrounds). These sequences were determined by the standard DNA sequencing service of the VIB Genetic Service Facility, University of Antwerp (Belgium) using Sanger sequencing and M13RS sequencing primer. Table 3 (FIG. 8) shows a multiple alignment of 77 Alphabody sequences resulting from the AC12 library against IL-23. These Alphabodies can also be readily made in soluble Alphabodies (i.e. outside the phage format) as described above and subsequently purified by standard Ni-NTA/SEC procedure as known to anyone skilled in the art of protein purification. The Ni-NTA purification is a straightforward first purification step as usually the soluble Alphabody contains a His-tag either at the C-terminal end of the Alphabody (as is the case in the Alphabody library format AC12, B10) or at the N-terminus as the result of a recloning step wherein a given Alphabody gene is excised from its phage context (by standard molecular biology techniques) and inserted in a suitable expression vector such as e.g. pET16 wherein a hisTag and protease cleavage site precedes the Alphabody gene. To determine the Kd (dissociation constant) for binding to IL-23, the soluble Alphabodies are subjected to a (kinetic) Biacore analysis or to Friguet (indirect ELISA) analysis (Friguet et al., 1985) or to another appropriate method as known to anyone skilled in the art of measuring binding strengths.

Cross-Reactivity with Mouse IL-23

The cross-reactivity with mouse IL-23 was studied using ELISA assays in which mouse IL-23 was captured by an mouse anti-p40 antibody in analogy with the human IL-23 strategy. The ELISA assays were performed as previously described and clones were considered positive when their signal on target was at least 2.5 times above the signal on background. It was observed that for the IL-23 positive clones resulting from the AC12 library, 26% of the analyzed clones were cross-reactive with mouse IL-23 (T/B>2.5).

Cross-Reactivity with IL-12

The domain specificity of the 127 different clones was also tested on human IL-12. The ELISA was performed as described for IL-23. Human IL-12 was captured on the plate via an anti-human p40 antibody and the ELISA was performed as previously described. The ELISA results showed that 5/76 and 0 clones from respectively the AC12 and B10 libraries were cross-reactive with human IL-12. For the AC12 library 4 on the 5 human IL-12 positive clones also cross-reacted with mouse IL-23.

The invention claimed is:

1. A method for the production of one or more single-chain Alphabody polypeptides,
wherein said method at least comprises the steps of:
a) producing a single-chain Alphabody library comprising at least 100 different single-chain Alphabody polypeptides,
each of said single-chain Alphabody polypeptides having the general formula HRS1-L1-HRS2-L2-HRS3, wherein
each of HRS 1, HRS2 and HRS3 is independently a heptad repeat sequence (HRS) consisting of 2 to 7 consecutive heptad repeat units, at least 50% of all heptad a- and d-positions are occupied by isoleucine residues, each HRS starts and ends with an aliphatic or aromatic amino acid residue located at either a heptad a- or d-position, and HRS1, HRS2and HRS3 together form a triple-stranded, alpha-helical, coiled coil structure; and
each of L1 and L2 is independently a linker fragment, which covalently connects HRS1 to HRS2 and HRS2 to HRS3, respectively, and consisting of at least 4 amino acid residues, preferably at least 50% of which are selected from the group proline, glycine, serine;
wherein said Alphabody polypeptides differ from each other in at least one of a defined set of 5 to 20 variegated amino acid residue positions, and wherein at least 70% but not all of said variegated amino acid residue positions are located either:
(i) at heptad e-positions in a first alpha-helix of the Alphabody polypeptides and at heptad g-positions in a second alpha-helix, and optionally at heptad b-positions in said first alpha-helix of the Alphabody polypeptides and/or at heptad c-positions in said second alpha-helix of the Alphabody polypeptides, or
(ii) at heptad b-, c- and f-positions in one alpha-helix of the Alphabody polypeptides, or
(iii) at positions in a linker fragment connecting two consecutive alpha-helices of the Alphabody polypeptides
or a mixture of between two and six of said single-chain Alphabody libraries,
b) selecting one or more single-chain Alphabody polypeptides having detectable binding affinity for a target molecule of interest, or detectable in vitro activity on a target molecule or cell of interest, and
c) isolating said one or more single-chain Alphabody polypeptides.

2. The method according to claim 1, wherein said step of selecting one or more single-chain Alphabody polypeptides having detectable binding affinity for a target molecule of interest, comprises:
a) contacting said target molecule of interest with said single-chain Alphabody library or with a mixture of between two and six of said single-chain Alphabody libraries,
b) identifying from said single-chain Alphabody library or mixture of single-chain Alphabody libraries being contacted with said target molecule of interest, the one or more single-chain Alphabody polypeptides having detectable binding affinity for said target molecule of interest, and optionally
c) determining the amino acid or nucleotide sequence of said one or more single-chain Alphabody polypeptides having detectable binding affinity for said target molecule of interest.

3. The method according to claim 2, wherein said Alphabody library or mixture of Alphabody libraries is further enriched for single-chain Alphabody polypeptides having detectable binding affinity for said target molecule of interest by iterative execution of steps a) and b).

4. The method according to claim 1, wherein said step of selecting one or more single-chain Alphabody polypeptides having detectable in vitro activity on a target molecule or cell of interest, comprises:
- a1) expressing said single-chain Alphabody library or a mixture of between two and six of said single-chain Alphabody libraries in said target cells of interest, or
- a2) contacting said single-chain Alphabody library or mixture of between two and six of said single-chain Alphabody libraries with said target cells of interest,
- b) identifying from said expressed single-chain Alphabody library or mixture of single-chain Alphabody libraries, the one or more single-chain Alphabodies having detectable in vitro activity on said target molecule or cell of interest, and optionally
- c) determining the amino acid or nucleotide sequence of said one or more single-chain Alphabody polypeptides having detectable in vitro activity on said target molecule or cell of interest.

5. The method according to claim 1, which further comprises step d) of amplifying said one or more single-chain Alphabody polypeptides having detectable binding affinity for, or detectable in vitro activity on, a target protein or cell of interest.

* * * * *

SEQUENCE LISTING

```
<160> NUMBER OF SEQ ID NOS: 118

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(2)
<223> OTHER INFORMATION: N-terminal
<220> FEATURE:
<221> NAME/KEY: misc_feature
<222> LOCATION: (3)..(27)
<223> OTHER INFORMATION: HRS1
<220> FEATURE:
<221> NAME/KEY: misc_feature
<222> LOCATION: (28)..(46)
<223> OTHER INFORMATION: L1
<220> FEATURE:
<221> NAME/KEY: misc_feature
<222> LOCATION: (47)..(71)
<223> OTHER INFORMATION: HRS2
<220> FEATURE:
<221> NAME/KEY: misc_feature
<222> LOCATION: (72)..(90)
<223> OTHER INFORMATION: L2
<220> FEATURE:
<221> NAME/KEY: misc_feature
<222> LOCATION: (91)..(115)
<223> OTHER INFORMATION: HRS3
<220> FEATURE:
<221> NAME/KEY: misc_feature
<222> LOCATION: (116)..(117)
<223> OTHER INFORMATION: C-terminal

<400> SEQUENCE: 1

Met Ser Ile Glu Glu Ile Gln Lys Gln Ile Ala Ala Ile Gln Lys Gln
1               5                   10                  15

Ile Ala Ala Ile Gln Lys Gln Ile Tyr Arg Met Thr Gly Gly Ser Gly
            20                  25                  30

Gly Gly Ser Gly Gly Gly Ser Gly Gly Gly Ser Gly Met Ser Ile Glu
        35                  40                  45

Glu Ile Gln Lys Gln Ile Ala Ala Ile Gln Lys Gln Ile Ala Ala Ile
    50                  55                  60

Gln Lys Gln Ile Tyr Arg Met Thr Gly Gly Ser Gly Gly Gly Ser Gly
65                  70                  75                  80

Gly Gly Ser Gly Gly Gly Ser Gly Met Ser Ile Glu Glu Ile Gln Lys
                85                  90                  95

Gln Ile Ala Ala Ile Gln Lys Gln Ile Ala Ala Ile Gln Lys Gln Ile
            100                 105                 110

Tyr Arg Met Thr Pro
        115

<210> SEQ ID NO 2
<211> LENGTH: 155
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(22)
<223> OTHER INFORMATION: N-terminal
<220> FEATURE:
<221> NAME/KEY: misc_feature
<222> LOCATION: (23)..(47)
<223> OTHER INFORMATION: HRS1
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: misc_feature
<222> LOCATION: (48)..(66)
<223> OTHER INFORMATION: L1
<220> FEATURE:
<221> NAME/KEY: misc_feature
<222> LOCATION: (67)..(91)
<223> OTHER INFORMATION: HRS2
<220> FEATURE:
<221> NAME/KEY: misc_feature
<222> LOCATION: (92)..(110)
<223> OTHER INFORMATION: L2
<220> FEATURE:
<221> NAME/KEY: misc_feature
<222> LOCATION: (111)..(135)
<223> OTHER INFORMATION: HRS3
<220> FEATURE:
<221> NAME/KEY: MOD_RES
<222> LOCATION: (119)..(119)
<223> OTHER INFORMATION: Any amino acid
<220> FEATURE:
<221> NAME/KEY: MOD_RES
<222> LOCATION: (122)..(122)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (129)..(129)
<223> OTHER INFORMATION: Any amino acid
<220> FEATURE:
<221> NAME/KEY: MOD_RES
<222> LOCATION: (133)..(133)
<223> OTHER INFORMATION: Any amino acid
<220> FEATURE:
<221> NAME/KEY: misc_feature
<222> LOCATION: (136)..(155)
<223> OTHER INFORMATION: C-terminal
```

<400> SEQUENCE: 2

Met Lys Tyr Leu Leu Pro Thr Ala Ala Ala Gly Leu Leu Leu Ala
1               5                   10                  15

Ala Gln Pro Ala Met Ser Ile Glu Glu Ile Gln Lys Xaa Ile Ala Xaa
            20                  25                  30

Ile Gln Glu Xaa Ile Ala Xaa Ile Gln Lys Xaa Ile Tyr Xaa Met Thr
        35                  40                  45

Gly Gly Ser Gly Gly Gly Ser Gly Gly Gly Ser Gly Gly Gly Ser Gly
    50                  55                  60

Met Ser Ile Glu Glu Ile Gln Lys Gln Ile Ala Ala Ile Gln Lys Gln
65                  70                  75                  80

Ile Ala Ala Ile Gln Lys Gln Ile Tyr Ala Met Thr Gly Gly Ser Gly
                85                  90                  95

Gly Gly Ser Gly Gly Gly Ser Gly Gly Gly Ser Gly Met Ser Ile Glu
            100                 105                 110

Glu Ile Gln Lys Gln Ile Xaa Ala Ile Xaa Glu Gln Ile Xaa Ala Ile
        115                 120                 125

Xaa Lys Gln Ile Xaa Ala Met Thr Pro Gly Gly Ser Gly Gly Ala Ala
    130                 135                 140

Ala His His His His His His Gly Arg Ala Glu
145                 150                 155

<210> SEQ ID NO 3
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(22)
<223> OTHER INFORMATION: N-terminal
<220> FEATURE:
<221> NAME/KEY: misc_feature
<222> LOCATION: (23)..(40)
<223> OTHER INFORMATION: HRS1
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (39)..(39)
<223> OTHER INFORMATION: Any amino acid
<220> FEATURE:
<221> NAME/KEY: misc_feature
<222> LOCATION: (41)..(59)
<223> OTHER INFORMATION: L1
<220> FEATURE:
<221> NAME/KEY: misc_feature
<222> LOCATION: (60)..(77)
<223> OTHER INFORMATION: HRS2
<220> FEATURE:
<221> NAME/KEY: misc_feature
<222> LOCATION: (78)..(96)
<223> OTHER INFORMATION: L2

```
<220> FEATURE:
<221> NAME/KEY: misc_feature
<222> LOCATION: (97)..(114)
<223> OTHER INFORMATION: HRS3
<220> FEATURE:
<221> NAME/KEY: MOD_RES
<222> LOCATION: (105)..(105)
<223> OTHER INFORMATION: Any amino acid
<220> FEATURE:
<221> NAME/KEY: MOD_RES
<222> LOCATION: (108)..(108)
<223> OTHER INFORMATION: Any amino acid
<220> FEATURE:
<221> NAME/KEY: MOD_RES
<222> LOCATION: (112)..(112)
<223> OTHER INFORMATION: Any amino acid
<220> FEATURE:
<221> NAME/KEY: misc_feature
<222> LOCATION: (115)..(134)
<223> OTHER INFORMATION: C-terminal

<400> SEQUENCE: 3

Met Lys Tyr Leu Leu Pro Thr Ala Ala Gly Leu Leu Leu Ala
  1               5                  10                  15

Ala Gln Pro Ala Met Asp Ile Gln Gln Ile Gln Lys Xaa Ile Ala Xaa
                 20                  25                  30

Ile Gln Glu Xaa Ile Tyr Xaa Met Thr Gly Ser Gly Gly Ser
             35                  40                  45

Gly Gly Gly Ser Gly Gly Gly Ser Gly Met Asp Ile Gln Gln Ile Gln
 50                  55                  60

Lys Gln Ile Ala Ala Ile Gln Lys Gln Ile Tyr Ala Met Thr Gly Gly
 65                  70                  75                  80

Ser Gly Gly Gly Ser Gly Gly Gly Ser Gly Gly Ser Gly Met Asp
             85                  90                  95

Ile Gln Gln Ile Gln Lys Gln Ile Xaa Ala Ile Xaa Glu Gln Ile Xaa
                100                 105                 110

Ala Met Thr Pro Gly Gly Ser Gly Gly Ala Ala His His His His
            115                 120                 125

His His Gly Arg Ala Glu
    130

<210> SEQ ID NO 4
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(23)
<223> OTHER INFORMATION: N-terminal
<220> FEATURE:
<221> NAME/KEY: misc_feature
<222> LOCATION: (24)..(48)
<223> OTHER INFORMATION: HRS1
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (37)..(37)
<223> OTHER INFORMATION: Any amino acid
```

```
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (44)..(44)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: misc_feature
<222> LOCATION: (49)..(67)
<223> OTHER INFORMATION: L1
<220> FEATURE:
<221> NAME/KEY: misc_feature
<222> LOCATION: (68)..(92)
<223> OTHER INFORMATION: HRS2
<220> FEATURE:
<221> NAME/KEY: misc_feature
<222> LOCATION: (93)..(111)
<223> OTHER INFORMATION: L2
<220> FEATURE:
<221> NAME/KEY: misc_feature
<222> LOCATION: (112)..(136)
<223> OTHER INFORMATION: HRS3
<220> FEATURE:
<221> NAME/KEY: MOD_RES
<222> LOCATION: (120)..(120)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<221> NAME/KEY: MOD_RES
<222> LOCATION: (127)..(127)
<223> OTHER INFORMATION: Any amino acid
<220> FEATURE:
<221> NAME/KEY: MOD_RES
<222> LOCATION: (130)..(130)
<223> OTHER INFORMATION: Any amino acid
<220> FEATURE:
<221> NAME/KEY: MOD_RES
<222> LOCATION: (134)..(134)
<223> OTHER INFORMATION: Any amino acid
<220> FEATURE:
<221> NAME/KEY: misc_feature
<222> LOCATION: (137)..(156)
<223> OTHER INFORMATION: C-terminal

<400> SEQUENCE: 4

Met Lys Tyr Leu Leu Pro Thr Ala Ala Ala Gly Leu Leu Leu Leu Ala
 1               5                  10                  15

Ala Gln Pro Ala Gly Gly Ser Ile Glu Gln Ile Gln Lys Xaa Ile Ala
            20                  25                  30

Xaa Ile Gln Glu Xaa Ile Ala Xaa Ile Gln Lys Xaa Ile Tyr Xaa Met
        35                  40                  45

Thr Gly Gly Ser Gly Gly Ser Gly Gly Gly Ser Gly Gly Ser Gly
    50                  55                  60

Gly Gly Ser Ile Glu Gln Ile Gln Lys Gln Ile Ala Ala Ile Gln Lys
65                  70                  75                  80

Gln Ile Ala Ala Ile Gln Lys Gln Ile Tyr Ala Met Thr Gly Ser Gly
                85                  90                  95

Gly Gly Ser Gly Gly Ser Gly Gly Gly Ser Gly Gly Ser Ile
            100                 105                 110

Glu Gln Ile Gln Lys Gln Ile Xaa Ala Ile Xaa Glu Gln Ile Xaa Ala
        115                 120                 125
```

```
Ile Xaa Lys Gln Ile Xaa Ala Met Thr Pro Gly Gly Ser Gly Gly Ala
        130                 135                 140

Ala Ala His His His His His His Gly Arg Ala Glu
145                 150                 155

<210> SEQ ID NO 5
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(22)
<223> OTHER INFORMATION: N-terminal
<220> FEATURE:
<221> NAME/KEY: misc_feature
<222> LOCATION: (23)..(47)
<223> OTHER INFORMATION: HRS1
<220> FEATURE:
<221> NAME/KEY: misc_feature
<222> LOCATION: (48)..(66)
<223> OTHER INFORMATION: L1
<220> FEATURE:
<221> NAME/KEY: misc_feature
<222> LOCATION: (67)..(91)
<223> OTHER INFORMATION: HRS2
<220> FEATURE:
<221> NAME/KEY: misc_feature
<222> LOCATION: (92)..(110)
<223> OTHER INFORMATION: L2
<220> FEATURE:
<221> NAME/KEY: misc_feature
<222> LOCATION: (111)..(135)
<223> OTHER INFORMATION: HRS3
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (119)..(120)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<221> NAME/KEY: MOD_RES
<222> LOCATION: (126)..(127)
<223> OTHER INFORMATION: Any amino acid
<220> FEATURE:
<221> NAME/KEY: MOD_RES
<222> LOCATION: (130)..(130)
<223> OTHER INFORMATION: Any amino acid
<220> FEATURE:
<221> NAME/KEY: MOD_RES
<222> LOCATION: (133)..(134)
<223> OTHER INFORMATION: Any amino acid
<220> FEATURE:
<221> NAME/KEY: misc_feature
<222> LOCATION: (136)..(155)
<223> OTHER INFORMATION: C-terminal

<400> SEQUENCE: 5

Met Lys Tyr Leu Leu Pro Thr Ala Ala Ala Gly Leu Leu Leu Leu Ala
1               5                   10                  15

Ala Gln Pro Ala Met Ser Ile Glu Glu Ile Gln Lys Gln Ile Ala Ala
                20                  25                  30

Ile Gln Lys Gln Ile Ala Ala Ile Gln Lys Gln Ile Tyr Ala Met Thr
        35                  40                  45
```

Gly Gly Ser Gly Gly Gly Ser Gly Gly Gly Ser Gly
50              55              60

Met Ser Ile Glu Glu Ile Gln Lys Gln Ile Ala Ala Ile Gln Lys Gln
65              70              75              80

Ile Ala Ala Ile Gln Lys Gln Ile Tyr Ala Met Thr Gly Gly Ser Gly
                85              90              95

Gly Gly Ser Gly Gly Gly Ser Gly Gly Gly Ser Gly Met Ser Ile Glu
                100             105             110

Glu Ile Gln Xaa Gln Ile Xaa Xaa Ile Gln Xaa Gln Ile Xaa Xaa Ile
            115             120             125

Gln Xaa Gln Ile Xaa Xaa Met Thr Pro Gly Gly Ser Gly Gly Ala Ala
130             135             140

Ala His His His His His His Gly Arg Ala Glu
145             150             155

<210> SEQ ID NO 6
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(23)
<223> OTHER INFORMATION: N-terminal
<220> FEATURE:
<221> NAME/KEY: misc_feature
<222> LOCATION: (24)..(48)
<223> OTHER INFORMATION: HRS1
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (44)..(44)
<223> OTHER INFORMATION: Any amino acid
<220> FEATURE:
<221> NAME/KEY: misc_feature
<222> LOCATION: (49)..(59)
<223> OTHER INFORMATION: L1
<220> FEATURE:
<221> NAME/KEY: misc_feature
<222> LOCATION: (60)..(84)
<223> OTHER INFORMATION: HRS2
<220> FEATURE:
<221> NAME/KEY: misc_feature
<222> LOCATION: (85)..(95)
<223> OTHER INFORMATION: L2
<220> FEATURE:
<221> NAME/KEY: misc_feature
<222> LOCATION: (96)..(120)
<223> OTHER INFORMATION: HRS3
<220> FEATURE:
<221> NAME/KEY: MOD_RES
<222> LOCATION: (104)..(104)
<223> OTHER INFORMATION: Any amino acid -continued

```
<220> FEATURE:
<221> NAME/KEY: MOD_RES
<222> LOCATION: (107)..(108)
<223> OTHER INFORMATION: Any amino acid
<220> FEATURE:
<221> NAME/KEY: MOD_RES
<222> LOCATION: (111)..(111)
<223> OTHER INFORMATION: Any amino acid
<220> FEATURE:
<221> NAME/KEY: MOD_RES
<222> LOCATION: (114)..(115)
<223> OTHER INFORMATION: Any amino acid
<220> FEATURE:
<221> NAME/KEY: MOD_RES
<222> LOCATION: (118)..(118)
<223> OTHER INFORMATION: Any amino acid
<220> FEATURE:
<221> NAME/KEY: misc_feature
<222> LOCATION: (121)..(140)
<223> OTHER INFORMATION: C-terminal

<400> SEQUENCE: 6

Met Lys Tyr Leu Leu Pro Thr Ala Ala Gly Leu Leu Leu Leu Ala
 1               5                  10                  15

Ala Gln Pro Ala Gly Gly Ser Ile Glu Gln Ile Gln Lys Xaa Ile Ala
             20                  25                  30

Xaa Ile Gln Glu Xaa Ile Ala Xaa Ile Gln Lys Xaa Ile Tyr Ala Met
         35                  40                  45

Thr Gly Ser Gly Gly Ser Gly Gly Ser Ile Glu Gln Ile Gln
 50                  55                  60

Lys Gln Ile Ala Ala Ile Gln Lys Gln Ile Ala Ala Ile Gln Lys Gln
 65                  70                  75                  80

Ile Tyr Ala Met Thr Gly Ser Gly Gly Ser Gly Gly Ser Ile
             85                  90                  95

Glu Gln Ile Gln Lys Gln Ile Xaa Ala Ile Xaa Xaa Gln Ile Xaa Ala
            100                 105                 110

Ile Xaa Xaa Gln Ile Xaa Ala Met Thr Pro Gly Gly Ser Gly Gly Ala
        115                 120                 125

Ala Ala His His His His His His Gly Arg Ala Glu
        130                 135                 140

<210> SEQ ID NO 7
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(22)
<223> OTHER INFORMATION: N-terminal
<220> FEATURE:
<221> NAME/KEY: misc_feature
<222> LOCATION: (23)..(47)
<223> OTHER INFORMATION: HRS1
<220> FEATURE:
<221> NAME/KEY: misc_feature
<222> LOCATION: (48)..(66)
<223> OTHER INFORMATION: L1
<220> FEATURE:
<221> NAME/KEY: misc_feature
<222> LOCATION: (67)..(91)
<223> OTHER INFORMATION: HRS2
<220> FEATURE:
<221> NAME/KEY: MOD_RES
<222> LOCATION: (76)..(76)
<223> OTHER INFORMATION: Any amino acid
```

```
<220> FEATURE:
<221> NAME/KEY: MOD_RES
<222> LOCATION: (79)..(80)
<223> OTHER INFORMATION: Any amino acid
<220> FEATURE:
<221> NAME/KEY: MOD_RES
<222> LOCATION: (82)..(83)
<223> OTHER INFORMATION: Any amino acid
<220> FEATURE:
<221> NAME/KEY: MOD_RES
<222> LOCATION: (86)..(87)
<223> OTHER INFORMATION: Any amino acid
<220> FEATURE:
<221> NAME/KEY: MOD_RES
<222> LOCATION: (89)..(90)
<223> OTHER INFORMATION: Any amino acid
<220> FEATURE:
<221> NAME/KEY: misc_feature
<222> LOCATION: (92)..(110)
<223> OTHER INFORMATION: L2
<220> FEATURE:
<221> NAME/KEY: misc_feature
<222> LOCATION: (111)..(135)
<223> OTHER INFORMATION: HRS3
<220> FEATURE:
<221> NAME/KEY: MOD_RES
<222> LOCATION: (117)..(117)
<223> OTHER INFORMATION: Any amino acid
<220> FEATURE:
<221> NAME/KEY: misc_feature
<222> LOCATION: (136)..(155)
<223> OTHER INFORMATION: C-terminal

<400> SEQUENCE: 7

Met Lys Tyr Leu Leu Pro Thr Ala Ala Ala Gly Leu Leu Leu Leu Ala
1               5                   10                  15

Ala Gln Pro Ala Met Ser Ile Glu Glu Ile Gln Lys Gln Ile Ala Ala
            20                  25                  30

Ile Gln Glu Gln Ile Ala Ala Ile Gln Lys Gln Ile Tyr Ala Met Thr
        35                  40                  45

Gly Gly Ser Gly Gly Ser Gly Gly Gly Ser Gly Ser Gly Gly
    50                  55                  60

Met Ser Ile Glu Glu Ile Gln Lys Gln Ile Ala Xaa Ile Gln Xaa Xaa
65                  70                  75                  80

Ile Xaa Xaa Ile Gln Xaa Xaa Ile Xaa Xaa Met Thr Gly Ser Gly Gly
            85                  90                  95

Gly Gly Ser Gly Gly Ser Gly Gly Gly Ser Gly Met Ser Ile Glu
                100                 105                 110

Glu Ile Gln Lys Xaa Ile Ala Ala Ile Gln Glu Gln Ile Ala Ala Ile
        115                 120                 125

Gln Lys Gln Ile Tyr Ala Met Thr Pro Gly Gly Ser Gly Gly Ala Ala
    130                 135                 140

Ala His His His His His His Gly Arg Ala Glu
145                 150                 155

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
```

<400> SEQUENCE: 8

Gly Ser Ile Glu Gln Ile Gln Lys Trp Xaa Ala
1               5                   10

<210> SEQ ID NO 9
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Ser Ile Glu Gln Ile Gln Lys Gly Ile Ala Arg Ile Gln Glu Val
1               5                   10                  15

Ile Ala Lys Ile Gln Lys Gly Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Val Ala Ile Thr His Gln Ile Thr Ala Ile Ile Trp Gln Ile
                85                  90                  95

Trp Ala Met Thr Pro
            100

<210> SEQ ID NO 10
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Ser Ile Glu Gln Ile Gln Lys Arg Ile Ala Phe Ile Gln Glu Thr
1               5                   10                  15

Ile Ala Trp Ile Gln Lys Asn Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Ser Ala Ile Ala Arg Gln Ile Arg Ala Ile Leu Gly Gln Ile
                85                  90                  95

Phe Ala Met Thr Pro
            100

<210> SEQ ID NO 11
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Ser Ile Glu Gln Ile Gln Lys Thr Ile Ala Met Ile Gln Glu Tyr
1               5                   10                  15

Ile Ala Trp Ile Gln Lys Lys Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Arg Ala Ile Val Gly Gln Ile Met Ala Ile Leu Arg Gln Ile
                85                  90                  95

Thr Ala Met Thr Pro
            100

<210> SEQ ID NO 12
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Ser Ile Glu Gln Ile Gln Lys Phe Ile Ala Asn Ile Gln Glu Leu
1               5                   10                  15

Ile Ala Cys Ile Gln Lys Asn Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Thr Ala Ile Ala Ser Gln Ile Tyr Ala Ile Val Ala Gln Ile
                85                  90                  95

Thr Ala Met Thr Pro
            100

<210> SEQ ID NO 13
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ser Ile Glu Gln Ile Gln Lys Gly Ile Ala Leu Ile Gln Glu Trp
1               5                   10                  15

Ile Ala Trp Ile Gln Lys Ser Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Ser Gly Gly Ser Ile Glu Gln Ile Gln Lys
65                  70                  75                  80

Gln Ile Leu Ala Ile Ser Leu Gln Ile Met Ala Ile Leu Glu Gln Ile
            85                  90                  95

Met Ala Met Thr Pro
            100

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Ile Glu Gln Ile Gln Lys Ile Ile Ala Gly Ile Gln Glu Gly
1               5                   10                  15

Ile Ala Ser Ile Gln Lys
            20

<210> SEQ ID NO 15
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ser Ile Glu Gln Ile Gln Lys Tyr Ile Ala Pro Ile Gln Glu Ile
1               5                   10                  15

Ile Ala Lys Ile Gln Lys Leu Ile Tyr Ala Met Thr Gly Gly Ser Gly
            20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Gly Ser Gly Gly Ser Ile Glu Gln Ile Gln Lys
65                  70                  75                  80

Gln Ile Gly Ala Ile Ile Ser Gln Ile Gly Ala Ile Leu Gly Gln Ile
            85                  90                  95

Tyr Ala Met Thr Pro
            100

<210> SEQ ID NO 16
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Ser Ile Glu Gln Ile Gln Lys Lys Ile Ala Thr Ile Gln Glu Tyr
1               5                   10                  15

Ile Ala Tyr Ile Gln Lys Phe Ile Tyr Ala Met Thr Gly Gly Ser Gly
            20                  25                  30

Gly Ser Gly Gly Gly Ser Ile Glu Gln Ile Gln Lys Gln Ile Ala Ala
            35                  40                  45

```
Ile Gln Lys Gln Ile Ala Ala Ile Gln Lys Gln Ile Tyr Ala Met Thr
        50                  55                  60

Gly Ser Gly Gly Gly Ser Gly Gly Ser Ile Glu Gln Ile Gln Lys
65                  70                  75                  80

Gln Ile Lys Ala Ile Leu Gly Gln Ile Gly Ala Ile Ile Gly Gln Ile
                85                  90                  95

Trp Ala Met Thr Pro
            100

<210> SEQ ID NO 17
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Ser Ile Glu Gln Ile Gln Lys Lys Ile Ala Val Ile Gln Glu Val
1               5                   10                  15

Ile Ala Gly Ile Gln Lys Gly Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Ser Gly Gly Ser Ile Glu Gln Ile Gln Lys
65                  70                  75                  80

Gln Ile Ser Ala Ile Ile Ile Gln Ile Thr Ala Ile Val Lys Gln Ile
                85                  90                  95

Met Ala Met Thr Pro
            100

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Ile Glu Gln Ile Gln Lys Tyr Ile Ala Met Ile Gln Glu
1               5                   10                  15

<210> SEQ ID NO 19
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (16)..(16)
<223> OTHER INFORMATION: Any amino acid
```

```
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (94)..(94)
<223> OTHER INFORMATION: Any amino acid

<400> SEQUENCE: 19

Gly Ser Ile Glu Gln Ile Gln Lys Xaa Ile Ala Xaa Ile Gln Glu Xaa
1               5                   10                  15

Ile Ala Asn Ile Gln Lys Arg Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Ser Gly Gly Ser Ile Glu Gln Ile Gln Lys
65                  70                  75                  80

Gln Ile Arg Ala Ile Xaa Glu Gln Ile Ala Ala Ile Phe Xaa Gln Ile
                85                  90                  95

Phe Ala Met Thr Pro
            100

<210> SEQ ID NO 20
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Ser Ile Glu Gln Ile Gln Lys Arg Ile Ala Pro Ile Gln Glu Cys
1               5                   10                  15

Ile Ala Phe Ile Gln Lys Leu Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Ser Gly Gly Ser Ile Glu Gln Ile Gln Lys
65                  70                  75                  80

Gln Ile Thr Ala Ile Gly Arg Gln Ile Met Ala Ile Phe Ile Gln Ile
                85                  90                  95

Trp Ala Met Thr Pro
            100

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ser Ile Glu Gln Ile Gln Lys Arg Ile Ala Arg Ile Gln Glu Pro
1               5                   10                  15

Ile Ala
```

```
<210> SEQ ID NO 22
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (97)..(97)
<223> OTHER INFORMATION: Any amino acid

<400> SEQUENCE: 22

Gly Ser Ile Glu Gln Ile Gln Lys Xaa Ile Ala Xaa Ile Gln Glu Trp
1               5                   10                  15

Ile Ala Gln Ile Gln Lys Xaa Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Trp Ala Ile Val Ser Gln Ile Xaa Ala Ile Leu Val Gln Ile
                85                  90                  95

Xaa Ala Met Thr Pro
            100

<210> SEQ ID NO 23
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Ser Ile Glu Gln Ile Gln Lys Val Ile Ala Tyr Ile Gln Glu Lys
1               5                   10                  15

Ile Ala Val Ile Gln Lys Ser Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile
```

-continued

<210> SEQ ID NO 24
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (87)..(87)
<223> OTHER INFORMATION: Any amino acid

<400> SEQUENCE: 24

Gly Ser Ile Glu Gln Ile Gln Lys Arg Ile Ala Gly Ile Gln Glu Arg
1               5                   10                  15

Ile Ala Xaa Ile Gln Lys Xaa Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
50                  55                  60

Gly Ser Gly Gly Gly Gly Ser Gly Gly Ser Ile Glu Gln Ile Gln Lys
65                  70                  75                  80

Gln Ile Glu Ala Ile Ser Xaa Gln Ile Val Ala Ile Gly Gln Ile
                85                  90                  95

Leu Ala Met Thr Pro
            100

<210> SEQ ID NO 25
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Ser Ile Glu Gln Ile Gln Lys Thr Ile Ala Ser Ile Gln Glu Val
1               5                   10                  15

Ile Ala Ala Ile Gln Lys Tyr Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
50                  55                  60

Gly Ser Gly Gly Gly Gly Ser Gly Gly Ser Ile Glu Gln Ile Gln Lys
65                  70                  75                  80

Gln Ile Ala Ala Ile Gly Ser Gln Ile Ile Ala Ile Val Arg Gln Ile
                85                  90                  95

Arg Ala Met Thr Pro
            100

<210> SEQ ID NO 26
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Ser Ile Glu Gln Ile Gln Lys Thr Ile Ala Ala Ile Gln Glu Cys
1               5                   10                  15

Ile Ala Arg Ile Gln Lys Ala Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
50                  55                  60

Gly Ser Gly Gly Gly Gly Ser Gly Gly Ser Ile Glu Gln Ile Gln Lys
65                  70                  75                  80

Gln Ile Arg Ala Ile Val Ser Gln Ile Ser Ala Ile Leu Ile Gln Ile
                85                  90                  95

Gly Ala Met Thr Pro
            100

<210> SEQ ID NO 27
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Ser Ile Glu Gln Ile Gln Lys Val Ile Ala Arg Ile Gln Glu Val
1               5                   10                  15

Ile Ala Ser Ile Gln Lys Tyr Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
50                  55                  60

Gly Ser Gly Gly Gly Gly Ser Gly Gly Ser Ile Glu Gln Ile Gln Lys
65                  70                  75                  80

Gln Ile Gly Ala Ile Val Thr Gln Ile Leu Ala Ile Ile Ser Gln Ile
                85                  90                  95

Thr Ala Met Thr Pro
            100

<210> SEQ ID NO 28
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Ser Ile Glu Gln Ile Gln Lys Ser Ile Ala Arg Ile Gln Glu Gly
1               5                   10                  15

Ile Ala Pro Ile Gln Lys Met Ile Tyr Ala Met Thr Gly Gly Ser Gly
                20                  25                  30

```
Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
         50                  55                  60

Gly Ser Gly Gly Gly Ser Gly Gly Ser Ile Glu Gln Ile Gln Lys
 65                  70                  75                  80

Gln Ile Met Ala Ile Ala Gly Gln Ile Gly Ala Ile Leu
             85                  90
```

<210> SEQ ID NO 29
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Gly Ser Ile Glu Gln Ile Gln Lys Met Ile Ala Pro Ile Gln Glu Leu
 1               5                  10                  15

Ile Ala Arg Ile Gln Lys Asp Ile Tyr Ala Met Thr Gly Gly Ser Gly
             20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
         50                  55                  60

Gly Ser Gly Gly Gly Gly Ser Gly Gly Ser Ile Glu Gln Ile Gln Lys
 65                  70                  75                  80

Gln Ile Gly Ala Ile Thr Arg Gln Ile Leu Ala Ile Leu Val Gln Ile
             85                  90                  95

Gly Ala Met Thr Pro
            100
```

<210> SEQ ID NO 30
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Gly Ser Ile Glu Gln Ile Gln Lys Phe Ile Ala Ser Ile Gln Glu Cys
 1               5                  10                  15

Ile Ala Arg Ile Gln Lys Thr Ile Tyr Ala Met Thr Gly Gly Ser Gly
             20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
         50                  55                  60

Gly Ser Gly Gly Gly Gly Ser Gly Gly Ser Ile Glu Gln Ile Gln Lys
 65                  70                  75                  80

Gln Ile Lys Ala Ile Arg Thr Gln Ile Phe Ala Ile Phe Arg Gln Ile
             85                  90                  95

Tyr Ala Met Thr Pro
            100
```

```
<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Ile Glu Gln Ile Gln Lys Pro Ile Ala Leu Ile Gln Glu Ser
1               5                   10                  15

Ile Ala

<210> SEQ ID NO 32
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Ser Ile Glu Gln Ile Gln Lys Tyr Ile Ala Arg Ile Gln Glu Lys
1               5                   10                  15

Ile Ala Tyr Ile Gln Lys Met Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Ile Ala Ile Gly Ser Gln Ile Leu Ala Ile Leu Asp Gln Ile
                85                  90                  95

Tyr Ala Met Thr Pro
            100

<210> SEQ ID NO 33
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Ser Ile Glu Gln Ile Gln Lys Leu Ile Ala Val Ile Gln Glu Tyr
1               5                   10                  15

Ile Ala Leu Ile Gln Lys Lys Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Lys Ala Ile Ala Thr Gln Ile Ser Ala Ile Ile Arg Gln Ile
                85                  90                  95

Phe Ala Met Thr Pro
            100
```

```
<210> SEQ ID NO 34
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Ser Ile Glu Gln Ile Gln Lys Trp Ile Ala Gln Ile Gln Glu Asn
1               5                   10                  15

Ile Ala Asp Ile Gln Lys Leu Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
50                  55                  60

Gly Ser Gly Gly Gly Gly Ser Gly Gly Ser Ile Glu Gln Ile Gln Lys
65                  70                  75                  80

Gln Ile Pro Ala Ile Ala Tyr Gln Ile Leu Ala Ile Ile Arg Gln Ile
                85                  90                  95

Ser Ala Met Thr Pro
            100

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ser Ile Glu Gln Ile Gln Lys Trp Ile Ala Gly Ile Gln Glu Ala
1               5                   10                  15

Ile Ala

<210> SEQ ID NO 36
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Ser Ile Glu Gln Ile Gln Lys Leu Ile Ala Arg Ile Gln Glu Ser
1               5                   10                  15

Ile Ala Met Ile Gln Lys Lys Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
50                  55                  60

Gly Ser Gly Gly Gly Gly Ser Gly Gly Ser Ile Glu Gln Ile Gln Lys
65                  70                  75                  80

Gln Ile Ile Ala Ile Ala Lys Gln Ile Leu Ala Ile Val Ser Gln Ile
                85                  90                  95

Lys Ala Met Thr Pro
            100
```

```
<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Ile Glu Gln Ile Gln Lys Leu Ile Ala Phe Ile Gln Glu Gly
1               5                   10                  15

Ile Ala Ser Ile Gln Lys
            20

<210> SEQ ID NO 38
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Ser Ile Glu Gln Ile Gln Lys Thr Ile Ala Arg Ile Gln Glu Gly
1               5                   10                  15

Ile Ala Val Ile Gln Lys Leu Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
50                  55                  60

Gly Ser Gly Gly Gly Ser Gly Gly Ser Ile Glu Gln Ile Gln Lys
65                  70                  75                  80

Gln Ile Arg Ala Ile Val Arg Gln Ile Thr Ala Ile Met Thr Gln Ile
                85                  90                  95

Phe Ala Met Thr Pro
            100

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ser Ile Glu Gln Ile Gln Lys Ala Ile Ala Arg Ile Gln Glu
1               5                   10                  15

<210> SEQ ID NO 40
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ser Ile Glu Gln Ile Gln Lys Gly Ile Ala Pro Ile Gln Glu Met
1               5                   10                  15

Ile Ala Ser Ile Gln Lys Val Ile Tyr Ala Met Thr Gly Gly Ser Gly
            20                  25                  30
```

```
Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
 50                  55                  60

Gly Ser Gly Gly Gly Ser Gly Gly Ser Ile Glu Gln Ile Gln Lys
 65                  70                  75                  80

Gln Ile Met Ala Ile Ala Phe Gln Ile Phe Ala Ile Met Arg Gln Ile
                 85                  90                  95

Leu Ala Met Thr Pro
            100

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Ile Glu Gln Ile Gln Lys Pro Ile Ala
 1               5                  10

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ser Ile Glu Gln Ile Gln Lys
 1               5

<210> SEQ ID NO 43
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Ser Ile Glu Gln Ile Gln Lys Phe Ile Ala Pro Ile Gln Glu Tyr
 1               5                  10                  15

Ile Ala Ala Ile Gln Lys Ile Ile Tyr Ala Met Thr Gly Gly Ser Gly
                 20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
 50                  55                  60

Gly Ser Gly Gly Gly Ser Gly Gly Ser Ile Glu Gln Ile Gln Lys
 65                  70                  75                  80

Gln Ile Ala Ala Ile Ala Ser Gln Ile Lys Ala Ile Val Thr Gln Ile
                 85                  90                  95

Val Ala Met Thr Pro
            100
```

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gly Ser Ile Glu Gln Ile Gln Lys Ile Ala Gly Ile Gln Glu
1               5                   10                  15

<210> SEQ ID NO 45
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Gly Ser Ile Glu Gln Ile Gln Lys Phe Ile Ala Ser Ile Gln Glu Ser
1               5                   10                  15

Ile Ala Arg Ile Gln Lys Ser Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Thr Ala Ile Ala Arg Gln Ile Val Ala Ile Ile Val Gln Ile
                85                  90                  95

Thr Ala Met Thr Pro
            100

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gly Ser Ile Glu Gln Ile Gln Lys Phe Ile Ala Ala Ile Gln Glu Tyr
1               5                   10                  15

Ile Ala Thr Ile Gln Lys
            20

<210> SEQ ID NO 47
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Gly Ser Ile Glu Gln Ile Gln Lys Gly Ile Ala Ile Ile Gln Glu Thr
1               5                   10                  15

Ile Ala Tyr Ile Gln Lys Ser Ile Tyr Ala Met Thr Gly Gly Ser Gly
            20                  25                  30

-continued

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
    50                  55                  60

Gly Ser Gly Gly Gly Ser Gly Gly Ser Ile Glu Gln Ile Gln Lys
65                  70                  75                  80

Gln Ile Thr Ala Ile Ala Arg Gln Ile Thr Ala Ile Ile Ala Gln Ile
                85                  90                  95

Phe Ala Met Thr Pro
            100

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ser Ile Glu Gln Ile Gln Lys Thr Ile Ala
1               5                   10

<210> SEQ ID NO 49
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Ser Ile Glu Gln Ile Gln Lys Val Ile Ala Pro Ile Gln Glu Tyr
1               5                   10                  15

Ile Ala Ile Ile Gln Lys Tyr Ile Tyr Ala Met Thr Gly Gly Ser Gly
            20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
    50                  55                  60

Gly Ser Gly Gly Gly Ser Gly Gly Ser Ile Glu Gln Ile Gln Lys
65                  70                  75                  80

Gln Ile Ser Ala Ile Met Arg Gln Ile Tyr Ala Ile Ile Ser Gln Ile
                85                  90                  95

Gln Ala Met Thr Pro
            100

<210> SEQ ID NO 50
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Ser Ile Glu Gln Ile Gln Lys Leu Ile Ala Ser Ile Gln Glu Tyr
1               5                   10                  15

Ile Ala Thr Ile Gln Lys Leu Ile Tyr Ala Met Thr Gly Gly Ser Gly
            20                  25                  30

```
Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
 50                  55                  60

Gly Ser Gly Gly Gly Ser Gly Gly Ser Ile Glu Gln Ile Gln Lys
 65                  70                  75                  80

Gln Ile Ser Ala Ile Met Ile Gln Ile Asn Ala Ile Leu Gly Gln Ile
                 85                  90                  95

Phe Ala Met Thr Pro
            100

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ser Ile Glu Gln Ile Gln Lys Gly Ile Ala Val Ile Gln Glu Thr
 1               5                  10                  15

Ile Ala

<210> SEQ ID NO 52
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (19)..(19)
<223> OTHER INFORMATION: Any amino acid

<400> SEQUENCE: 52

Gly Ser Ile Glu Gln Ile Gln Lys Xaa Ile Ala Xaa Ile Gln Glu Ala
 1               5                  10                  15

Ile Ala Xaa Ile Gln Lys Val Ile Tyr Ala Met Thr Gly Gly Ser Gly
                 20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
 50                  55                  60

Gly Ser Gly Gly Gly Gly Ser Gly Gly Ser Ile Glu Gln Ile Gln Lys
 65                  70                  75                  80

Gln Ile

<210> SEQ ID NO 53
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (94)..(94)
<223> OTHER INFORMATION: Any amino acid
<220> FEATURE:
<221> NAME/KEY: MOD_RES
<222> LOCATION: (97)..(97)
<223> OTHER INFORMATION: Any amino acid

<400> SEQUENCE: 53

Gly Ser Ile Glu Gln Ile Gln Lys Arg Ile Ala Tyr Ile Gln Glu Ala
1               5                   10                  15

Ile Ala Arg Ile Gln Lys Trp Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Gly Ser Gly Gly Ser Ile Glu Gln Ile Gln Lys
65                  70                  75                  80

Gln Ile Gly Ala Ile Xaa Met Gln Ile Leu Ala Ile Phe Xaa Gln Ile
                85                  90                  95

Xaa Ala Met Thr Pro
            100

<210> SEQ ID NO 54
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Ser Ile Glu Gln Ile Gln Lys Lys Ile Ala Gly Ile Gln Glu Val
1               5                   10                  15

Ile Ala Leu Ile Gln Lys Phe Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Gly Ser Gly Gly Ser Ile Glu Gln Ile Gln Lys
65                  70                  75                  80

Gln Ile Arg Ala Ile Ser Ser Gln Ile Gln Ala Ile Val Leu Gln Ile
                85                  90                  95

Leu Ala Met Thr Pro
            100

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 55

Gly Ser Ile Glu Gln Ile Gln Lys Phe Ile Ala Ala Ile Gln Glu Tyr
1               5                   10                  15

Ile Ala Thr Ile Gln Lys
            20

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ser Ile Glu Gln Ile Gln Lys Gly Ile Ala Pro Ile Gln Glu Pro
1               5                   10                  15

Ile Ala

<210> SEQ ID NO 57
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Ser Ile Glu Gln Ile Gln Lys Ala Ile Ala Lys Ile Gln Glu Thr
1               5                   10                  15

Ile Ala Phe Ile Gln Lys Ser Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Thr Ala Ile Ala Gly Gln Ile Tyr Ala Ile Leu Gln Gln Ile
                85                  90                  95

Phe Ala Met Thr Pro
            100

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
```

```
<400> SEQUENCE: 58

Gly Xaa Ile Glu Xaa Ile Xaa Lys
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Ser Ile Glu Gln Ile Gln Lys
1               5

<210> SEQ ID NO 60
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (94)..(94)
<223> OTHER INFORMATION: Any amino acid

<400> SEQUENCE: 60

Gly Ser Ile Glu Gln Ile Gln Lys Xaa Ile Ala Trp Ile Gln Glu Tyr
1               5                   10                  15

Ile Ala Xaa Ile Gln Lys Xaa Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
50                  55                  60

Gly Ser Gly Gly Gly Gly Ser Gly Gly Ser Ile Glu Gln Ile Gln Lys
65                  70                  75                  80

Gln Ile Xaa Ala Ile Ala Thr Gln Ile Leu Ala Ile Val Xaa Gln Ile
                85                  90                  95

Val Ala Met Thr Pro
            100

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 61

Gly Ser Ile Glu Gln Ile Gln Lys Phe Ile Ala Met Ile Gln Glu Val
1               5                   10                  15

Ile Ala

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ser Ile Glu Gln Ile Gln Lys Arg Ile Ala
1               5                   10

<210> SEQ ID NO 63
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (66)..(66)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (75)..(75)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (94)..(94)
<223> OTHER INFORMATION: Any amino acid

<400> SEQUENCE: 63

Gly Ser Ile Glu Gln Ile Gln Lys Val Ile Ala Xaa Ile Gln Glu Tyr
1               5                   10                  15

Ile Ala Gly Ile Gln Lys Xaa Ile Tyr Ala Met Thr Gly Gly Ser Gly
                20                  25                  30

```
Gly Ser Gly Gly Gly Xaa Ile Glu Xaa Ile Gln Lys Gln Ile Ala Ala
            35                  40                  45

Ile Xaa Lys Gln Ile Ala Ala Ile Gln Lys Gln Ile Tyr Ala Met Thr
 50                  55                  60

Gly Xaa Gly Gly Gly Ser Xaa Gly Ser Xaa Glu Gln Ile Xaa Lys
 65                  70                  75                  80

Gln Ile Arg Ala Ile Thr Ser Gln Ile Trp Ala Ile Xaa Gln Ile
                 85                  90                  95

Ile Ala Met Thr Pro
            100

<210> SEQ ID NO 64
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (68)..(68)
<223> OTHER INFORMATION: Any amino acid
<220> FEATURE:
<221> NAME/KEY: MOD_RES
<222> LOCATION: (87)..(87)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (94)..(94)
<223> OTHER INFORMATION: Any amino acid

<400> SEQUENCE: 64

Gly Ser Ile Glu Gln Ile Gln Lys Tyr Ile Ala Xaa Ile Gln Glu Thr
 1               5                  10                  15

Ile Ala Xaa Ile Gln Lys Leu Ile Tyr Ala Met Thr Gly Ser Gly
                 20                  25                  30

Gly Ser Gly Gly Gly Ser Ile Glu Gln Ile Gln Lys Xaa Ile Ala Xaa
            35                  40                  45

Ile Gln Lys Gln Ile Ala Ala Ile Gln Lys Gln Ile Tyr Ala Met Thr
 50                  55                  60

Gly Ser Gly Xaa Gly Gly Ser Gly Gly Ser Ile Glu Gln Ile Gln Lys
 65                  70                  75                  80

Gln Ile Ser Ala Ile Ile Xaa Gln Ile Xaa Ala Ile Leu Xaa Gln Ile
                 85                  90                  95

Pro Ala Met Thr Pro
            100
```

-continued

```
<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Ser Ile Glu Gln Ile Gln Lys Val Ile Ala Gln Ile Gln Glu
1               5                   10                  15

<210> SEQ ID NO 66
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Ser Ile Glu Gln Ile Gln Lys Trp Ile Ala Leu Ile Gln Glu Lys
1               5                   10                  15

Ile Ala Arg Ile Gln Lys Asp Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Asn Ala Ile Ala Gly Gln Ile Leu Ala Ile Ala Thr Gln Ile
                85                  90                  95

Met Ala Met Thr Pro
            100

<210> SEQ ID NO 67
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Any amino acid

<400> SEQUENCE: 67

Gly Ser Ile Glu Gln Ile Gln Lys Val Ile Ala Ser Ile Gln Glu Arg
1               5                   10                  15

Ile Ala Xaa Ile Gln Lys Arg Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80
```

Gln Ile Gly Ala Ile Met Leu Gln Ile Met Ala Ile Ile Arg Gln Ile
                85                  90                  95

Pro Ala Met Thr Pro
            100

<210> SEQ ID NO 68
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gly Ser Ile Glu Gln Ile Gln Lys Arg Ile Ala Gly Ile Gln Glu Tyr
1               5                   10                  15

Ile Ala Lys Ile Gln Lys Ser Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Ser Ala Ile Ser Arg Gln Ile Val Ala Ile Val Ser Gln Ile
                85                  90                  95

Leu Ala Met Thr Pro
            100

<210> SEQ ID NO 69
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Ser Ile Glu Gln Ile Gln Lys Asn Ile Ala Pro Ile Gln Glu Val
1               5                   10                  15

Ile Ala Arg Ile Gln Lys Cys Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile

<210> SEQ ID NO 70
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 70

Gly Ser Ile Glu Gln Ile Gln Lys Thr Ile Ala Trp Ile Gln Glu Ser
1               5                   10                  15

Ile Ala Asn Ile Gln Lys Gly Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Arg Ala Ile Gly
                85

<210> SEQ ID NO 71
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Ser Ile Glu Gln Ile Gln Lys Val Ile Ala Arg Ile Gln Glu Pro
1               5                   10                  15

Ile Ala Val Ile Gln Lys Met Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80

Gln Ile Ser Ala Ile Arg Ser Gln Ile Leu Ala Ile Ile Arg Gln Ile
                85                  90                  95

Phe Ala Met Thr Pro
                100

<210> SEQ ID NO 72
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Ser Ile Glu Gln Ile Gln Lys Thr Ile Ala Lys Ile Gln Glu Arg
1               5                   10                  15

Ile Ala Trp Ile Gln Lys Val Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Gly Ser Gly Gly Ser Ile Glu Gln Ile Gln Lys
65                  70                  75                  80
```

Gln Ile Lys Ala Ile Ser Tyr Gln Ile Ile Ala Met Arg Gln Ile
                85                  90                  95

Leu Ala Met Thr Pro
            100

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ser Ile Glu Gln Ile Gln Lys His Ile Ala
1               5                   10

<210> SEQ ID NO 74
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gly Ser Ile Glu Gln Ile Gln Lys Val Ile Ala Trp Ile Gln Glu Ser
1               5                   10                  15

Ile Ala Ser Ile Gln Lys Arg Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Gly Ser Gly Gly Ser Ile Glu Gln Ile Gln Lys
65                  70                  75                  80

Gln Ile Gln Ala Ile Ala Asn Gln Ile Thr Ala Ile Val Arg Gln Ile
                85                  90                  95

Ile Ala Met Thr Pro
            100

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Ile Glu Gln Ile Gln Lys Val Ile Ala
1               5                   10

<210> SEQ ID NO 76
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(16)
<223> OTHER INFORMATION: Any amino acid

```
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (43)..(44)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (66)..(67)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (101)..(101)
<223> OTHER INFORMATION: Any amino acid

<400> SEQUENCE: 76

Gly Ser Ile Glu Gln Ile Gln Lys Gly Ile Ala Ala Ile Gln Xaa Xaa
1               5                   10                  15

Ile Ala Met Ile Xaa Lys Ser Ile Tyr Ala Met Thr Gly Gly Ser Gly
            20                  25                  30

Gly Ser Gly Gly Gly Ser Ile Glu Gln Ile Xaa Xaa Gln Ile Ala Xaa
        35                  40                  45

Ile Gln Lys Gln Ile Ala Ala Ile Gln Lys Gln Ile Tyr Ala Met Thr
    50                  55                  60

Gly Xaa Xaa Gly Gly Gly Ser Gly Gly Ser Ile Glu Xaa Ile Xaa Lys
65                  70                  75                  80

Gln Ile Thr Ala Ile Xaa Thr Gln Ile Xaa Ala Ile Xaa Ser Gln Ile
                85                  90                  95

Leu Xaa Met Thr Xaa
            100

<210> SEQ ID NO 77
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 77

Gly Ser Ile Glu Gln Ile Gln Lys Cys Ile Ala Phe Ile Gln Glu Arg
1               5                   10                  15

Ile Ala Gly Ile Gln Lys Arg Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Ser Gly Gly Ser Ile Glu Gln Ile Gln Lys
65                  70                  75                  80

Gln Ile Phe Ala Ile Gly Lys Gln Ile Phe Ala Ile Val Lys Gln Ile
            85                  90                  95

Leu Ala Met Thr Pro
            100

<210> SEQ ID NO 78
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Ser Ile Glu Gln Ile Gln Lys Pro Ile Ala Ala Ile Gln Glu Lys
1               5                   10                  15

Ile Ala Arg Ile Gln Lys Arg Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Ser Gly Gly Gly Ser Gly Gly Ser Ile Glu Gln Ile Gln Lys
65                  70                  75                  80

Gln Ile Met Ala Ile Asn Arg Gln Ile Leu Ala Ile Leu Arg Gln Ile
            85                  90                  95

Leu Ala Met Thr Pro
            100

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ser Ile Glu Gln Ile Gln Lys Tyr Ile Ala
1               5                   10

<210> SEQ ID NO 80
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 80

Gly Ser Ile Glu Gln Ile Gln Lys Phe Ile Ala Ser Ile Gln Glu Cys
1               5                   10                  15

Ile Ala Ser Ile Gln Lys Val Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Ser Gly Gly Ser Ile Glu Gln Ile Gln Lys
65                  70                  75                  80

Gln Ile Gly Ala Ile Ala Ala Gln Ile Ile Ala Ile Val Glu Gln Ile
                85                  90                  95

Val Ala Met Thr Pro
            100

<210> SEQ ID NO 81
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Ser Ile Glu Gln Ile Gln Lys Lys Ile Ala Tyr Ile Gln Glu Met
1               5                   10                  15

Ile Ala Leu Ile Gln Lys Gly Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Ser Gly Gly Ser Ile Glu Gln Ile Gln Lys
65                  70                  75                  80

Gln Ile Ser Ala Ile Ala Ala Gln Ile Ser Ala Ile Ile Lys Gln Ile
                85                  90                  95

Met Ala Met Thr Pro
            100

<210> SEQ ID NO 82
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Ser Ile Glu Gln Ile Gln Lys Asn Ile Ala Trp Ile Gln Glu Arg
1               5                   10                  15

Ile Ala Met Ile Gln Lys Leu Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60
```

Gly Ser Gly Gly Gly Gly Ser Gly Gly Ser Ile Glu Gln Ile Gln Lys
65                  70                  75                  80

Gln Ile

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ser Ile Glu Gln Ile Gln Lys Leu Ile Ala Arg Ile Gln Glu
1               5                   10                  15

<210> SEQ ID NO 84
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Ser Ile Glu Gln Ile Gln Lys Gly Ile Ala Ala Ile Gln Glu Trp
1               5                   10                  15

Ile Ala Thr Ile Gln Lys Arg Ile Tyr Ala Met Thr Gly Gly Ser Gly
                20                  25                  30

Gly Ser Gly Gly Gly Ser Ile Glu Gln Ile Gln Lys Gln Ile Ala Ala
            35                  40                  45

Ile Gln Lys Gln Ile Ala Ala Ile Gln Lys Gln Ile Tyr Ala Met Thr
        50                  55                  60

Gly Ser Gly Gly Gly Gly Ser Gly Gly Ser Ile Glu Gln Ile Gln Lys
65                  70                  75                  80

Gln Ile Arg Ala Ile Thr Ile Gln Ile Ile Ala Ile Ile Gln Gln Ile
                85                  90                  95

Trp Ala Met Thr Pro
            100

<210> SEQ ID NO 85
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (23)..(23)
<223> OTHER INFORMATION: Any amino acid

```
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (86)..(87)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (93)..(94)
<223> OTHER INFORMATION: Any amino acid
<220> FEATURE:
<221> NAME/KEY: MOD_RES
<222> LOCATION: (97)..(97)
<223> OTHER INFORMATION: Any amino acid

<400> SEQUENCE: 85

Gly Ser Ile Glu Gln Ile Gln Lys Xaa Ile Ala Xaa Ile Gln Glu Xaa
1               5                   10                  15

Ile Ala Xaa Ile Gln Lys Xaa Ile Tyr Ala Met Thr Gly Gly Ser Gly
            20                  25                  30

Gly Ser Gly Gly Gly Ser Ile Glu Gln Ile Gln Lys Gln Ile Ala Ala
        35                  40                  45

Ile Gln Lys Gln Ile Ala Ala Ile Gln Lys Gln Ile Tyr Ala Met Thr
50                  55                  60

Gly Ser Gly Gly Gly Ser Gly Gly Ser Ile Glu Gln Ile Gln Lys
65                  70                  75                  80

Gln Ile Xaa Ala Ile Xaa Xaa Gln Ile Xaa Ala Ile Xaa Xaa Gln Ile
                85                  90                  95

Xaa Ala Met Thr Pro
            100

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 86

His His His His His His
1               5

<210> SEQ ID NO 87
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Any amino acid

<400> SEQUENCE: 87

Ile Gln Glu Trp Ile Ala Arg Xaa Gln Lys Ser Ile Tyr Ala Met Thr
1               5                   10                  15

Gly Gly Ser Gly Gly Ser Gly Gly Gly Ser Ile Glu Gln Ile Gln Lys
            20                  25                  30
```

Gln Ile Ala Ala Ile Gln Lys Gln Ile Ala Ala Ile Gln Lys Gln Ile
            35                  40                  45

Tyr Ala Met Thr Gly Ser Gly Gly Gly Ser Gly Gly Ser Ile Glu
    50                  55                  60

Gln Ile Gln Lys Gln Ile Arg Ala Ile Ser Glu Gln Ile Val Ala Ile
65                  70                  75                  80

Met Leu Gln Ile Met Ala Met Thr Pro
                85

<210> SEQ ID NO 88
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ile Tyr Ala Met Thr Gly Gly Ser Gly Gly Ser Gly Gly Gly Ser Ile
1               5                   10                  15

Glu Gln Ile Gln Lys Gln Ile Ala Ala Ile Gln Lys Gln Ile Ala Ala
                20                  25                  30

Ile Gln Lys Gln Ile Tyr Ala Met Thr Gly Ser Gly Gly Gly Ser
            35                  40                  45

Gly Gly Ser Ile Glu Gln Ile Gln Lys Gln Ile Ser Ala Ile Val Gln
    50                  55                  60

Gln Ile Met Ala Ile Phe Ala Gln Ile Thr Ala Met Thr Pro
65                  70                  75

<210> SEQ ID NO 89
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ile Ala Leu Ile Gln Lys Ser Ile Tyr Ala Met Thr Gly Gly Ser Gly
1               5                   10                  15

Gly Ser Gly Gly Gly Ser Ile Glu Gln Ile Gln Lys Gln Ile Ala Ala
                20                  25                  30

Ile Gln Lys Gln Ile Ala Ala Ile Gln Lys Gln Ile Tyr Ala Met Thr
            35                  40                  45

Gly Ser Gly Gly Gly Ser Gly Gly Ser Ile Glu Gln Ile Gln Lys
    50                  55                  60

Gln Ile Ala Ala Ile Ala Arg Gln Ile Phe Ala Ile Ile Asn Gln Ile
65                  70                  75                  80

Thr Ala Met Thr Pro
                85

<210> SEQ ID NO 90
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 90

Ile Gln Lys Gly Ile Tyr Ala Met Thr Gly Gly Ser Gly Gly Ser Gly
1               5                   10                  15

Gly Gly Ser Ile Glu Gln Ile Gln Lys Gln Ile Ala Ala Ile Gln Lys
            20                  25                  30

Gln Ile Ala Ala Ile Gln Lys Gln Ile Tyr Ala Met Thr Gly Ser Gly
        35                  40                  45

Gly Gly Ser Gly Gly Ser Ile Glu Gln Ile Gln Lys Gln Ile Trp
    50                  55                  60

Ala Ile Ser Gln Gln Ile Thr Ala Ile Val Gln Ile Phe Ala Met
65                  70                  75                  80

Thr Pro

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Ile Gly Ser Gln Ile Thr Ala Ile Val Arg Gln Ile Leu Ala Met
1               5                   10                  15

Thr Pro

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Ile Arg Ala Met Thr Pro
1               5

<210> SEQ ID NO 93
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Any amino acid

<400> SEQUENCE: 93

Ile Gln Lys Tyr Ile Tyr Ala Met Thr Gly Gly Ser Gly Gly Ser Gly
1               5                   10                  15

Gly Gly Ser Ile Glu Gln Ile Gln Lys Gln Ile Ala Ala Ile Gln Lys
            20                  25                  30

Gln Ile Ala Ala Ile Gln Lys Gln Ile Tyr Ala Met Thr Gly Ser Gly
        35                  40                  45

Gly Gly Gly Ser Gly Gly Ser Ile Glu Gln Ile Gln Lys Gln Ile Phe
    50                  55                  60

```
Ala Ile Xaa Arg Gln Ile Met Ala Ile Leu Arg Gln Ile Asn Ala Met
 65                  70                  75                  80

Thr Pro

<210> SEQ ID NO 94
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ile Gln Lys Leu Ile Tyr Ala Met Thr Gly Ser Gly Gly Ser Gly
  1               5                  10                  15

Gly Gly Ser Ile Glu Gln Ile Gln Lys Gln Ile Ala Ala Ile Gln Lys
                 20                  25                  30

Gln Ile Ala Ala Ile Gln Lys Gln Ile Tyr Ala Met Thr Gly Ser Gly
             35                  40                  45

Gly Gly Ser Gly Gly Ser Ile Glu Gln Ile Gln Lys Gln Ile Arg
         50                  55                  60

Ala Ile Arg Ser Gln Ile Arg Ala Ile Leu Ser Gln Ile Ile Ala Met
 65                  70                  75                  80

Thr Pro

<210> SEQ ID NO 95
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ile Tyr Ala Met Thr Gly Gly Ser Gly Gly Ser Gly Gly Gly Ser Ile
  1               5                  10                  15

Glu Gln Ile Gln Lys Gln Ile Ala Ala Ile Gln Lys Gln Ile Ala Ala
                 20                  25                  30

Ile Gln Lys Gln Ile Tyr Ala Met Thr Gly Ser Gly Gly Gly Ser
             35                  40                  45

Gly Gly Ser Ile Glu Gln Ile Gln Lys Gln Ile Ala Ala Ile Gly Asn
         50                  55                  60

Gln Ile Met Ala Ile Leu Gln Gln Ile Lys Ala Met Thr Pro
 65                  70                  75

<210> SEQ ID NO 96
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ile Ala Ile Ile Gln Lys Lys Ile Tyr Ala Met Thr Gly Gly Ser Gly
  1               5                  10                  15

Gly Ser Gly Gly Gly Ser Ile Glu Gln Ile Gln Lys Gln Ile Ala Ala
                 20                  25                  30

Ile Gln Lys Gln Ile Ala Ala Ile Gln Lys Gln Ile Tyr Ala Met Thr
             35                  40                  45
```

```
Gly Ser Gly Gly Gly Gly Ser Gly Gly Ser Ile Glu Gln Ile Gln Lys
            50                  55                  60
Gln Ile Val Ala Ile Ile Ala Gln Ile Ala Ala Ile Pro Gln Ile
 65                  70                  75                  80
Ile Ala Met Thr Pro
                85

<210> SEQ ID NO 97
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ile Gln Glu Arg Ile Ala Trp Ile Gln Lys Arg Ile Tyr Ala Met Thr
  1               5                  10                  15
Gly Gly Ser Gly Gly Ser Gly Gly Ser Ile Glu Gln Ile Gln Lys
                 20                  25                  30
Gln Ile Ala Ala Ile Gln Lys Gln Ile Ala Ala Ile Gln Lys Gln Ile
             35                  40                  45
Tyr Ala Met Thr Gly Ser Gly Gly Gly Ser Gly Gly Ser Ile Glu
         50                  55                  60
Gln Ile Gln Lys Gln Ile Glu Ala Ile Thr Gly Gln Ile Val Ala Ile
 65                  70                  75                  80
Val Phe Gln Ile Tyr Ala Met Thr Pro
                85

<210> SEQ ID NO 98
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ile Ala Lys Ile Gln Glu Phe Ile Ala Arg Ile Gln Lys Val Ile Tyr
  1               5                  10                  15
Ala Met Thr Gly Gly Ser Gly Gly Ser Gly Gly Ser Ile Glu Gln
                 20                  25                  30
Ile Gln Lys Gln Ile Ala Ala Ile Gln Lys Gln Ile Ala Ala Ile Gln
             35                  40                  45
Lys Gln Ile Tyr Ala Met Thr Gly Ser Gly Gly Gly Ser Gly Gly
         50                  55                  60
Ser Ile Glu Gln Ile Gln Lys Gln Ile Cys Ala Ile Ala Val Gln Ile
 65                  70                  75                  80
Asp Ala Ile Leu Gly Gln Ile Leu Ala Met Thr Pro
                85                  90

<210> SEQ ID NO 99
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 99

Ile Ala Leu Ile Gln Lys Ala Ile Tyr Ala Met Thr Gly Ser Gly
1               5                   10                  15

Gly Ser Gly Gly Gly Ser Ile Glu Gln Ile Gln Lys Gln Ile Ala Ala
            20                  25                  30

Ile Gln Lys Gln Ile Ala Ala Ile Gln Lys Gln Ile Tyr Ala Met Thr
        35                  40                  45

Gly Ser Gly Gly Gly Ser Gly Gly Ser Ile Glu Gln Ile Gln Lys
    50                  55                  60

Gln Ile Tyr Ala Ile Gly Leu Gln Ile Leu Ala Ile Met Asn Gln Ile
65                  70                  75                  80

Trp Ala Met Thr Pro
                85

<210> SEQ ID NO 100
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid

<400> SEQUENCE: 100

Ile Tyr Ala Met Thr Gly Gly Ser Gly Gly Ser Gly Gly Gly Ser Ile
1               5                   10                  15

Glu Gln Ile Gln Lys Gln Ile Ala Ala Ile Xaa Lys Gln Ile Ala Ala
            20                  25                  30

Ile Gln Lys Gln Ile Tyr Ala Met Thr Gly Ser Gly Gly Gly Ser
        35                  40                  45

Gly Gly Ser Ile Glu Gln Ile Gln Lys Gln Ile Gly Ala Ile Ala Tyr
    50                  55                  60

Gln Ile Ile Ala Ile Val Asn Gln Ile Lys Ala Met Thr Pro
65                  70                  75

<210> SEQ ID NO 101
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ile Gln Glu Pro Ile Ala Ile Gln Lys Arg Ile Tyr Ala Met Thr
1               5                   10                  15

Gly Gly Ser Gly Gly Ser Gly Gly Gly Ser Ile Glu Gln Ile Gln Lys
            20                  25                  30

Gln Ile Ala Ala Ile Gln Lys Gln Ile Ala Ala Ile Gln Lys Gln Ile
        35                  40                  45

Tyr Ala Met Thr Gly Ser Gly Gly Gly Ser Gly Gly Ser Ile Glu
    50                  55                  60

Gln Ile Gln Lys Gln Ile Lys Ala Ile Thr Ser Gln Ile Ser Ala Ile
65                  70                  75                  80

Met Ser Gln Ile Trp Ala Met Thr Pro
                85
```

```
<210> SEQ ID NO 102
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ile Gln Lys Ile Ile Tyr Ala Met Thr Gly Gly Ser Gly Gly Ser Gly
1               5                   10                  15

Gly Gly Ser Ile Glu Gln Ile Gln Lys Gln Ile Ala Ala Ile Gln Lys
                20                  25                  30

Gln Ile Ala Ala Ile Gln Lys Gln Ile Tyr Ala Met Thr Gly Ser Gly
            35                  40                  45

Gly Gly Gly Ser Gly Gly Ser Ile Glu Gln Ile Gln Lys Gln Ile Leu
        50                  55                  60

Ala Ile Ala Gln Gln Ile His Ala Ile Val Ser Gln Ile Val Ala Met
65                  70                  75                  80

Thr Pro

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Ile Trp Glu Gln Ile Ala Ala Ile Leu Lys Gln Ile Val Ala Met
1               5                   10                  15

Thr Pro

<210> SEQ ID NO 104
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ile Tyr Ala Met Thr Gly Gly Ser Gly Gly Ser Gly Gly Gly Ser Ile
1               5                   10                  15

Glu Gln Ile Gln Lys Gln Ile Ala Ala Ile Gln Lys Gln Ile Ala Ala
                20                  25                  30

Ile Gln Lys Gln Ile Tyr Ala Met Thr Gly Ser Gly Gly Gly Gly Ser
            35                  40                  45

Gly Gly Ser Ile Glu Gln Ile Gln Lys Gln Ile Gly Ala Ile Ala Tyr
        50                  55                  60

Gln Ile Ile Ala Ile Val Asn Gln Ile Lys Ala Met Thr Pro
65                  70                  75

<210> SEQ ID NO 105
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 105

Ile Gln Lys Leu Ile Tyr Ala Met Thr Gly Gly Ser Gly Gly Ser Gly
1               5                   10                  15

Gly Gly Ser Ile Glu Gln Ile Gln Lys Gln Ile Ala Ala Ile Gln Lys
            20                  25                  30

Gln Ile Ala Ala Ile Gln Lys Gln Ile Tyr Ala Met Thr Gly Ser Gly
        35                  40                  45

Gly Gly Gly Ser Gly Gly Ser Ile Glu Gln Ile Gln Lys Gln Ile
    50                  55                  60

<210> SEQ ID NO 106
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (81)..(81)
<223> OTHER INFORMATION: Any amino acid

<400> SEQUENCE: 106

Ile Ala Gly Ile Gln Glu Trp Ile Ala Pro Ile Xaa Lys Arg Ile Tyr
1               5                   10                  15

Ala Met Thr Gly Gly Ser Gly Gly Ser Gly Gly Gly Xaa Ile Glu Gln
            20                  25                  30

Ile Gln Lys Gln Ile Ala Ala Ile Gln Lys Gln Ile Ala Ala Ile Gln
        35                  40                  45

Lys Xaa Ile Tyr Ala Met Thr Gly Ser Gly Gly Gly Ser Gly Gly
    50                  55                  60

Ser Ile Glu Gln Ile Xaa Lys Gln Ile Ser Ala Ile Ile Asp Gln Ile
65                  70                  75                  80

Xaa Ala Ile Phe Ala Gln Ile Ile Ala Met Thr Pro
                85                  90

<210> SEQ ID NO 107
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ile Ala Gly Ile Gln Glu Trp Ile Ala Pro Ile Gln Lys Arg Ile Tyr
1               5                   10                  15

Ala Met Thr Gly Gly Ser Gly Gly Ser Gly Gly Gly Ser Ile Glu Gln
            20                  25                  30

-continued

Ile Gln Lys Gln Ile Ala Ala Ile Gln Lys Gln Ile Ala Ala Ile Gln
            35                  40                  45

Lys Gln Ile Tyr Ala Met Thr Gly Ser Gly Gly Gly Ser Gly Gly
 50                  55                  60

Ser Ile Glu Gln Ile Gln Lys Gln Ile Ser Ala Ile Ile Asp Gln Ile
 65                  70                  75                  80

Arg Ala Ile Phe Ala Gln Ile Ile Ala Met Thr Pro
                85                  90

<210> SEQ ID NO 108
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ile Gln Lys Asn Ile Tyr Ala Met Thr Gly Gly Ser Gly Gly Ser Gly
 1               5                  10                  15

Gly Gly Ser Ile Glu Gln Ile Gln Lys Gln Ile Ala Ala Ile Gln Lys
                20                  25                  30

Gln Ile Ala Ala Ile Gln Lys Gln Ile Tyr Ala Met Thr Gly Ser Gly
            35                  40                  45

Gly Gly Ser Gly Gly Ser Ile Glu Gln Ile Gln Lys Gln Ile Arg
 50                  55                  60

Ala Ile Arg Glu Gln Ile Lys Ala Ile Leu His Gln Ile Thr Ala Met
 65                  70                  75                  80

Thr Pro

<210> SEQ ID NO 109
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ile Gln Glu Pro Ile Ala Asn Ile Gln Lys Arg Ile Tyr Ala Met Thr
 1               5                  10                  15

Gly Gly Ser Gly Gly Ser Gly Gly Gly Ser Ile Glu Gln Ile Gln Lys
                20                  25                  30

Gln Ile Ala Ala Ile Gln Lys Gln Ile Ala Ala Ile Gln Lys Gln Ile
            35                  40                  45

Tyr Ala Met Thr Gly Ser Gly Gly Gly Ser Gly Gly Ser Ile Glu
 50                  55                  60

Gln Ile Gln Lys Gln Ile Glu Ala Ile Thr Asn Gln Ile Trp Ala Ile
 65                  70                  75                  80

Ile Thr Gln Ile Trp Ala Met Thr Pro
                85

<210> SEQ ID NO 110
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 110

Ile Ala Met Ile Gln Lys Ala Ile Tyr Ala Met Thr Gly Ser Gly
1               5                   10                  15

Gly Ser Gly Gly Gly Ser Ile Glu Gln Ile Gln Lys Gln Ile Ala Ala
                20                  25                  30

Ile Gln Lys Gln Ile Ala Ala Ile Gln Lys Gln Ile Tyr Ala Met Thr
            35                  40                  45

Gly Ser Gly Gly Gly Ser Gly Gly Ser Ile Glu Gln Ile Gln Lys
50                  55                  60

Gln Ile Arg Ala Ile Ile Met Gln Ile Ser Ala Ile Phe Asn Gln Ile
65                  70                  75                  80

Phe Ala Met Thr Pro
                85

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Ile Ser Ser Gln Ile Arg Ala Ile Leu Thr Gln Ile Leu Ala Met
1               5                   10                  15

Thr Pro

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Ile Ile Ala Ile Val Glu Gln Ile Trp Ala Met Thr Pro
1               5                   10

<210> SEQ ID NO 113
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ile Gln Glu Lys Ile Ala Trp Ile Gln Lys Leu Ile Tyr Ala Met Thr
1               5                   10                  15

Gly Gly Ser Gly Gly Ser Gly Gly Ser Ile Glu Gln Ile Gln Lys
                20                  25                  30

Gln Ile Ala Ala Ile Gln Lys Gln Ile Ala Ala Ile Gln Lys Gln Ile
            35                  40                  45

Tyr Ala Met Thr Gly Ser Gly Gly Gly Ser Gly Gly Ser Ile Glu
50                  55                  60

Gln Ile Gln Lys Gln Ile Ser Ala Ile Gly Gln Ile Tyr Ala Ile
65                  70                  75                  80

Ala Ser Gln Ile Met Ala Met Thr Pro
                85
```

-continued

```
<210> SEQ ID NO 114
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ile Gln Glu Tyr Ile Ala Trp Ile Gln Lys Ser Ile Tyr Ala Met Thr
1               5                   10                  15

Gly Gly Ser Gly Gly Ser Gly Gly Gly Ser Ile Glu Gln Ile Gln Lys
            20                  25                  30

Gln Ile Ala Ala Ile Gln Lys Gln Ile Ala Ala Ile Gln Lys Gln Ile
        35                  40                  45

Tyr Ala Met Thr Gly Ser Gly Gly Gly Ser Gly Gly Ser Ile Glu
    50                  55                  60

Gln Ile Gln Lys Gln Ile Arg Ala Ile Ala Met Gln Ile Glu Ala Ile
65                  70                  75                  80

Ile Thr Gln Ile Arg Ala Met Thr Pro
                85

<210> SEQ ID NO 115
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ile Gln Glu Lys Ile Ala Trp Ile Gln Lys Met Ile Tyr Ala Met Thr
1               5                   10                  15

Gly Gly Ser Gly Gly Ser Gly Gly Gly Ser Ile Glu Gln Ile Gln Lys
            20                  25                  30

Gln Ile Ala Ala Ile Gln Lys Gln Ile Ala Ala Ile Gln Lys Gln Ile
        35                  40                  45

Tyr Ala Met Thr Gly Ser Gly Gly Gly Ser Gly Gly Ser Ile Glu
    50                  55                  60

Gln Ile Gln Lys Gln Ile Val Ala Ile Ser Phe Gln Ile Trp Ala Ile
65                  70                  75                  80

Val Arg Gln Ile Thr Ala Met Thr Pro
                85

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Ile Ile Tyr Gln Ile Val Ala Ile Ile Arg Gln Ile Pro Ala Met
1               5                   10                  15

Thr Pro

<210> SEQ ID NO 117
<211> LENGTH: 85
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 117

Ile Ala Leu Ile Gln Lys Arg Ile Tyr Ala Met Thr Gly Gly Ser Gly
1               5                   10                  15

Gly Ser Gly Gly Gly Ser Ile Glu Gln Ile Gln Lys Gln Ile Ala Ala
            20                  25                  30

Ile Gln Lys Gln Ile Ala Ala Ile Gln Lys Gln Ile Tyr Ala Met Thr
        35                  40                  45

Gly Ser Gly Gly Gly Gly Ser Gly Gly Ser Ile Glu Gln Ile Gln Lys
    50                  55                  60

Gln Ile Val Ala Ile Met Tyr Gln Ile Tyr Ala Ile Ile Lys Gln Ile
65                  70                  75                  80

Trp Ala Met Thr Pro
                85

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Ile Ala Asn Gln Ile Arg Ala Ile Ile Asn Gln Ile Met Ala Met
1               5                   10                  15

Thr Pro
```